(12) United States Patent
Marks

(10) Patent No.: US 7,312,044 B2
(45) Date of Patent: *Dec. 25, 2007

(54) TYPE 1 RYANODINE RECEPTOR-BASED METHODS

(75) Inventor: Andrew R. Marks, Larchmont, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/794,218

(22) Filed: Mar. 5, 2004

(65) Prior Publication Data

US 2004/0224368 A1    Nov. 11, 2004

Related U.S. Application Data

(60) Provisional application No. 60/452,664, filed on Mar. 7, 2003.

(51) Int. Cl.
*G01N 33/53* (2006.01)
*G01N 33/566* (2006.01)
*G01N 33/567* (2006.01)
*C12Q 1/00* (2006.01)

(52) U.S. Cl. ............................. 435/7.2; 435/4; 435/7.21
(58) Field of Classification Search ................. 435/7.1; 530/350
See application file for complete search history.

(56) References Cited

U.S. PATENT DOCUMENTS

| | | | |
|---|---|---|---|
| 3,367,930 A | 2/1968 | Schmutz et al. |
| 4,567,254 A | 1/1986 | Kataoka et al. |
| 4,658,055 A | 4/1987 | Onuki et al. |
| 4,723,012 A | 2/1988 | Matsumoto et al. |
| 4,841,055 A | 6/1989 | Matsumoto et al. |
| 4,845,065 A | 7/1989 | Sugimori et al. |
| 4,849,535 A | 7/1989 | Naora et al. |
| 4,888,418 A | 12/1989 | Kawai et al. |
| 4,990,707 A | 2/1991 | Mais et al. |
| 5,075,293 A | 12/1991 | Reifschneider et al. |
| 5,142,647 A | 8/1992 | Nakagawa et al. |
| 5,153,184 A | 10/1992 | Reifschneider et al. |
| 5,166,347 A | 11/1992 | Izawa et al. |
| 5,179,125 A | 1/1993 | Mimura et al. |
| 5,180,720 A | 1/1993 | Husa et al. |
| 5,182,272 A | 1/1993 | Hallinan et al. |
| 5,204,462 A | 4/1993 | Kobayashi et al. |
| 5,210,266 A | 5/1993 | Mimura et al. |
| 5,214,056 A | 5/1993 | Haruta et al. |
| 5,221,681 A | 6/1993 | Kabbe et al. |
| 5,223,508 A | 6/1993 | Izawa et al. |
| 5,260,286 A | 11/1993 | Lawson et al. |
| 5,272,164 A | 12/1993 | Izawa et al. |
| 5,304,380 A | 4/1994 | Miyajima et al. |
| 5,304,558 A | 4/1994 | Kaneko et al. |
| 5,304,644 A | 4/1994 | Husa et al. |
| 5,324,722 A | 6/1994 | Hagen et al. |
| 5,332,734 A | 7/1994 | Kobayashi et al. |
| 5,354,747 A | 10/1994 | Hansen, Jr. et al. |
| 5,354,758 A | 10/1994 | Lawson et al. |
| 5,387,684 A | 2/1995 | Inoue et al. |
| 5,413,929 A | 5/1995 | Ishizaki et al. |
| 5,416,066 A | 5/1995 | Kaneko et al. |
| 5,449,675 A | 9/1995 | Chandrakumar et al. |
| 5,453,282 A | 9/1995 | Kanauchi et al. |
| 5,457,182 A | 10/1995 | Wiederrecht et al. |
| 5,461,047 A | 10/1995 | Hansen, Jr. et al. |
| 5,476,780 A | 12/1995 | Watanabe et al. |
| 5,478,832 A | 12/1995 | Inoue et al. |
| 5,508,293 A | 4/1996 | Okawara et al. |
| 5,523,410 A | 6/1996 | Kagara et al. |
| 5,580,866 A | 12/1996 | Housley et al. |
| 5,593,988 A | 1/1997 | Tahara et al. |
| 5,624,961 A | 4/1997 | Ban et al. |
| 5,654,001 A | 8/1997 | Kanauchi et al. |
| 5,665,881 A | 9/1997 | Inoue et al. |
| 5,719,155 A | 2/1998 | Cho et al. |
| 5,723,458 A | 3/1998 | Brieaddy et al. |
| 5,750,696 A | 5/1998 | Shibata et al. |
| 5,753,649 A | 5/1998 | Tahara et al. |
| 5,767,247 A | 6/1998 | Kaneko et al. |
| 5,780,441 A | 7/1998 | Higa et al. |
| 5,792,655 A | 8/1998 | Watanabe et al. |
| 5,807,850 A | 9/1998 | Nakamura et al. |
| 5,817,652 A | 10/1998 | Brieaddy et al. |

(Continued)

FOREIGN PATENT DOCUMENTS

EP    0467325    1/1992

(Continued)

OTHER PUBLICATIONS

Reiken et al., J Cell Biol. 2003, vol. 160(6): pp. 919-928.*

(Continued)

*Primary Examiner*—Christine J. Saoud
*Assistant Examiner*—Jon M. Lockard
(74) *Attorney, Agent, or Firm*—Wilmer Cutler Pickering Hale and Dorr LLP

(57) ABSTRACT

This invention provides methods of treating defective skeletal muscle function during heart failure and methods for identifying compounds useful in such treatments.

10 Claims, 24 Drawing Sheets

U.S. PATENT DOCUMENTS

| | | |
|---|---|---|
| 5,824,862 A | 10/1998 | Hiyoshi et al. |
| 5,859,240 A | 1/1999 | Brieaddy |
| 5,906,819 A | 5/1999 | Kaibuchi et al. |
| 5,910,494 A | 6/1999 | Brieaddy |
| 6,013,499 A | 1/2000 | Narumiya et al. |
| 6,111,072 A | 8/2000 | Narumiya et al. |
| 6,130,060 A | 10/2000 | Nakamura, deceased et al. |
| 6,184,352 B1 | 2/2001 | Nakamura et al. |
| 6,235,730 B1 | 5/2001 | Sato et al. |
| 6,255,472 B1 | 7/2001 | Tokino et al. |
| 6,271,353 B1 | 8/2001 | Nakamura et al. |
| 6,313,113 B1 | 11/2001 | Lohray et al. |
| 6,316,485 B1 | 11/2001 | Nakamura et al. |
| 6,338,955 B2 | 1/2002 | Oguri et al. |
| 6,348,334 B1 | 2/2002 | Nagata et al. |
| 6,362,231 B1 | 3/2002 | Sakai et al. |
| 6,391,595 B1 | 5/2002 | Kato et al. |
| 6,403,830 B2 | 6/2002 | Webber et al. |
| 6,410,561 B1 | 6/2002 | Shinkai et al. |
| 6,426,365 B1 | 7/2002 | Shinkai et al. |
| 6,465,518 B2 | 10/2002 | Hansen, Jr. et al. |
| 6,465,686 B2 | 10/2002 | Grapperhaus et al. |
| 6,489,125 B1 * | 12/2002 | Marks et al. ............... 435/7.2 |
| 6,495,544 B2 | 12/2002 | Hansen, Jr. et al. |
| 6,500,816 B1 | 12/2002 | Ekimoto et al. |
| 6,506,745 B1 | 1/2003 | Aisaka et al. |
| 6,545,170 B2 | 4/2003 | Pitzele et al. |
| 6,562,618 B1 | 5/2003 | Tamatani et al. |
| 6,562,828 B1 | 5/2003 | Katoh et al. |
| 6,583,157 B2 | 6/2003 | McGee et al. |
| 6,586,474 B2 | 7/2003 | Webber et al. |
| 6,632,976 B1 | 10/2003 | Tomizuka et al. |
| 6,649,366 B2 | 11/2003 | Chubinskaya et al. |
| 6,660,837 B1 | 12/2003 | Kaibuchi et al. |
| 6,673,904 B2 | 1/2004 | Nishikawa et al. |
| 6,683,083 B1 | 1/2004 | Kaneko et al. |
| 6,750,255 B2 | 6/2004 | Sakai et al. |
| 6,753,346 B2 | 6/2004 | Shinkai et al. |
| 6,756,406 B2 | 6/2004 | Durley et al. |
| 6,787,668 B2 | 9/2004 | Pitzele et al. |
| 6,803,039 B2 | 10/2004 | Tsuji et al. |
| 6,812,252 B2 | 11/2004 | Ikawa et al. |
| 6,821,987 B2 | 11/2004 | Kubo et al. |
| 6,824,973 B2 | 11/2004 | Tang et al. |
| 6,828,456 B2 | 12/2004 | Hansen, Jr. et al. |
| 6,830,896 B2 | 12/2004 | Kaneko et al. |
| 6,852,753 B2 | 2/2005 | Koeller et al. |
| 6,869,975 B2 | 3/2005 | Abe et al. |
| 6,890,531 B1 | 5/2005 | Horie et al. |
| 6,897,295 B1 | 5/2005 | Nagata et al. |
| 6,906,072 B1 | 6/2005 | Yamamoto et al. |
| 6,914,158 B2 | 7/2005 | Webber et al. |
| 6,939,895 B2 | 9/2005 | Sakai et al. |
| 6,951,889 B2 | 10/2005 | Hansen, Jr. et al. |
| 6,962,926 B2 | 11/2005 | Laborde et al. |
| 6,964,975 B2 | 11/2005 | Ueno et al. |
| 6,977,252 B1 | 12/2005 | Kaneko et al. |
| 6,998,469 B2 | 2/2006 | Tandon et al. |
| 7,005,450 B2 | 2/2006 | Durley et al. |
| 7,029,671 B1 | 4/2006 | Koezuka et al. |
| 7,030,225 B1 | 4/2006 | Tamatani et al. |
| 7,041,870 B2 | 5/2006 | Tomizuka et al. |
| 7,045,615 B2 | 5/2006 | Tamatani et al. |
| 7,064,194 B2 | 6/2006 | Misawa et al. |
| 7,102,013 B2 | 9/2006 | Webber et al. |
| 7,112,655 B1 | 9/2006 | Tamatani et al. |
| 7,135,466 B2 | 11/2006 | Sakai et al. |
| 7,163,952 B2 | 1/2007 | Inaba et al. |
| 2002/0042405 A1 | 4/2002 | Schuh |
| 2002/0052358 A1 | 5/2002 | Chubinskaya et al. |
| 2002/0107406 A1 | 8/2002 | Sakai et al. |
| 2002/0115831 A1 | 8/2002 | Tamatani et al. |
| 2002/0132001 A1 | 9/2002 | Garthwaite et al. |
| 2002/0151685 A1 | 10/2002 | Tamatani et al. |
| 2002/0156242 A1 | 10/2002 | Tamatani et al. |
| 2002/0199213 A1 | 12/2002 | Tomizuka et al. |
| 2003/0044845 A1 | 3/2003 | Jenkins et al. |
| 2003/0054531 A1 | 3/2003 | Gretarsdottir et al. |
| 2003/0055027 A1 | 3/2003 | Schun |
| 2003/0055087 A1 | 3/2003 | Shinkai et al. |
| 2003/0064406 A1 | 4/2003 | Kaneko et al. |
| 2003/0083472 A1 | 5/2003 | Tamatani et al. |
| 2003/0087907 A1 | 5/2003 | Kubo et al. |
| 2003/0092708 A1 | 5/2003 | Shinkai et al. |
| 2003/0124637 A1 | 7/2003 | Kaneko et al. |
| 2003/0134331 A1 | 7/2003 | Marks et al. |
| 2003/0144526 A1 | 7/2003 | Sakai et al. |
| 2003/0176485 A1 | 9/2003 | Sakai et al. |
| 2003/0181764 A1 | 9/2003 | Ikawa et al. |
| 2003/0186885 A1 | 10/2003 | Tandon et al. |
| 2003/0191323 A1 | 10/2003 | Ikawa et al. |
| 2003/0195218 A1 | 10/2003 | Koeller et al. |
| 2003/0199482 A1 | 10/2003 | Seibert et al. |
| 2003/0199701 A1 | 10/2003 | Webber et al. |
| 2003/0220310 A1 | 11/2003 | Schuh |
| 2003/0220312 A1 | 11/2003 | Schuh |
| 2003/0232855 A1 | 12/2003 | Iwamura et al. |
| 2004/0006099 A1 | 1/2004 | Katoh et al. |
| 2004/0017409 A1 | 1/2004 | Mizutani et al. |
| 2004/0048780 A1 | 3/2004 | Marks |
| 2004/0053919 A1 | 3/2004 | Chubinskaya et al. |
| 2004/0073012 A1 | 4/2004 | Tamatani et al. |
| 2004/0073957 A1 | 4/2004 | Tomizuka et al. |
| 2004/0082653 A1 | 4/2004 | Nonaka et al. |
| 2004/0120945 A1 | 6/2004 | Tamatani et al. |
| 2004/0132658 A1 | 7/2004 | Tamatani et al. |
| 2004/0132727 A1 | 7/2004 | Sakai et al. |
| 2004/0146506 A1 | 7/2004 | Tamatani et al. |
| 2004/0146991 A1 | 7/2004 | Tsuji et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0171613 A1 | 9/2004 | Iwamura et al. |
| 2004/0173802 A1 | 9/2004 | Yukimoto |
| 2004/0175814 A1 | 9/2004 | Kato et al. |
| 2004/0180052 A1 | 9/2004 | Tsuji et al. |
| 2004/0186178 A1 | 9/2004 | Webber et al. |
| 2004/0192584 A1 | 9/2004 | McMahon et al. |
| 2004/0198719 A1 | 10/2004 | Laborde et al. |
| 2004/0209871 A1 | 10/2004 | Fox et al. |
| 2004/0220193 A1 | 11/2004 | Yamamoto et al. |
| 2004/0224368 A1 | 11/2004 | Marks |
| 2004/0225018 A1 | 11/2004 | Sunami et al. |
| 2004/0229781 A1 | 11/2004 | Marks et al. |
| 2004/0229788 A1 | 11/2004 | Tamatani et al. |
| 2004/0229790 A1 | 11/2004 | Tezuka et al. |
| 2004/0229803 A1 | 11/2004 | Stephenson et al. |
| 2004/0229876 A1 | 11/2004 | Kubo et al. |
| 2004/0229957 A1 | 11/2004 | Shinkai et al. |
| 2004/0235162 A1 | 11/2004 | Sato |
| 2004/0242683 A1 | 12/2004 | Urata et al. |
| 2005/0009733 A1 | 1/2005 | Stephenson et al. |
| 2005/0020668 A1 | 1/2005 | Urata et al. |
| 2005/0032210 A1 | 2/2005 | Sato et al. |
| 2005/0035939 A1 | 2/2005 | Akiyama |
| 2005/0051181 A1 | 3/2005 | Okamoto |
| 2005/0059655 A1 | 3/2005 | Garvey et al. |
| 2005/0059810 A1 | 3/2005 | Maeda et al. |
| 2005/0070543 A1 | 3/2005 | Stephenson |
| 2005/0070545 A1 | 3/2005 | Fox et al. |
| 2005/0074762 A1 | 4/2005 | Nakamura et al. |
| 2005/0113451 A1 | 5/2005 | Hansen et al. |
| 2005/0159365 A1 | 7/2005 | Serizawa et al. |
| 2005/0159403 A1 | 7/2005 | Stephenson et al. |

| | | |
|---|---|---|
| 2005/0165106 A1 | 7/2005 | Webber et al. |
| 2005/0171196 A1 | 8/2005 | Fujii et al. |
| 2005/0177884 A1 | 8/2005 | Tomizuka et al. |
| 2005/0186640 A1 | 8/2005 | Marks et al. |
| 2005/0187221 A1 | 8/2005 | Matsuda et al. |
| 2005/0187386 A1 | 8/2005 | Marks et al. |
| 2005/0192259 A1 | 9/2005 | Garthwaite et al. |
| 2005/0213426 A1 | 9/2005 | Midas et al. |
| 2005/0215540 A1 | 9/2005 | Marks et al. |
| 2005/0255546 A1 | 11/2005 | Nishikawa |
| 2005/0256199 A1 | 11/2005 | Durley et al. |
| 2005/0277649 A1 | 12/2005 | DeGraffenreid et al. |
| 2006/0011375 A1 | 1/2006 | Sugimoto et al. |
| 2006/0014768 A1 | 1/2006 | Kawasaki et al. |
| 2006/0026698 A1 | 2/2006 | Tomizuka et al. |
| 2006/0030565 A1 | 2/2006 | Shinkai et al. |
| 2006/0035882 A1 | 2/2006 | Koga et al. |
| 2006/0037093 A1 | 2/2006 | Tomizuka et al. |
| 2006/0041945 A1 | 2/2006 | Robl et al. |
| 2006/0059575 A1 | 3/2006 | Kusunoki et al. |
| 2006/0078992 A1 | 4/2006 | Misawa et al. |
| 2006/0084658 A1 | 4/2006 | Yamamoto et al. |
| 2006/0100195 A1 | 5/2006 | Maruyama et al. |
| 2006/0122181 A1 | 6/2006 | Ikemoto et al. |
| 2006/0123490 A1 | 6/2006 | Kakitani et al. |
| 2006/0135506 A1 | 6/2006 | Stephenson et al. |
| 2006/0167043 A1 | 7/2006 | Iwakubo et al. |
| 2006/0185025 A1 | 8/2006 | Oshimura et al. |
| 2006/0189603 A1 | 8/2006 | Garvey et al. |
| 2006/0194767 A1 | 8/2006 | Marks et al. |
| 2006/0205731 A1 | 9/2006 | Kodama et al. |
| 2006/0211717 A1 | 9/2006 | Sakai et al. |
| 2006/0217426 A1 | 9/2006 | Eto et al. |
| 2006/0223133 A1 | 10/2006 | Tamatani et al. |
| 2006/0233902 A1 | 10/2006 | Yajima et al. |
| 2006/0258701 A1 | 11/2006 | Mitsuya et al. |
| 2006/0270705 A1 | 11/2006 | Yonemori et al. |
| 2006/0293266 A1 | 12/2006 | Marks |
| 2007/0010571 A1 | 1/2007 | Garvey et al. |
| 2007/0010670 A1 | 1/2007 | Hirata et al. |
| 2007/0049572 A1 | 3/2007 | Marks et al. |

FOREIGN PATENT DOCUMENTS

| | | |
|---|---|---|
| EP | 1369129 | 12/2003 |
| EP | 1439221 A1 | 7/2004 |
| EP | 1447096 | 8/2004 |
| EP | 1743895 | 1/2007 |
| FR | 2709753 | 3/1995 |
| JP | 3093419 | 4/1991 |
| JP | 4230681 | 8/1992 |
| JP | 05271208 | 10/1993 |
| JP | 10045706 | 2/1998 |
| JP | 11199574 | 7/1999 |
| WO | WO-92/12148 | 7/1992 |
| WO | WO-92/19617 | 11/1992 |
| WO | WO-93/13082 | 7/1993 |
| WO | WO-94/11360 | 5/1994 |
| WO | WO-94/29286 | 12/1994 |
| WO | WO-96/08228 | 3/1996 |
| WO | WO-97/03986 | 2/1997 |
| WO | WO-97/17344 | 5/1997 |
| WO | WO-98/05657 | 2/1998 |
| WO | WO-98/45291 | 10/1998 |
| WO | WO-99/16758 | 4/1999 |
| WO | WO-99/26921 | 6/1999 |
| WO | WO-99/32115 | 7/1999 |
| WO | WO-01/00185 | 1/2001 |
| WO | WO-01/47510 | 7/2001 |
| WO | WO-02/08211 A1 | 1/2002 |
| WO | WO-02/014245 | 2/2002 |
| WO | WO-014246 | 2/2002 |
| WO | WO-02/051232 | 7/2002 |
| WO | WO-02/051838 | 7/2002 |
| WO | WO-02/053548 | 7/2002 |
| WO | WO-02/072145 | 9/2002 |
| WO | WO-03/034980 | 5/2003 |
| WO | WO-03/043655 | 5/2003 |
| WO | WO-04/022057 | 3/2004 |
| WO | WO-04/023030 | 3/2004 |
| WO | WO-04/042389 A2 | 5/2004 |
| WO | WO-04/080283 | 9/2004 |
| WO | WO-05/002518 | 1/2005 |
| WO | WO-05/037195 | 4/2005 |
| WO | WO-05/094457 | 10/2005 |
| WO | WO-05/105793 | 11/2005 |
| WO | WO-06/071603 | 7/2006 |
| WO | WO-06/101496 | 9/2006 |
| WO | WO-06/101497 | 9/2006 |
| WO | WO-07/024717 | 3/2007 |

OTHER PUBLICATIONS

Marks, A., J Mol Cell Cardiol. 2001, vol. vol. 33(4): pp. 615-624.*

Timerman et al. (J Biol Chem. 1993, vol. 268(31): pp. 22992-22999.*

Reiken et al. (2001). A novel excitation-contraction (EC) coupling myopathy in heart failure involving both cardiac and skeletal muscles. Circulation, (Oct. 23, 2001) vol. 104, No. 17 Supplement, pp. II.131.*

Reiken et al. (2002). Defective skeletal muscle calcium release channel function during heart failure. Circulation, vol. 106, No. 19 Supplement, pp. II-225.*

Ahern, C. A., Arikkath, J., Vallejo, P., Gurnett, C. A., Powers, P. A., Campbell, K. P. and Coronado, R. (2001). Intramembrane charge movements and excitation-contraction coupling expressed by two-domain fragments of the Ca 2+ channel. Proc Natl Acad Sci USA 98, 6935-40.

Ahern, G. P., Junankar, P. R., and Dulhunty, A. F. (1997). Subconductance states in single-channel activity of skeletal muscle ryanodine receptors after removal of FKBP12, Biophys J 72, 146-62.

Antos, C. L., Frey, N., Marx, S. O., Reiken, S., Gaburjakova, M., Richardson, J. A., Marks, A. R., and Olson, E. N. (2001). Dilated cardiomyopathy and sudden death resulting from constitutive activation of protein kinase A, Circ Res 89, 9971004.

Barbone, A., Holmes, J. W., Heerdt, P. M., The, A. H., Naka, Y., Joshi, N., Daines, M., Marks, A. R., Oz, M. C., and Burkhoff, D. (2001). Comparison of right and left ventricular responses to left ventricular assist device support in patients with severe heart failure: primary role of mechanical unloading underlying reverse remodeling, Circulation 104, 670-5.

Brillantes, A. B., Ondrias, K., Scott, A., Kobrinsky, E., Ondriasova, E., Moschella, M. C., Jayaraman, T., Landers, M., Ehrlich, B. E., and Marks, A. R. (1994). Stabilization of calcium release channel (ryanodine receptor) function by FK506-binding protein, Cell 77, 513-23.

Bristow, M. R., Gilbert, E. M., Abraham, W. T., Adams, K. F., Fowler, M. B., Hershberger, R. E., Kubo, S. H., Narahara, K. A., Ingersoll, H., Krueger, S., et al. (1996). Carvedilol produces dose-related improvements in left ventricular function and survival in subjects with chronic heart failure. MOCHA Investigators, Circulation 94, 2807-16.

Bristow, M. R., Ginsburg, R., Minobe, W., Cubicciotti, R. S., Sageman, W. S., Lurie, K., Billingham, M. E., Harrison, D. C., and Stinson, E. B. (1982). Decreased catecholamine sensitivity and beta-adrenergic-receptor density in failing human hearts, N Engl J Med 307, 205-211.

Cameron, A. M., Nucifora, F. C., Jr., Fung, E. T., Livingston, D. J., Aldape, R. A., Ross, C. A., and Snyder, S. H. (1997). FKBP12 binds the inositol 1,4,5-trisphosphate receptor at leucine-proline (1400-1401) and anchors calcineurin to this FK506-like domain, J Biol Chem 272, 27582-8 (N/A).

Chen, Y. G., Liu, F., and Massague, J. (1997). Mechanism of TGFbeta receptor inhibition by FKBP12, EMBO J 16, 3866-76.

Cheng, H., Song, L. S., Shirokova, N., Gonzalez, A., Lakatta, E. G., Rios, E., and Stern, M. D. (1999). Amplitude distribution of calcium sparks in confocal images: theory and studies with an automatic detection method, Biophys J 76, 60617.

Chidsey, C. A., Harrison, D. C. and Braunwald, E. (1962). Augmentation of plasma norepinephrine response to exercise in patients with congestive heart failure. New Engl J Med 267, 650.

Dietz, M. R., Chiasson, J. L., Soderling, T. R., and Exton, J. H. (1980). Epinephrine regulation of skeletal muscle glycogen metabolism. Studies utilizing the perfused rat hindlimb preparation, J Biol Chem 255, 2301-7.

Dodge, K. L., Khouangsathiene, S., Kapiloff, M. S., Mouton, R., Hill, E. V., Houslay, M. D., Langeberg, L. K. and Scott, J. D. (2001). mAKAP assembles a protein kinase A/PDE4 phosphodiesterase cAMP signaling module. EMBO J 20, 1921-30.

Doi, M., Yano, M., Kobayashi, S., Kohno, M., Tokuhisa, T., Okuda, S., Suetsugu, M., Hisamatsu, Y., Ohkusa, T., and Matsuzaki, M. (2002). Propranolol prevents the development of heart failure by restoring FKBP12.6-mediated stabilization of ryanodine receptor, Circulation 105, 1374-9.

Drexler, H., Banhardt, U., Meinertz, T., Wollschlager, H., Lehmann, M., and Just, H. (1989). Contrasting peripheral short-term and long-term effects of converting enzyme inhibition in patients with congestive heart failure. A double-blind, placebo-controlled trial, Circulation 79, 491-502.

Franzini-Armstrong, C., and Kish, J. W. (1995). Alternate disposition of tetrads in peripheral couplings of skeletal muscle, Journal of Muscle Research & Cell Motility 16, 319-24.

Gaburjakova, M., Gaburjakova, J., Reiken, S., Huang, F., Marx, S. O., Rosemblit, N., and Marks, A. R. (2001). FKBP12 binding modulates ryanodine receptor channel gating, J Biol Chem 276, 16931-5.

Gillo, B., Ma, Y. S. and Marks, A. R. (1993). Calcium entry during induced differentiation in Murine erythroleukemia 35 cells, Blood 81, 783-792.

Gonzalez, A., Kirsch, W. G., Shirokova, N., Pizarro, G., Brum, G., Pessah, I. N., Stem, M. D., Cheng, H., and Rios, E. (2000). Involvement of multiple intracellular release channels in calcium sparks of skeletal muscle, Proc Natl Acad Sci USA 97, 4380-4385.

Gullestad, L., Manhenka, C., Aarsland, T., Skardal, R., Fagertun, H., Wikstrand, J., and Kjekshus, J. (2001). Effect of metoprolol (CR/XL on exercise tolerance in chronic heart failure—a substudy to the MERIT-HF trial, Eur J Heart Fail 3, 463-8. (N/A).

Hain, J., Nath, S., Mayrleitner, M., Fleischer, S., and Schindler, H. (1994). Phosphorylation modulates the function of the calcium release channel of sarcoplasmic reticulum from skeletal muscle, Biophys J 67, 1823-33.

Harrington, D., and Coats, A. J. (1997). Mechanisms of exercise intolerance in congestive heart failure, Current 20 Opinion in Cardiology 12, 224-.

Jayaraman, T., Brillantes, A.-M. B., Timerman, A. P., Erdjument-Bromage, H., Fleischer, S., Tempst, P., and Marks, A. R. (1992). FK506 Binding Protein Associated with the Calcium Release Channel (Ryanodine Receptor), J Biol Chem 267, 9474-7.

Jayaraman, T., Ondrias, K., Ondriasova, E. and Marks, A. R. (1996). Regulation of the inositol 1,4,5-trisphosphate 30 receptor by tyrosine phosphorylation, Science 272, 1492-4.

Kaftan, E., Marks, A. R., and Ehrlich, B. E. (1996). Effects of rapamycin on ryanodine receptor/Ca (2+) -release channels from cardiac muscle, Circ Res 78, 990-7.

Katz, S. D., Bleiberg, B., Wexler, J., Bhargava, K., Steinberg, J. J., and LeJemtel, T. H. (1993). Lactate turnover at rest and during submaximal exercise in patients with heart failure, J Appl. Physiol 75, 1974-9.

Kirsch, W. G., Uttenweiler, D., and Fink, R. H. (2001). Spark-and ember-like elementary CaZ+ release events in skinned fibres of adult mammalian skeletal muscle, J Physiol 537, 379-89.

Klein, M. G., Lacampagne, A., and Schneider, M. F. (1997). Voltage dependence of the pattern and frequency of discrete Ca 2+ release events after brief repriming in frog skeletal muscle, Proc Natl Acad Sci USA 94, 11061-6.

Kukin, M. L., Kalman, J., Charney, R. H., Levy, D. K., Buchholz-Varley, C., Ocampo, O. N., and Eng, C. (1999). Prospective,' randomized comparison of effect of long-term treatment with metoprolol or carvedilol on symptoms, exercise, ejection fraction, and oxidative stress in heart failure, Circulation 99, 2645-51.

Lacampagne, A., Klein, M. G., and Schneider, M. F. (1998). Modulation of the frequency of spontaneous sarcoplasmic reticulum Ca 2+ release events (Ca 2+ sparks) by myoplasmic [Mg2+] in frog skeletal muscle. J Gen Physiol 111, 207-24.

Lai, F. A., Misra, M., Xu, L., Smith, H. A., and Meissner, G. (1989). The ryanodine receptor-Ca2+ release channel complex of skeletal muscle sarcoplasmic reticulum. Evidence for a cooperatively coupled, negatively charged homotetramer, J Biol Chem 264, 16776-85.

Lamb, G. D., and Stephenson, D. G. (1996). Effects of FK506 and rapamycin on excitation-contraction coupling in skeletal muscle 35 fibres of the rat. J Phys 494, 569-76.

Laver, D. R., and Lamb, G. D. (1998). Inactivation of Ca2+ release channels (ryanodine receptors RyRl and RyR2) with rapid steps in [Ca z+] and voltage, Biophys J 74, 2352-64.

Lunde, P. K., Dahlstedt, A. J., Bruton, J. D., Lannergren, J., Thoren, P., Sejersted, O. M., and Westerblad, H. (2001). Contraction and intracellular Ca t+ handling in isolated skeletal muscle of rats with congestive heart failure, Circ Res 88, 1299-305.

Lunde, P. K., Verburg, E., Eriksen, M., and Sejersted, O. M. (2002). Contractile properties of in situ perfused skeletal muscles from rats with congestive heart failure, J Physiol 540, 571-80.

MacFarlane, N. G., Darnley, G. M., and Smith, G. L. (2000). Cellular basis for contractile dysfunction in the diaphragm from a rabbit infarct model of heart failure, Am J Physiol Cell Physiol 278, C739-46.

Mancini, D. M., Walter, G., Reichek, N., Lenkinski, R., McCully, K. K., Mullen, J. L., and Wilson, J. R. (1992). Contribution of skeletal muscle atrophy to exercise intolerance and altered muscle metabolism in heart failure, Circulation 85, 1364-73.

Marks, A. R (1996) . Cellular functions of immunophilins, Physiol Rev 76, 631-49. (N/A.

Marks, A. R., Reiken, S., and Marx, S. O. (2002). Progression of heart failure: is protein kinase a hyperphosphorylation of the ryanodine receptor a contributing factor? Circulation 105, 272-5.

Marx, S. O., Ondrias, K., and Marks, A. R. (1998). Coupled gating between individual skeletal muscle Ca 2+ release channels (ryanodine receptors), Science 281, 818-21.

Marx, S. O., Reiken, S., Hisamatsu, Y., Gaburjakova, M., Gaburjakova, J., Yang, Y. M., Rosemblit, N., and Marks, A. R. (2001). Phosphorylation-dependent Regulation of Ryanodine Receptors. A novel role for leucine/isoleucine zippers, J Cell Biol 153, 699-708.

Marx, S. O., Reiken, S., Hisamatsu, Y., Jayaraman, T., Burkhoff, D., Rosemblit, N., and Marks, A. R. (2000). PKA Phosphorylation Dissociates FKTP12.6 from the Calcium Release Channel (Ryanodine Receptor): Defective Regulation in Failing Hearts. Cell 101, 365-76.

Meissner, G. (1994). Ryanodine receptor/Ca2+ release channels and their regulation by endogenous effectors, Annu Rev Physiol 56, 485-508 (N/A).

Minotti, J. R., Christoph, I., Oka, R., Weiner, M. W., Wells, L., and Massie, B. M. (1991). Impaired skeletal muscle function in patients with congestive heart failure. Relationship to systemic exercise performance, J Clin Invest 88, 2077-82.

Ono, K., Yano, M., Ohkusa, T., Kohno, M., Hisaoka, T., Tanigawa, T., Kobayashi, S., and Matsuzaki, M. (2000). Altered interaction of FKBP12.6 with ryanodine receptor as a cause of abnormal Ca (2+) release in heart failure, Cardiovasc Res 48, 323-31.

Perreault, C. L., Gonzalez-Serratos, H., Litwin, S E.,. Sun, X., Franzini-Armstrong, C., and Morgan, J. P. (1993). Alterations in contractility and intracellular Ca 2+ transients in isolated bundles of skeletal muscle fibers from rats with chronic heart failure, Circ Res 73, 405-12.

Reiken, S., Gaburjakova, M., Gaburjakova, J., He, K. L., Prieto, A., Becker, E., Yi, G. H., Wang, J., Burkhoff, D., and Marks, A. R. (2001). Beta-adrenergic receptor blockers restore cardiac calcium release channel (ryanodine receptor) structure and function in heart failure, Circulation 104, 2843-8.

Rios, E., and Brum, G. (1987). Involvement of dihydropyridine receptors in excitation-contraction coupling in skeletal 15 muscle. Nature 325, 717-20.

Rios, E., Pizarro, G. and Stefani, E. (1992). Charge movement and the nature of signal transduction in skeletal muscle excitation-contraction coupling. Annu Rev Physiol 54, 109-33.

Schneider, M. F., and Chandler, W. K. (1973). Voltage dependent charge movement in skeletal muscle, a possible step in excitation-contraction coupling, Nature 242, 244-6.

Schoenmakers, T. J., Visser, G. J., Flik, G. and Theuvenet, A. P. (1992). CHELATOR: an improved method for computing metal ion concentrations in physiological solutions. Biotechniques 12, 870-4, 876-9.

Semserian, C., Ahmad, I., Giewat, M., Georgakopoulos, D., Schmitt, J. P., McConnell, B. K., Reiken, S., Mende, U., Marks, A. R., Kass, D. A., et al. (2002). The L-type calcium channel inhibitor ditiazem prevents cardiomyopathy in a mouse model, J Clin Invest 109, 1013-20.

Shirokova, N., Garcia, J. and Rios, E. (1998). Local calcium release in mammalian skeletal muscle. J Physiol 512, 377-84.

Shou, W., Aghdasi, B., Armstrong, D. L., Guo, Q., Bao, S., Charng, M. J., Mathews, L. M., Schneider, M. D., Hamilton, S. L., and Matzuk, M. M. (1998). Cardiac defects and altered ryanodine receptor function in mice lacking FKBP12, Nature 391, 489-92.

Sonnleitner, A., Fleischer, S., and Schindler, H. (1997). Gating of the skeletal calcium release channel by ATP is inhibited by protein phosphatase 1 but not by Mgt+, Cell Calcium 21, 283-90.

Sorensen; V.B., Wroblewski, H., Galatius, S., Haunso, S., and Kestrup, J. (1999) . Exercise blood flow and microvascualr distensibility in skeletal muscle normalize after heart transplantation, Clin Transplant 13, 410-9.

Stratton, J. R., Kemp, G. J., Daly, R. C., Yacoub, M., and Rajagopalan, B. (1994). Effects of cardiac transplantation on bioenergetic abnormalities of skeletal muscle in congestive heart failure, Circulation 89, 1624-31.

Suko, J., Maurer-Fogy, I., Plank, B., Bertel, O., Wyskovsky, W., Hohenegger, M. and Hellmann, G. (1993). Phosphorylation of serine 2843 in ryanodine receptor-calcium release channel of skeletal muscle by cAMP-, cGMP- and CaM-dependent protein kinase. Bioch Biophys Acta 1175, 193-206.

Sullivan, M. J., and Hawthorne, M. H. (1995). Exercise intolerance in patients with chronic heart failure, Prog Cardiovasc Dis 38, 1-22.

Tanabe, T., Beam, K. G., Adams, B. A., Niidome, T. and Numa, S. (1990) . Regions of the skeletal muscle dihydropyridine receptor critical for excitation-contraction coupling. Nature 346, 567-69.

Wang, J., Yi, G. H., Knecht, M., Cai, B. L., Poposkis, S., Packer, M., and Burkhoff, D. (1997). Physical training alters the pathogenesis of pacing-induced heart failure through endothelium-mediated mechanisms in awake dogs, Circulation 96, 2683-92.

Wilson, J. R. (1995). Exercise intolerance in heart failure. Importance of skeletal muscle, Circulation 91, 559-61.

Wilson, J. R., Mancini, D. M., and Dunkman, W. B. (1993). 15 Exertional fatigue due to skeletal muscle dysfunction in patients with heart failure, Circulation 87, 470-5.

Yano, M., Kobayashi, S., Kohno, M., Doi, M., Tokuhisa, T., Okuda, S., Suetsugu, M., Hisaoka, T., Obayashi, M., Ohkusa, T., Kohno, M. and Matsuzaki, M. (2003). FKBP12.6-mediated stabilization of calcium-release channel (ryanodine receptor) as a novel therapeutic strategy against heart failure. Circulation 107, 477-84.

Yano, M., Ono, K., Ohkusa, T., Suetsugu, M., Kohno, M., Hisaoka, T., Kobayashi, S., Hisamatsu, Y., Yamamoto, T., Noguchi, N., et al. (2000). Altered stoichiometry of FKBP12.6 versus ryanodine receptor as a cause of abnormal Ca(2+) leak through ryanodine receptor in heart failure, Circulation 102, 2131-6.

U.S. Appl. No. 10/763,498, filed Jan. 22, 2004, Marks et al.

Ackerman, MJ, "Cardiac channelopathies: it's in the genes," Nat. Med., vol. 10, pp. 463-4 (2004).

Ahmmed, G.U. et al., "Changes in Ca(2+) Cycling Proteins Underlie Cardiac Action Potential Prolongation in a Pressure-Overloaded Guinea Pig Model with Cardiac Hypertrophy and Failure." Circ. Res., vol. 86, No. 5, pp. 558-570. (2000).

Alvarez et al., "Late Post Myocardial Infarcation Induces a Tetrodotoxin-Resistant Na+ Current in Rat Cardiomyocytes." J. Mol. Cell Cardiol, vol. 32, pp. 1169-1179. (2000).

Baillie, et al., "beta -Arrestin-mediated PDE4 cAMP phosphodiesterase recruitment regulates beta-adrenoceptor switching from Gs to Gi," Proc. Natl. Acada. Sci. USA 100, 940-945 (2003).

Bangur, et al., "Mutational analysis of the D1/E1 core helices and the conserved N-terminal region of yeast transcription factor IIB (TFIIB): identification of an N-terminal mutant that stabilizes TATA-binding protein-TFIIB-DNA complexes," Mol. Cell Biol., vol. 17, pp. 6784-93 (1997).

Barnes, P.J., "Theophylline: new perspectives for an old drug," Am. J. Respir. Crit. Care Med. 167, 813-8 (2003).

Basso, C. et al., "Arrhythmogenic Right Ventricular Cardiomyopathy Causing Sudden Cardiac Death in Boxer Dogs: A New Animal Model of Human Disease." Circulation, vol. 109, No. 9, pp. 1180-1185. (2004).

Behr, et al., "Cardiological assessment of first-degree relatives in sudden arrhythmic death syndrome," The Lancet, vol. 362, 1457-59 (2003).

Bennett et al. "The Pattern of Onset and Spontaneous Cessation of Atrial Fibrillation in Man." Circulation, vol. 41, pp. 981-988. (1970).

Bennett et al., "Synthesis of 2-methoxydibenzo [b,f](1,4)-thiazepin-11 (10H)-one 5,5-dioxide." Organic Preparations and Procedures International, vol. 6, No. 6, pp. 287-293. (1974).

Bennett, J.A. et al. "Identification and Characterization of the Murine FK506 Binding Protein (FKBP) 12.6 gene." Mamm. Genome, vol. 9, pp. 1069-1074. (1998).

Beuckelmann, D. et al. "Intracellular Calcium Handling in Isolated Ventricular Myocytes from Patients with Terminal Heart Failure." Circulation vol. 85, pp. 1046-1055 (1992).

Bezprozvanny, I. et al. "Bell-shaped Calcium Response Curves of Ins (1,4,5) P3- and Calcium-oated Channels from Endoplasic Reticulum of Cerebellum." Nature. vol. 351, pp. 751-754.

Bittar, et al., "The arrhythmogeneicity of theophylline. A multivariate analysis of clinical determinants," Chest 99, 1415-1420 (1991).

Bohm, M. et al. "cAMP Concentrations, cAMP Dependent Protein Kinase Activity, and Phospholamban in Non-Failing and Failing Myocardium." Cardivasc. Res., vol. 28, No. 11, pp. 1713-1719. (1994).

Bolger, et al., "Characterization of five different proteins produced by alternatively spliced mRNAs from the human cAMP-specific phosphodiesterase PDE4D gene," Biochem. J. 328 (Pt 2), 539-48 (1997).

Boyden et al., "2APB- and JTV519 (K201) - Sensitive Micro Ca 2+ Waves in Arrhythmogenic Purkinje Cells that Survive in Infarcted Canine Heart." Heart Rhythm, vol. 1, pp. 218-226. (2004).

Brillantes, et al., "Developmental and tissue-specific regulation of rabbit skeletal and cardiac muscle calcium channels involved in excitation-contraction coupline," Circ. Res., vol. 75, pp. 503-10 (1994).

Brillantes, et al., "Differences in cardiac calcium release channel (ryanodine receptor) expression in myocardium from patients with end-state heart failure caused by ischemic versus dilated cardiomyopathy," Circ. Res., vol. 71, pp. 18-26 (1992).

Bristow, et al., "Beta 1 - and beta 2-adrenergic-receptor subpopulations in nonfailing and failing human ventricular myocardium: coupling of both receptor subtypes to muscle contraction and selective beta 1-receptor down-regulation in heart failure," Circulation Research, vol. 59, No. 3, pp. 297-309. (1986).

Bristow, Michael R. et al. "Beta-Adrenergic Neuroeffector Abnormalities in the Failing Human Heart are Produced by Local Rather Than Systemic Mechanisms." J. Clin. Invest., vol. 89, pp. 803-815 (Mar. 1982).

Burashnikov et al. "Reinduction of Atrial Fibrillation Immediately After Termination of the Arrhythmia is Mediated by Late Phase 3 Early Afterdepolarization-Induced Triggered Activity." Circulation, vol. 107, pp. 2355-2360. (2003).

Callaway, C. et al., "Localization of the High and Low Affinity [3H] Ryanodine Binding Sites on the Skeletal Muscle Ca2+ Release Channel." The Journal of Biological Chemistry, vol. 269, No. 22, pp. 15876-15884. (1994).

Carlisle Michel, et al., "PKA-phosphorylation of PDE4D3 facilitates recruitment of the mAKAP signaling complex," Biochem. J., vol. 381, pp. 587-592 (2004).

Catsoulacos, "Synthesis of Substituted Dihydrobenzothiazepines and Related Compounds." J Heterocyclic Chemistry, vol. 7, No. 2: pp. 409-411. (1970).

Cerrone, M. et al., "Bidirectional Ventricular Tachycardia and Fibrillation Elicited in a Knock-in Mouse Model Carrier of a Mutation in the Cardiac Ryanodine Receptor." Circ. Res., vol. 96, pp. e77-82. (2005).

Chatrath, et al., "Beta-blocker therapy failures ins symptomatic probands with genotyped long-QT syndrome," Pediatr. Cardiol., vol. 25, pp. 459-65 (2004).

Che, et al., "Reversal of P-glycoprotein mediated multidrug resistance by a newly synthesized 1,4-benzothiazipine derivative, JTV-519," Cancer Lett., vol. 187, pp. 111-9 (2002).

Choi, et al., "Spectrum and frequency of cardiac channel defects in swimming-triggered arrhythmia syndromes," Circulation, vol. 110, pp. 2119-24 (2004).

Choi, et al., "Sudden cardiac death and channelopathies: a review of implantable defibrillator therapy," Pediatr. Clin. North Am., vol. 51, pp. 1289-1303 (2004).

Chugh et al. "Epidermiology and Natural History of Atrial Fibrillation: Clinical Implications." J. Am. Coll. Cardiol., vol. 37, No.2, pp. 371-378. (2001).

CIBIS-II. The Cardiac. Insufficiency Bisoproloi Study II (CIBIS-II): A Randomized Trial. The Lancet, vol. 353, pp. 9-13, (1999).

Cohn, J.N. et al. "Plasma Norepinephrine as a Guide to Prognosis in Patients with Chronic Congestive Heart Failure." N. Eng. J. Med., vol. 311, No. 13, pp. 819-823 (1984).

Conti, et al., "Cyclic AMP-specific PDE4 phosphodiesterases as critical components of cyclic AMP signaling," J. Biol. Chem., vol. 278, No. 8, pp. 5493-5496. (2003).

Cranefield, P.F. "Action Potentials, Afterpotentials and Arrhythmias." Circ. Res., vol. 41, No. 4, pp. 415-423. (1977).

Culligan, et al., "Drastic reduction of calsequestrin-like proteins and impaired calcium binding in dystrophic mdx muscle," J. Appl. Physiol., vol. 92, pp. 435-455 (2002).

Daoud et al. "Effect of Verapamil and Porcainamide on Atrial Fibrillation-Induced Electrical Remodeling in Humans." Circulation, vol. 96, pp. 1542-1550. (1997).

Dorian, P., "Antiarrhythmic action of beta-blockers: potential mechanisms," J. Cardiovasc. Pharmacol. Therapeut., vol. 10, pp. S15-S22 (2005).

Dun et al. "Chronic Atrial Fibrillation Does Not Further Decrease Outward Currents. It Increases Them." Am. J. Physiol. Heart Circ. Physiol., vol. 285, pp. H1378-1384. (2003).

Echt et al., "Mortality and morbidity in patients receiving encainide, flecainide, or placebo," The Cardiac Arrhythmia Suppression Trial, N. Engl. J. Med., vol. 324, pp. 781-788. (1991).

Eichhorn et al. "Medical Therapy can Improve the Biological Properties of the Chronically Failing Heart. A New, Era in the Treatment of Heart Failure." Circulation, vol. 94, pp. 2285-2296. (1996).

Elvan et al. "Pacing-induced Chronic Atrial Fibrillation Impairs Sinus Node Function in Dogs: Electrophysiological Remodeling." Circulation, vol. 94, pp. 2953-2960. (1996).

Exhibit A: Chemical Structures.

Fabiato, A. "Calcium-induced Release of Calcium from the Cardiac Sarcoplasmic Reticulm." Am. J. Physiol., vol. 245, pp. C1-C14. (1983).

Falk, R.H. "Atrial Fibrillation." N. Engl. J. Med., vol. 344, No. 14, pp. 1067-1078. (2001).

Farr, et al., "Sparking the failing heart," N. Engl. J. Med., vol. 351, pp. 185-7 (2004).

Feldman, et al., "Deficient production of cyclic AMP: pharmacologic evidence of an important cause of contractile dysfunction in patients with end-stage heart failure," Circulation, vol. 75, No. 2, pp. 331-339 (1987).

Fisher, J.D. et al. "Familial Polymorphic Ventricular Arrhythmias: A Quarter Century of Successful Medical Treatment Based on Serial Exercise-Pharmacologic Testing." J. Am. Coll. Cardiol., vol. 34, No. 7, pp. 2015-2022. (1999).

Fitzgerald, et al., "reduced ryanodine receptor content in isolated neonatal cardiomyocytes compared with the intact tissue," J. Mol. Cell, Cardiol., vol. 26, pp. 1261-5 (1994).

Fodor et al. "New Convenient Synthesis of 1,4-benzothiazepines." Tetrahedron Letters, vol. 36, No. 5, pp. 753-756. (1995).

Fox, P.R., "Spontaneously Occurring Arrhythmogenic Right Ventricular Cardiomyopathy in the Domestic Cat: A New Animal Model Similar to the Human Disease." Circulation, vol. 102, No. 15, pp. 1863-1870. (2000).

Fozzard, H.A. "Afterdepolarizations and triggered activity." Basic Res. Cardiol., vol. 87, pp. 105-113. (1992).

Franzen P. et al. "Cloning of TGFbeta Type 1 Receptor That Forms a Heteromeric Complex with the TGF beta type II receptor." Cell, vol. 75, pp. 681-692. (1993).

Fraser, I.D. et al. "Modulation of Ion channels: a "Current" view of AKAPs." Neuron, vol. 23, pp. 423-426. (1999).

Frazier, O.H. et al. "First Use of an Untethered, Vented Electric Left Ventricular Assist Device for Long-Term Supprt." Circulation, vol. 89, pp. 2908-2914. (1994).

Gaspo et al. "Functional Mechanism Underlying Tachycardia-induced Sustained Atrial Fibrillation in a Chronic Dog Model." Circulation, vol. 96, pp. 4027-4035. (1997).

Giembycz, M.A., "Development status of second generation PDE4 inhibitors for asthma and COPD: the story so far," Monaldi, Arch. Chest Dis., vol. 57, pp. 48-64. (2002).

Gillian, et al., "Analysis of expression of the human ryanodine receptor gene in malignant hyperthermia skeletal muscle tissue," Biochem. Soc. Trans., vol. 19, pp. 46S (1991).

Go, Loewe O. et al., "Differential Regulation of Two Types of Intracellular Calcium Release Channels during End-Stage Heart Failure." J. Clin. Invest., vol. 95, pp. 888-894. (Feb. 1995).

Goette et al. "Electrical Remodeling in Atrial Fibrillation: Time Course and Mechanisms." Circulation, vol. 94, pp. 2968-2974. (1996).

Gomez, A.M. et al. "Defective Excitation-Contraction Coupling in Experimental Cardiac Hypertrophy and Heart Failure." Science, vol. 276, pp. 800-806. (May 2, 1997).

Gong, et al., "Persistent improvement in synaptic and cognitive functions in an Alzheimer mouse model after rolipram treatment," J. Clin. Invest., vol. 114, pp. 1624-1634. (2004).

Gretarsdottir et al., "The gene encoding phosphodiesterase 4D confers risk of ischemic stroke," Nat. Genet., vol. 35, pp. 131-8. (2003).

Gwathmey et al. "Abnormal Intracellular Calcium Handling in Myocardium From Patients with End-Stage Heart Failure." Cir. Res., vol. 61, pp. 70-76. (1987).

Hachida et al. "Protective effect of JTV519 on Prolonged Myocardial Preservation." Transplant Proc., vol. 31, p. 1094. (1999).

Hachida et al. "Significant Effect of 1,4-Benzothiazepine Derivative (K2) in Improving Myocardial Preservation." Transplantation Proceedings, vol. 29, pp. 1346-1348. (1997).

Hachida, et al., "Protective Effect of JTV519 (K201), a New 1, 4 - Benzothiazepine Derivative, on Prolonged Myocardia Preservation." Transplantation Proceedings, vol. 31, pp. 996-1000. (1999).

Hachida, M. et al. "Protective Effect of JT-519, a new 1, 4-Benzothiazepine Derivative, on Prolonged Myocardial Preservation." J. Card. Surg., vol. 14, pp. 187-193. (1999).

Hain, J. et al., "Phosphorylation Modulates the Function of the Calcium Release Channel of Sarcoplasmic Reticulum from Skeletal Muscle." Biophys. J., vol. 67, pp. 1823-1833. (1994).

Hara et al., "Steady-state and nonsteady State Action Potentials in Fibrillating Canine Atrium: Abnormal Rate Adaption and Its Possible Mechanisms." Cardiovasc. Res., vol. 42, pp. 455-469. (1999).

Harnick, D.J. et al. "The Human Type 1 Inositol 1,4, 5-trisphosphate receptor from T Lymphocytes: Structure, Localization, and Tyrosine Phosphorylation." J. Biol. Chem., vol. 270, No. 6, pp. 2833-2840. (1995.).

Hasenfuss et al., "Treatment of Heart Failure Through Stabilization of the Cardiac Ryanodine Receptor." Circulation, vol. 107, pp. 378-380. (2003).

Haut, Donahue, et al., "Annexin V Disruption Impairs Mechanically Induced Calcium Signaling in Osteoblastic Cells," Bone, vol. 35, No. 3) pp. 656-63, (2004).

Houslay, et al., "PDE4 cAMP phosphodiesterases: modular enzymes that orchestrate signaling cross-talk, desensitization and compartmentalization," Biochem. J., vol. 370, pp. 1-18. (2003).

Huse, M. et al. "Crystal Structure of the Cytoplasmic Domain of the Type 1 TGFbeta Receptor in Complex With FKBP12." Cell, vol. 96, pp. 425-436. (1999).

Ikemoto, et al., "Regulation of calcium release by interdomain interaction within ryanodine receptors," Front Biosci., vol. 7, pp. d671-683 (2002).

Inagaki et al. "Anti-ischemic Effect of a Novel Cardioprotective Agent. JTV 519. is mediated through Specific Activation of d-Isoform of Protein Kinase C in Rat Ventricular Myocardium." Circulation, vol. 101, pp. 797-804. (2000).

Inagaki et al., "The Cardioprotective Effects of a new 1,4-benzothiazepine Derivative, JTV 519, on ischemia/reperfusion-induced Ca2+ Overload in Isolated Rat Hearts." Cardiovasc Drugs Ther., vol. 14, pp. 489-495. (2000).

International Search Report and Written Opinion from PCT/US04/20474, Aug. 30, 2005.

International Search Report and Written Opinion from PCT/US04/32550 Oct. 18, 2005.

InternationalSearch Report and Written Opinion from PCT/US05/009495, Mar. 14, 2006.

International Search Report and Written Opinion from PCT/US05/10055, Oct. 27, 2005.

International Search Report and Written Opinion from PCT/US05/49514, Aug. 31, 2006.

Ishii, et al., "JTV-519, a new cardioprotective drug, and cariporide, synergistically improved post-ischemic contractile recovery in rat," Journal of Molecular and Cellular Cardiology, vol. 35, Issue 6, p. A29 (2002).

Isselbacher, Kurt J. et al. "Harrison's Principles of Internal Medicine." 13th Edition, vol. 1, pp. 1022-1024. (1994).

Ito et al. "JTV-519, a Novel Cardioprotective Agent, Improves the Contractile Recovery after Ischaemia Reperfusion in Coronary Perfused Guinea Pig Ventricular Muscles." Br. J. Pharmacol., vol. 130, No. 4, pp. 767-776. (2000).

Jiang et al., "Abnormal Ca2+ Release, but Normal Ryanodine Receptors, in Canine and Human Heart Failure." Circulation Research, vol. 91, pp. 1015-1022. (Nov. 29, 2002).

Jiang, D. et al. "Enhanced Basal Activity of a Cardiac Ca2+ Release Channel (Ryanodine Receptor) Mutant Associated with Ventricular Tachycardia and Sudden Death." Circ. Res., vol. 91, pp. 218-225. (2002).

Jin, et al., "Impaired growth and fertility of cAMP-specific phosphodiesterase PDE4D-deficient mice," Proc. Natl. Acad. Sci. USA 96, pp. 11998-12003. (1999).

Kaneko et al., "Crystal Structure of Annexin V with its Ligand K-201 as a Calcium Channel Activity Inhibitor." Journal of Molecular Biology, vol. 274, pp. 16-20. (1997).

Kaneko et al., "Inhibition of Annexin V-dependent Ca2 Movement in Large Unilamellar Vesicles by K201, A New 1,4 benzothiazepine derivative," Biochimica et Biophysica Acta, vol. 1330, pp. 1-7. (1997).

Kaneko, N. "New 1,4-benzothiazepine Derivative, K201, Demonstrates Cardioprotective Effects Against Sudden Cardiac Cell Death and Intracellular Calcium Blocking Action." Drug Dev. Res., Vol. 33: pp. 429-438 (1994).

Kapiloff, M.S. et al. "mAKAP:an A-kinase Anchoring Protein Targeted to the Nuclear membrane of differentiated Myocytes." J. Cell Sci., vol. 112, pp. 2725-2736. (1999).

Kapiloff, M.S. et al., "mAKAP and the ryanodine receptor are part of a multi-component signaling complex on the cardiomyocyte nuclear envelope," Journal of Cell Science, vol. 114, pp. 3167-3176 (2001).

Katritzky, et al., "1H and 13C NMR study of tetrahydro-1, 4-benzothiazepine conformations," J. Chem. Soc. 5, pp. 1816-1822 (2002).

Katritzky, et al., "Convenient syntheses of 2, 3, 4, 5-tetrahydro-1, 4-benzothiazepines, -1, 4-benzoxazepines and -1, 4-benzodiazepines." J. Chem. Soc. 11, Perkin Trans. I, pp. 592-598 (2002).

Kawabata et al. "Effect of a Novel Cardioprotective Agent, JTV-519, on Metabolism, Contraction and Relaxation in the Ischemia-Reperfused Rabbit Heart." Jpn Circ. J., vol. 64, pp. 772-776. (2000).

Kawabata, et al., "A novel cardioprotective agent, JTV-519, is abolished by nitric oxide synthase inhibitor on mycardial metabolism in ischemia-reperfused rabbit hearts." Hypertens Res., vol. 25, pp. 303-309 (2002).

Kimura, J. et al. "Effects of a Novel Cardioprotective Drug, JTV-519 on Membrane Currents of Guinea Pig Ventricular Myocytes." Jpn. J. Pharmacol., vol. 79, pp. 275-281. (1999).

Kirchhefer, U. et al. "Activity of cAMP-dependent Protein Kinase and Ca2+/calmodulin-dependent Protein Kinase in Failing and Nonfailing Human Hearts." Cardiovasc. Res., vol. 42, pp. 254-261 (1999).

Kiriyama et al. "Effects of JTV-519, a Novel Anti-Ischaemic Drug, on the Delayed Rectificer K+ Current in Guinea-Pig Ventricular Myocytes." Naunyn Schmiedebergs Arch Pharmacol. vol. 361, No. 6, pp. 646-653. (2000).

Kirsch, et al., "The roles of annexins and types II and X Collagen in matrix vesicle-mediated mineralization of growth plate cartilage," J. Biol. Chem., vol. 275, pp. 35577-83 (2000).

Kiryu, K. et al. "Pathologic and Electrocardiographic Findings in Sudden Cardiac Death in Racehorses." J. Vet. Med. Sci., vol. 61, No., 8, pp. 921-928. (1999).

Kittleson, M.D. et al., "Familial Hypertrophic Cardiomyopathy in Maine Coon Cats: An Animal Model of Human Disease." Circulation, vol. 99, No. 24, pp. 3172-3180. (1999).

Kneller et al. "Remodeling of Ca2+ - handling by Atrial Tachycardia: Evidence for a Role in Loss of Rate-Adaption." Cardiovasc. Res., vol. 54., pp. 416-426. (2002).

Kobrinsky, et al., "Expressed ryanodine receptor can substitute for the inositol 1,4,5-trisphosphate receptor in Xenopus laevis oocytes during progesterone-induced maturation," Dev. Biol., vol. 172, pp. 531-40 (1995).

Kohno et al., "A New Cardioprotective Agent, JTV-519, Improves Defective Channel Gating of Ryanodine Receptor in Heart Failure." Am. J. Physiol Heart Circ. Physiol., vol. 284, No. 3, pp. H1035-H1042. First published Nov. 14, 2002. (Mar. 2003).

Kumagai et al. "Antiarrhythmic Effects of JTV-519, a novel Cardioprotective Drug, on Atrial Fibrillation/Flutter in a Canine Sterile Pericarditis Model." J. Cardiovasc. Electrophysiol. vol. 14, No. 8, pp. 880-884. (2003).

Laflamme, M.A. et al. "Gs and Adenylyl Cyclase in Transverse Tubules of Heart: Implications for cAMP-dependent signaling." Am. J. Phys., vol. 277, pp. H1841-H1848. (1999).

Laitinen, P.J. et al. "Mutations of the Cardiac Ryanodine Receptor (RyR2) Gene in Familial Polymorphic Ventricular Tachycardia." Circulation, vol. 103, pp. 485-490. (2001).

Lauffenburger et al., "Receptors." Oxford University Press, Chapter, 2, pp. 9-12. (1996).

Lee, et al., "Sudden unexplained death: evaluation of those left behind," The Lancet, vol. 362, pp. 1429-1431 (2003).

Leenhardt, A. et al. "Catecholaminergic Polymorphic Ventricular Tachycardia in Children: a 7-year follow-up of 21 patients." Circulation, vol. 91, pp. 1512-1519. (1995).

Lehnart, et al., "Immunophilins and coupled gating of ryanodine receptors," Curr. Top. Med. Chem., vol. 3, pp. 1383-91 (2003).

Lehnart et al. "Cardiac Ryanodine Receptor Function and Regulation in Heart Disease." Ann NY Acad Sci., vol. 1015, pp. 144-159. (2004).

Lehnart et al. "Defective Ryanodine Receptor Interdomain Interactions May Contribute to Intracellular Ca2+ Leak: A Novel Therapeutic Target in Heart Failure." Circulation, vol. 111, No. 25, pp. 3342-3346. (2005).

Lehnart et al., "Phosphodiesterase 4D Deficiency in the Ryanodine-Receptor Complex Promotes Heart Failure and Arrhythmias." Cell, vol. 123, No. 1, pp. 25-35. (Oct. 7, 2005).

Lehnart et al., "Sudden Death in Familial Polymorphic Ventricular Tachycardia Associated with Calcium Release channel (Ryanodine Receptor) Leak." Circulation, vol. 109, pp. 3208-3214. (2004).

Lehnart, et al., "Calstabin deficiency, ryanodine receptors, and sudden cardiac death." Biochem. Biophys. Res. Commun., vol. 322, pp. 1267-79 (2004).

Leistad et al. "Atrial Contractile Dysfunction After Short-Term Atrial Fibrillation is Reduced by Verapamil But Increased by BAY K8644." Circulation, vol. 93, pp. 1747-1754. (1996).

Lesh, et al., "Anti-ryanodine receptor antibody binding sites in vascular and endocardial endothelium," Cir., Res., vol. 72, pp. 481-8 (1993).

Levin, H.R. et al. "Reversal of Chronic Ventricular Dilation in Patients with End-Stage Cardiomyopathy by Prolonged Mechanical Unloading." Circulation, vol. 91, pp. 2717-2720.

Levy et al. "Long-Term Trends in the Incidence of the Survival with Heart Failure." N. Engl. J. Med., vol. 347, No. 18, pp. 1397-1402. (2002).

Lisy et al., "New Cardioprotective Agent K201 is Natriuretic and Glomerular Filtration Rate Enhancing." Circulation, vol. 113, pp. 246-251. (2006).

Lorenz, M.C. et al. "TOR Mutations Confer Rapamycin Resistance by Preventing Interaction with FKBP12-Rapamycin." J. Biol. Chem., vol. 270, No. 46, pp. 27531-27537. (1995).

MacDougall, L.K. et al. "Identification of the Major Protein Phosphatases in Mammalian Cardiac Muscle Which Dephosphorylate Phospholamban." Eur. J. Biochem., vol. 196, pp. 725-734. (1991).

Manzur, et al., "A severe clinical and pathological variant of central core disease with possible autosomal recessive inheritance," Neur. Disorders. vol. 8, pp. 467-473 (1998).

Marban, E. et al. "Mechanisms of Arrhythmogenic Delayed and Early Afterpolarizations in Ferret Ventricular Muscle." J. Clin. Invest., vol. 78, pp. 1185-1192. (1986).

Marks et al. "Clinical Implications of Cardiac Ryanodine Receptor/Calcium Release Channel Mutation Linked to Sudden Cardiac Death." Circulation, vol. 106, pp. 8-10. (Jul. 2, 2002).

Marks et al. "Involvement of the Cardiac Ryanodine Receptor/Calcium Release Channel in Catecholaminergic Polymorphic Ventricular Tachycardia." J. Cell. Physiol., vol. 190, pp. 1-6. First published Oct. 26, 2001 (2002).

Marks et al. "Ryanodine Receptors, FKBP12, and Heart Failure." Frontiers in Bioscience, vol. 7, pp. 970-977. (2002).

Marks et al., "A Guide for the Perplexed: Towards an Understanding of the Molecular Basis of Heart Failure." Circulation. vol. 107, pp. 1456-1459. (2003).

Marks, A.R. "Cardiac intracellular Calcium Release Channels: Role in Heart Failure." circ. Res., vol. 87, pp. 8-11. (2000).

Marks, AR, "Arrhythmias of the hear: beyond ion channels," Nat. Medicine, vol. 9, pp. 263-4, (2003).

Marks, AR, "Calcium and the hear: a question of life and death," J. Clin. Investigation, vol. 111, pp. 597-600. (2003).

Marks, AR, "Calcium channels expressed in vascular smooth muscle," Circulation, vol. 86, pp. 11161-7 (1992).

Marks, AR, "Immunophilin modulation of calcium channel gating," Methods., vol. 9, pp. 177-87 (1996).

Marks, AR, "Intracellular calcium-release channels: regulators of cell life and death," Am. J. Phsiol., vol. 272, pp. H597-605 (1997).

Marks, et al., "Molecular cloning and characterization of the Ryanodine receptor/junctional channel complex cDNA from skeletal muscle sarcoplasmic reticulum," Proc. Natl. Acad. Sci. U.S.A., vol 86, pp. 8683-7 (1989).

Marks, et al., "Regulation of ryanodine receptors via macromolecular complexes: a novel role for leucine/isoleucine zippers," Tends Cardiovasc. Med., vol. 12, pp. 166-70 (2002).

Marks, et al., "Surface topography analysis of the ryanodine receptor/junctional channel complex based on proteolysis sensitivity mapping," J. Biol. Chem., vol. 265, pp. 13143-9 (1990).

Marks, et al., "The ryanodine receptor/junctional channel complex is regulated by growth factors in a myogenic cell line," J. Cell. Biol., vol. 114, pp. 303-12, (1991).

Maron, et al., "Recommendations for physical activity and recreational sports participation for young patients with genetic cardiovascular diseases," Circulation, vol. 109, pp. 2807-16 (2004).

Marx et al. "Requirement of a Macromolecular signaling complex for Beta-Adrenergic Receptor Modulation of the KCNQ1/KCNE1 Potassium Channel," Science, vol. 295, pp. 496-499. (2002).

Marx et al., "Coupled Gating Between Cardiac Calcium Release Channels (Ryanodine Receptors)" Circ. Res., vol. 88, pp. 1151-1158. (2001).

Marx S.O et al., "Regulation of the Ryanodine Receptor in Heart Failure." Basic Res. Cardiol., vol. 97, suppl. 1, pp. 1/49-1/51. (2002).

Masumiya et al., "Localization of the 12.6 kDa FK506-biding Protein (FKBP12.6) Binding Site to the NH2- Terminal Domain of the Cardiac Ca2+ Release Channel. (Ryanodine Receptor)." The Journal of Biological Chemistry, vol. 278, pp. 3786-3792. (2003).

McCartney, S. et al. "Cloning and Characterization of A-Kinase Anchor Protein 100 (AKAP100). A Protein That Targets A-Kinase to the Sarcoplasmic Reticulim." J. Biol. Chem., vol. 270, No. 16, pp. 9227-9333. (1995).

McPhie, et al., " Structure of the hormone binding domain of human beta 1 thyroid hormone nuclear receptor: is is an alpha/beta barrel?" Biochemistry, vol. 32, pp. 7460-5 (1993).

MERIT-HF Study Group. "Effect of Metoprotlol CR/XL in Chronic Heart Failure: Metoprolol CR/XL Randomised Intervention Trail in Congestive Heart Failure (MERIT-HF)," The Lancet, vol. 353, pp. 2001-2007. (Jun. 12, 1999).

Meurs, K.M. et al., "A Cardiac Myosin Binding Protein C Mutation in the Maine Coon Cat with Familial Hypertrophic Cardiomyopathy." Hum Mol Genet, vol. 14, No. 23, pp. 3587-3593. (2005).

Meurs, KM. "Boxer Dog Cardiomyopathy: An Update." Vet Clin North Am Small Anim Pract., vol. 34, pp. 1235-1244. (2004).

Miller, K.B., "Manganese Alters Mitochodrial Integrity in the Hearts of Swine Marginally Deficient in Magnesium." Biofactors, vol. 20, No. 2, pp. 85-96. (2004).

Mitchell, G.F. et al. "Measurement of Heart Rate and Q-T Interval in the Conscious Mouse." Am. J. Physiol., vol. 274, pp. H747-H751. (1998).

Moghadam, H.K. "Heritability of Sudden Death Syndrome and Its Associated Correlations to Ascites and Body Weight in Broilers," Br Poult Sci, vol. 46, No. 1, pp. 54-57.(2005).

Mohler, P.J. et al. "Ankyrin-B Mutation Causes Type 4 long -QT Cardiac Arrhythmia and Sudden Cardiac Death." Nature, vol. 421, pp. 634-639. (2003).

Moise, N.S., "Inherited Arrhythmias in the Dog: Potential Experimental Models of Cardiac Disease." Cardiovasc Res, vol. 44, No. 1, pp. 37-46. (1999).

Mongillo, et la., "Fluorescence resonance energy transfer-based analysis of cAMP dynamics in live neonatal rat cardiac myocytes revelas distinct functions of compartmentalized phosphodiesterases," Cir. Res., 95, 67-75 (2004).

Morgan, J. et al. "Abnormal Intracellular Calcium Handling: A Major Cause of Systolic and Diastolic Dysfunction in Ventricular Myocardium from Patients with heart failure." Circulation, vol. 81 (Suppl. 3), pp. 11121-11132. (1990).

Morillo et al. "Chronic Rapid Atrial Pacing: Structural, Functional, and Electrophysiological Characteristics of a New Model of Sustained Atrial Fibrillation." Circulation, vol. 91, pp. 1588-1595. (1995).

Morita, et al., "Ca channel blocking activity of JTV-519, a novel protective drug to cytotoxicity," Neuroscience Research, vol. 31, Supp. 1, p. S65 (1998).

Moschella, M.C. et al., "Inositol 1,4, 5-trisphosphate Receptor Expression in Cardiac Myocytes." J. Cell, Biol., vol. 120, No. 5, pp. 1137-1146. (1993).

Nabauer, M. et al. "Regulation of Calcium Release is Gated by Calcium Current, Not Gating Charge, in Cardiac Myocyres." Science, vol. 244, pp. 800-803. (1989).

Nair, et al., "Syntheis and reactions of 1, 4-benzothiazepine derivatives." Indian Jour. of Chemist., vol. 7, No. 9, pp. 862-865. (1969).

Nakai, et al., "Functional Nonequality of the Cardiac and Skeletal Ryanodine Receptors," Proc. Natl. Acad. Sci. USA, vol. 94, pp. 1019-1022, Feb. 1997.

Nakamura, et al., "Reversal of cisplation resistance by the 1,4-benzothiazepine derivative, JTV-519," Jpn. J. Cancer Res., vol. 92, pp. 597-602 (2001).

Nakamura, Y. et al., "Parasitic Females of Strongyloides Papillosus as a Pathogenetic Stage for Sudden Cardiac Death in Infected Lambs." J. Vet Med. Sci., vol. 56, No. 4, pp. 723-727. (1994).

Nakaya et al. "Inhibitory Effects of JTV-519, a Novel Cardioprotective Drug, on Potassium Currents and Experimental Atrial Fibrillation in Guinea-Pig Hearts," British Journal of Pharmacology, vol. 131, pp. 1363-1372. (2002).

Neumann, J. et al. "Increased Expression of Cardiac Phosphatases in Patient with End-State Heart Failure." J. Mol. Cell. Cardiol., vol. 29, pp. 265-272. (1997).

Ondrias, et al., "FKBP12 modulates gating of the ryanodine receptor/calcium release channel." Ann. N.Y. Acad. Sci., vol. 853, pp. 149-56 1998).

Ondrias, et al., Single channel properties and calcium conductance of the cloned expressed ryanodine receptor/calcium-release channel, Soc. Gen. Physiol. Serv., vol. 51, pp. 29-45 (1996).

Otsu, K. et al. "Molecular cloning of cDNA encoding the Ca2+ release channel (Ryanodine Receptor) of Rabbit Cardiac Muscle Sarcoplasmic Reticulum." J. Biol. Chem., vol 265, No. 23, pp. 13472-13483. (1990).

Oyama, Mark A. et al., "Genomic Expression Patterns of Cardiac Tissues from Dogs with Dilated Cardiomyopathy." AJVR, vol. 66, No. 7, pp. 1140-1155. (Jul. 2005).

Packer, et al., "Effect fo oral milrinone on mortality in severe chronic heart failure," The PROMISE Study Research Group, N. Engl. J. Med., vol. 325, pp. 1468-75 (1991).

Paul-Pletzer, et al., "Identification of a dantrolene-binding sequence on the skeletal muscle ryanodine receptor," J. Biol. Chem., vol. 277, pp. 34918-23 (2002),.

Perry, et al., "Targeting of cyclic AMP degradation to beta 2-adrenergic receptors by beta-arrestins," Science 298, 834-6 (2002).

Pieske, et al., "Ca2+ handling and sarcoplasmic reticulum Ca2+ content in isolated failing and nonfailing human myocardium," Circ. Res., vol. 85, pp. 38-46 (1999).

Pogwidz, S.M. et al. "Mechanisms Underlying Spontaneous and Induced Ventricular Arrhythmias in Patients with Idiopathic Dilated Cardiomyopathy." Circulation, vol. 98, pp. 2404-2414. (1998).

Pogwizd, S.M. et al. "Arrhythmogenesis and contractile Dysfunction in Heart Failure: Roles of Sodium-Calcium Exchange, Inward Rectifier Potassium Current, and Residual Beta-Adrenergic Responsiveness." Circ. Res., vol. 88, pp. 1159-1167. (2001).

Priori, S.G. et al. "Clinical and Molecular characterization of Patients with Catecholaminergic Polymorphic Ventricular Tachycardia." Circulation, vol. 106, pp. 69-74. (2002).

Priori, S.G. et al. "Mutations in the Cardiac Ryanodine Receptor Gene (hRyR2) Underlie Catecholaminergic Polymorphic Ventricular Tachycardia." Circulation, vol. 103, pp. 196-200. (2001).

Protas, L. et al. "Regional Dispersion of L-type Calcium Current in Ventricular Myocytes of German Shepherd Dogs with Lethal Cardiac Arrhythmias." Heart Rhythm, vol. 2, Issue. 2, pp. 172-176. (2005).

Ramirez et al., "Mathematical Analysis of Canine Atrial Action Potentials: Rate, Regional Factors and Electrical Remodeling." Am. J. Physiol. Heart Circ. Physiol., vol. 279, pp. H1767-1785. (2000).

Regitz-Zagrosek, et al. "Myocardial Cyclic AMP and Norepinephrine Content in Human Heart Failure." Eur. Heart J, vol. 15 Suppl. D: pp. 7-13. (1994).

Reiken et al. "Protein Kinase A Phosphorylation of the Cardiac Calcium Release Channel (Ryanodine Receptor) in Normal and Failing Hearts. Role of Phosphatases and Response to Isoproterenol." J. Biol. Chem., vol. 278, No. 1, pp. 444-453. (2003).

Reiken et al., "Beta-Blockers Restore Calcium Release Channel Function and Improve Cardiac Muscle Performance in Human Heart Failure." Circulation, vol. 107, pp. 2459-2466. (2003).

Reiken, S. et al. "Beta-Adrenergic Receptor blockers Restore Cardiac Calcium Release Channel (Ryanodine Receptor Structure and Function inHeart Failure." Circulation, vol. 104, pp. 2843-2848. (2001).

Reiken, S. et al., "PKA Phosphorylation of the Cardiac Calcium Release Channel (Ryanodine Receptor0 in Normal and Failing Hearts: Role of Phosphatases and Response to Isoproterenol." J. Biol. Chem. (2002).

Reiner, G. et al., "Skeletal Muscle Sarcoplasmic Calcium Regulation and Sudden Death Syndrome in Chickens." Br Poult Sci., vol. 36, No. 4, pp. 667-675. (1995).

Rensma et al. "Length of Excitation Wave and Susceptibility to Reentrant Atrial Arrhythmias in Normal Conscious Dogs." Circ. Res., vol. 62, pp. 395-410. (1988).

Richter, et al., "Splice-variants of the cyclic nucleotide phosphodiesterase PDE4D are differentially expressed and regulated in rat tissue," Biochem., vol. 388, pp. 803-811 (2005).

Rosemblit, et al., "Intracellular calcium release channel expression during embryogenesis," Dev. Biol., vol. 206, pp. 163-77 (1999).

Ruehr, et al., "Targeting the protein kinase A by muscle A kinase-anchoring protein (mAKAP) regulates phosphorylation and function of the skeletal muscle ryanodine receptor," J. Biol. Chem., vol. 278, pp. 24831-24836 (2003).

Schotten et al., "Electrical and contractile remodeling during the first days of atrial fibrillation go hand in hand," Circulation, vol. 107, pp. 1433-1439. (2003).

Sen. L.Y. et al. "Inotropic and Calcium Kinetic Effects of Calcium Channel Agonist and antagonist in Isloated Cardiac Myocytes from Cardiomyopathic Hamsters." Circ Res, vol. 67, No. 3, pp. 599-608. (1990).

Sette, et al., "Phosphorylation and activation of a cAMP-specific phosphodiesterase by the cAMP-dependent protein kinase. Involvement of serine 54 in the enzyme activation," J. Biol. Chem., vol. 271, pp. 16526-16534 (1996).

Sette, et al., "The ratPDE3/lvd phosphodiesterase gene codes for multiple proteins differentially activated by cAMP-dependent protein kinase," J. Biol. Chem., vol. 269, pp. 18271-18274 (1994).

Shannon, et al., "Elevated sarcoplasmic reticulum Ca2+ leak in intact ventricular myocytes from rabbits in heart failure," Circ. Res., vol. 93, pp. 592-594 (2003).

Shibata, "264 W94" Current Opinion in Cardiovascular, Pulmonary, and Renal Investigational Drugs., vol. 1, No. 2, pp. 276-278. (1999).

Shinohara, "A Synthesis of Mono-and Dimethoxy -1,2,3,4 -Tetrahydroisoquinolines via Pummerer Reaction: Effects of Methoxyl Groups on Intramolecular Cyclization." Chemical and Pharmaceutical Bulletin, vol. 46, No. 6, pp. 918-927. (1998).

Shiroshita- Takeshita et al., "Atrial fibrillation: basic mechanisms, remodeling and triggers," J. Interv. Card. Electrophysiol, vol. 13, pp. 181-193. (2005).

Shtifman, et al., "Interdomain interactions within ryanodine receptors regulate Ca2+ spark frequency in skeletal muscle," J. Gen. Physiol., vol. 119, pp. 15-31 (2002).

Song, Y. et al. "ATP Promotes Development of Afterdepolarizations and Triggered Activity in Cardiac Myocytes." Am. J. Physiol., vol. 267, pp. H2005-H2011. (1994).

Special Report "Preliminary Report: Effect of Encainide and Flecainide on mortality in a randomized trial of arrhythmia suppression after myocardial infraction," The New England Jour. of Med., vol. 321, No. 6, pp. 406-412. (1989).

Stevenson, W.G. et al., "Sudden death prevention in patients with advanced ventricular dysfunction," Circulation, vol. 88, pp. 2953-2961. 1993.

Suissa, et al., "Bronchodilators and acute cardiac death," Am. J. Respir. Crit. Care Med., vol. 154, pp. 1598-1602 (1996).

Sun et al., "Cellular Mechanisms of Atrial Contractile Dysfunction Caused by Sustained Atrial Tachycardia." Circulation, vol. 98, pp. 719-727. (1998).

Swan, et al., "Calcium channel antagonism reduces exercise-induced ventricular arrhythmias in catecholaminergic polymorphic ventricular tachycardia patents with RyR2 mutations," J. of Card. Electrophysiolog, vol. 16, No. 2, pp. 162-6, (2005).

Swan, H. et al. "Arrhythmic Disorder Mapped to Chromosome 1q42-q43 Causes Malignant Polymorphic Ventricular Tachycardia in Structurally Normal Hearts." J. Am. Coll. Cardiol., vol. 34, No. 7, pp. 2035-2042. (1999).

Szabo et al. "Synthesis and Spectroscopic Investigation of 1,4-Benzothiazepine Derivatives." Magyar Kemiai Folyoirat, vol. 93, No. 6, pp. 269-276. (1987). (in Hungarian and English).

Szabo et al. "Synthesis and Transformation of 4,5-dihydro-1, 4-benzothiazepin-3(2H)-one Derviatives." Magyar Kemiai Folyoirat, vol. 93, No. 3, pp. 139-144. (1987). (in Hungarian and English).

Szabo et al. "Synthesis and Transformations of 4, 5-Dihydro-1,4-benzothiazepin-3(2H)-one Derivatives1,2)." Chemische Berichte., vol. 119, No. 9, pp. 2904-2913. (1986).

Szabo, Janos et al. "Synthesis and Spectroscopic Investigations of 1,4-benzothiazepine derivatives." Can. J. Chem, vol. 65, pp. 175-181. (1987).

Takeshima, H. et al. "Primary Structure and Expression from Complementary DNA of Skeletal Muscle Ryanodine Receptor." Nature, vol. 339, pp. 439-445. (1989).

Tasken, et al. "Phosphodiesterase 4D and protein kinase a type II constitue a signaling unit in the centrosomal area," J. Biol. Chem., vol. 276, pp. 21999-22002 (2001).

Tester, et al., "Compendium of cardiac channel mutations in 541 consecutive unrelated patients referred for long QT syndrome genetic testing," Heart Rhythm. vol. 2, pp. 507-17 (2005).

Tester, et al., "Targeted mutational analysis of the RyR2-encoded cardiac ryanodine receptor in sudden unexplained death: a molecular authopsy of 40 medical examiner/coroner's cases," May Clin. Proc., vol. 79, pp. 1380-4 (2004).

Tieleman et al. "Verapamil Reduces Tachycardia-Induced Electrical Remodeling of the Atria." Circulation, vol. 95, pp. 1945-1953. (1997).

Timerman, et la., "The ryanodine receptor from canine heart sacroplasmic reticulim is associated with a novel FK-506 binding protein," Biochem. Biophys. Res. Commun., vol. 198, pp. 701-6 (1994).

Timmermans et al., "Immediate Reinitiation of Atrial Fibrillation Following Internal Atrial Defibrillation." J. Cardiovasc. Electrophysiol., vol. 9, pp. 122-128. (1998).

Tipton, et al., "My child just fainted: no big deal or sudden-death warning?" Emerg. Med. Serv., vol. 33, pp. 41-5 (2004).

Tse et al. "JTV-519 Japan Tobacco." Curr. Opin. Investig. Drugs. vol. 2, No. 7, pp. 936-939. (2001).

Tsuji, N. et al., "Sudden Cardiac Death in Calves with Experimental Heavy Infection of Strongyloides Papillosus." J. Vet. Med. Sci., vol. 54, No. 6, pp. 1137-1143. (1992).

Tunwell et al., "H. Sapiens mRNA for Ryanodine Receptor 2." GenBank Database, Accession No. X98330. Sep. 9, 1996.

Tunwell et al., "The Human Cardiac Muscle Ryanodine Receptor-Calcium Release Channel: Identification, Primary Structure and Topological Analysis." Biochem. J., vol. 318, pp. 477-487. (1996).

Valdivia, Hector H. et al. "Rapid Adaptation of Cardiac Ryanodine Receptors: Modulation by Mg2+ and Phosphorylation." Science, vol. 267, pp. 1997-2000. (Mar. 31, 1995).

van Rooij, et al., "MCIPI overexpression suppresses left ventricular remodeling and sustains cardiac function after myocardial infarction," Circ. Res., vol. 94, pp. e18-26 (2004).

Verde, et al., "Characterization of the cyclic nucleotide phosphodiesterase subtypes involved in the regulationof the L-type Ca2+ current in rat ventricular myocytes," Br. J. Pharmacol. vol. 127, pp. 65-74 (1999).

Vest, J.A. et al., "Defective Cardiac Ryanodine Receptor Regulation During Atrial Fibrillation." Circulation. vol. 111, No. 16, pp. 2025-2032. (2005).

Vignola, A.M., "PDE4 inhibitors in COPD-a more selective approach to treatment," Respir. Med., vol. 98, pp. 495-503 (2004).

von Altrock, A., "Sudden Deaths in Fattening Herds on taking Blood Samples- Experiences from the Practice." Berl Munch Tieraztl Wschr, vol. 112, pp. 86-90. (1999).

Wang et al. "Regional and Functional Factors Determining Induction and Maintenance of Atrial Fibrillation in Dogs." Am. J. Physiol., vol. 271, pp. H148-158. (1996).

Wang, et al., "Cloning and characterization of novel PDE4D isoforms PDE4D6 and PDE4D7," Cell. Signal., vol. 15, pp. 883-891 (2003).

Wang, et al., "Retinoic acid stimulates annexin-mediated growth plate chondrocyte mineralization," J. Cell Biol., vol. 157, pp. 1061-9 (2002).

Wang, W., et al., "Annexin-mediated Ca2+ influx regulates growth plate chondrocyte maturation and apoptosis," J. Biol. Chem, vol. 278, pp. 3762-9 (2003).

Wang, ZG et al., "Effects of Flecainide and Quinidine on Human Atrial Action Potentials. Role of rate-dependence and comparison with guinea pig, rabbit, and dog tissues," Circulation, Journal of the American Heart Association, vol. 82, pp. 274-283. 1990.

Ward, et al., "Defects in ryanodine receptor calcium release in skeletal muscle from post-myocardial infarct rats," Faseb J., vol. 17, pp. 1517-9 (2003).

Wehrens et al. "Ca2+/Calmodulin-Dependent Protein Kinase II Phosphorylation Regulates the Cardiac Ryanodine Receptor." Circ. Res., vol. 94, No. 6, pp. e61-70 (Apr. 2004).

Wehrens et al. "Enhancing Calstabin Binding to Ryanodine Receptors Improves Cardiac and Skeletal Muscle Function in Heart Failure." Porc Natl Acad Sci USA, vol. 102, No. 27, pp. 9607-9612. (Jul. 5, 2005).

Wehrens et al. "FKBP12.6 Deficiency and Defective Calcium Release Channel (Ryanodine Receptor) Function Linked to Exercise Induced Sudden Cardiac Death." Cell, vol. 113, pp. 829-840. (2003).

Wehrens et al., "Molecular Determinants of Altered Contractility in Heart Failure." Ann Med., vol. 36, Suppl. 1, pp. 70-80. (2004).

Wehrens et al., "Novel Therapeutic Approaches for Heart Failure by Normalizing Calcium Cycling." Nature Reviews Drug Discovery., vol. 3, pp. 565-573. (2004).

Wehrens et al., "Protection form Cardiac Arrhythmia Through Ryanodine Receptor-Stabilizing Protein Calstabin2." Science, vol. 304, pp. 292-296. (Apr. 2004).

Wehrens et al., "Ryanodine Receptor-Targeted Anti-Arrhythmic Therapy." Ann N. Y Acad. Sci., vol. 1047, pp. 366-375. (2005).

Wehrens et al., "Sudden Unexplained Death Caused by Cardiac Ryanodine Receptor (RyR2) Mutations," Mayo Clin Proc., vol. 79, No. 11, pp. 1367-1371. (Nov. 2004).

Wehrens, et al., "Altered function and regulation of cardiac ryanodine receptors in cardiac disease," Trends Biochem. Sci., vol. 28, pp. 671-8 (2003).

Wehrens, et al., "Intracellular Calcium Release Channels and Cardiac Disease," Annu. Rev. Physiol, vol. 67, pp. 69-98. First published on Jul. 21, 2004 (2005).

Wehrens, et al., "Myocardial disease in failing hearts: defective excitation-contraction coupling," Cold Spring Harb. Symp. Quant. Biol., vol. 67, pp. 533-41 (2002).

Wellens et al., "Atrioverter; An Implantable Device for the Treatment of Atrial fibrillation." Circulation, vol. 98, pp. 1651-1656. (1998).

Westphal, R.S. et al. "Regulation of NMDA Receptors by an Associated Phosphatase-Kinase Signaling Complex." Science, vol. 285, pp. 93-96. (1999).

Wijffels et al. "Atrial Fibrillation Begets Atrial Fibrillation: A Study in Awake Chronically Instrumented Goats." Circulation, vol. 92, pp. 1954-1968. (1995).

Wilde et al., "Ion Channels, the QT interval, and arrhythmias," Pacing Clin Electrophysiol, vol. 20, pp. 2048-2051. 1997.

Wit, A.L. et al. "Pathophysiologic Mechanisms of Cardiac Arrhythmias." Am. Heart. J., vol. 106, pp. 798-811. (1983).

Xiang, Y. et al. "Phosphodiesterase 4D is required for β2 adrenoceptor subtype-specific signaling in cardiac myocytes" PNAS, Jan. 18, 2005, vol. 102, No. 3, pp. 909-914.

Xin, H.B. et al. "Oestrogen Protects FKBP12.6 Null Mice from Cardiac Hypertrophy." Nature, vol. 416, pp. 334-337. (2002).

Yamamoto et al. "Abnormal Ca2+ Release from Cardiac Sarcoplasmic Reticulum in Tachycardia-Induced Heart Failure." Cardiovasc. Res., vol. 44, pp. 146-155. (1999).

Yamamoto, et al., "Ca2+- dependent dual function of peptice C. The peptide corresponding to the Glu724-Pro760 region (the so-called determinant of excitation-contraction coupling) of the dihydropyridine receptor alpha 1 subunit II-III loop," J. Biol. Chem., vol. 277, pp. 993-1001 (2002).

Yamamoto, et al., "Peptide probe study of the critical regulatory domain of the cardiac ryanodine receptor," Biochem, Biophys. Res. Commun., vol. 291, pp. 1102-8 (2002).

Yamanoto, et al., "Spectroscopic monitoring of local conformational changes during the intramolecular domain-domain interaction of the ryanodine receptor," Biochemistry, vol. 41, pp. 1492-501 (2002).

Yamamoto, et al., "T-tubule depolarization-induced local events in the ryanodine receptor, as monitored with the fluorescent confromational probe incorporated by mediation of peptide A," J. Biol. Chem. vol. 277, pp. 984-92 (2002).

Yamamoto-Hino, M. et al. "Cloning and Characterization of Human Type 2 and Type 3 Inositol 1,4,5-trisphosphate Receptors." Receptor Channels, vol. 2, pp. 9-22. (1984).

Yamawaza, et al., "Subtype Specificity of the Ryanodine Receptor for Ca2+ Signal Amplification in the Excitation-Contraction Coupling," The EMBO Journal, vol. 15, No. 22, pp. 6172-6177, 1996.

Yang, Jiacheng et al. "A-kinase Anchoring Protein 100 (AKAP100) is Localized in Multiple Subcellular Compartments in The Adult Rat Heart." The Journal of Cell Biology, vol. 142, No. 2, pp. 511-522 (Jul. 27, 1998).

Yano et al., "RvR-Bound FKBP12.6 and the Modulation." Journal Clinical Calcium. vol. 11. No. 6, pp. 743-748. (Jun. 2001).

Yu et al., "Tachycardia-induced Change of Atrial Refractory Period in Humans: Rate Dependency and Effects of Antiarrhythmic Drugs." Circulation, vol. 97, pp. 2331-2337. (1998).

Yue et al., "Ionic Remodeling Underlying Action Potential Changes in a Canine Model of Atrial Fibrillation." Circ. Res., vol. 81, pp. 512-525. (1997).

Zaccolo, et al., "Discrete micro domains with high concentration of cAMP in stimulated rat neonatal cardiac myocytes," Science, vol. 295, pp. 1711-1715 (2002).

Zucchi et al., "The Sarcoplasmic Reticulum Ca2+ Channel/Ryanodine Receptor: Modulation by Endogenous Effectors, Drugs, and Disease States." Pharmacological Reviews, vol. 49, No. 1, pp. 1-51. (1997).

* cited by examiner

*FIGURE 1A*

RyR1 RyR1 S2843A RyR1 S2843D

RyR1 immunoblot

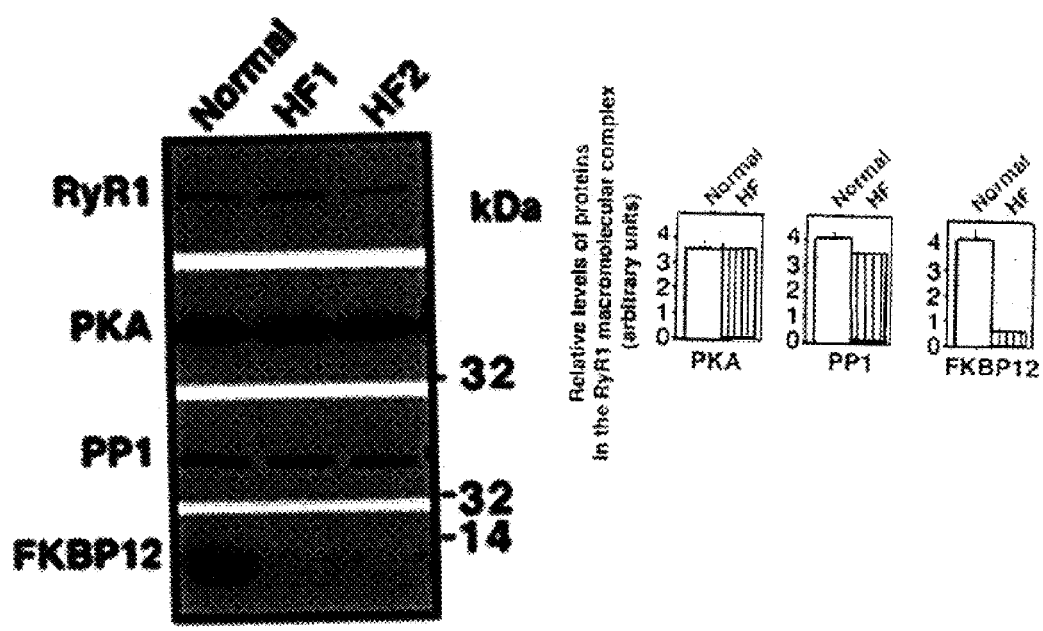

Sham

PMI

Normal skeletal muscle

Heart failure skeletal muscle

TYPE 1 RYANODINE RECEPTOR-BASED METHODS

This application claims priority of provisional application U.S. Ser. No. 60/452,664, filed Mar. 7, 2003, the contents of which are incorporated herein by reference.

The invention disclosed herein was made with government support under grant numbers R01 HL61503-05 from the National Institutes of Health, U.S. Department of Health and Human Services. Accordingly, the U.S. Government has certain rights in this invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The contraction of striated muscle is initiated when calcium ($Ca^{2+}$) is released from tubules within the muscle cell known as the sarcoplasmic reticulum (SR). Calcium release channels, called ryanodine receptors (RyR), on the SR are required for excitation-contraction (EC) coupling. The type 2 ryanodine receptor (RyR2) is found in the heart, while the type 1 ryanodine receptor (RyR1) is found in skeletal muscle. The RyR1 receptor is a tetramer comprised of four 565,000 dalton RyR1 polypeptides and four 12,000 dalton FK-506 binding proteins (FKBP12). FKBP12s are regulatory subunits that stabilize RyR channel function (Brillantes et al., 1994) and facilitate coupled gating between neighboring RyR channels (Marx et al., 1998); the latter are packed into dense arrays in specialized SR regions that release intracellular stores of $Ca^{2+}$, thereby triggering muscle contraction. In addition to FKBP12, the RyR1 macromolecular complex also includes the catalytic and regulatory subunits of PKA, and the phosphatase PP1 (Marx et al., 2001).

One FKBP12 molecule is bound to each RyR1 subunit. Dissociation of FKBP12 significantly alters the biophysical properties of the channels, resulting in the appearance of subconductance states, and increased open probability ($P_o$) of the channels (Brillantes et al., 1994; Gaburjakova et al., 2001). In addition, dissociation of FKBP12 from RyR1 channels inhibits coupled gating resulting in channels that gate stochastically rather than as an ensemble (Marx et al., 1998). Coupled gating of arrays of RyR channels is thought to be important for efficient EC coupling that regulates muscle contraction (Marx et al., 1998). FKBPs are cis-trans peptidyl-prolyl isomerases that are widely expressed and subserve a variety of cellular functions (Marks, 1996). FKBP12s are tightly bound to and regulate the function of the skeletal (RyR1) (Brillantes et al., 1994; Jayaraman et al., 1992) and cardiac (RyR2) (Kaftan et al., 1996) muscle $Ca^{2+}$ release channels, as well as a related intracellular $Ca^{2+}$ release channel known as the type 1 inositol 1,4,5-triphosphate receptor (IP3R1) (Cameron et al., 1997), and the type I transforming growth factor β (TGFβ) receptor (TβRI) (Chen et al., 1997).

Heart failure (HF) is a leading cause of mortality and morbidity world-wide. The disease is characterized by a progressive decrease of contractile function of the heart that leads to hypoperfusion of critical organs. Moreover, many patients with moderate degrees of cardiac dysfunction have substantial impairment of exercise capacity that cannot be explained solely by the extent of their HF (Harrington and Coats, 1997; Minotti et al., 1991; Sullivan and Hawthorne, 1995; Wilson, 1995). This has led to the hypothesis that a primary skeletal muscle defect exists in patients with HF in addition to a primary cardiac muscle defect (Minotti et al., 1991).

The majority of HF patients experience a progressive deterioration of quality-of-life due to their significantly reduced exercise tolerance. In the more severe cases of HF (New York Heart Association class IV), the 2-year mortality rate is over 50% (Braunwald, 1992). Patients and animal models of HF are characterized by a maladaptive response that includes chronic hyperadrenergic stimulation (Bristow et al., 1982). The pathogenic significance of chronic hyperadrenergic stimulation in HF is supported by therapeutic strategies that decrease β-adrenergic stimulation and left ventricular myocardial wall stress and potently reverse ventricular remodeling (Barbone et al., 2001; Bristow et al., 1996).

Chronic β-adrenergic stimulation during HF is associated with cAMP-dependent protein kinase (PKA) hyperphosphorylation of cardiac RyR2 receptors (Marx et al., 2000). The consequent defective function of RyR2, manifested as an SR $Ca^{2+}$ leak through the PKA-hyperphosphorylated channel, has been proposed as a contributing factor to depressed contractile function and arrhythmogenesis in HF (Marks et al., 2002; Marx et al., 2000). Consistent with this hypothesis, PKA hyperphosphorylation of RyR2 in failing hearts has been demonstrated in vivo in both animal models and in patients with HF undergoing cardiac transplantation (Antos et al., 2001; Marx et al., 2000; Ono et al., 2000; Reiken et al., 2001; Semsarian et al., 2002; Yano et al., 2000).

Using animal models of HF, depressed contractile function, including accelerated fatigue development, has been demonstrated in both skeletal muscle (Lunde et al., 2001; Lunde et al., 2002; Perreault et al., 1993) and diaphragmatic muscle (MacFarlane et al., 2000). In these studies, a defect in $Ca^{2+}$ signaling was proposed, but the molecular mechanism underlying impaired skeletal muscle function in HF has hitherto not been elucidated.

SUMMARY OF THE INVENTION

The present invention provides a process for determining whether a first agent inhibits dissociation of a FKBP12 binding protein from the type 1 ryanodine (RyR1) receptor, which comprises (a) separately contacting (i) cells expressing the RyR1 receptor or (ii) sarcoplasmic reticulum or endoplasmic reticulum from an extract from such cells, with (1) both the first agent and a second agent known to cause dissociation of the FKBP12 binding protein from the RyR1 receptor and with (2) only such second agent, under conditions suitable for dissociation of the FKBP12 binding protein from the RyR1 receptor in the presence of such second agent, and (b) measuring the extent of dissociation of the FKBP12 binding protein from the RyR1 receptor in the presence of only the second agent and in the presence of both the first and second agents, a smaller extent of dissociation of the FKBP12 binding protein from the RyR1 receptor in the presence of both the first agent and the second agent than in the presence of only the second agent indicating that the first agent inhibits the extent of dissociation of the FKBP12 binding protein from the RyR1 receptor, so as to thereby determine whether the first agent inhibits dissociation of the FKBP12 binding protein from the type 1 ryanodine (RyR1) receptor.

This invention also provides a process for screening a plurality of agents not known to inhibit dissociation of FKBP12 binding protein from RyR1 receptor to identify an agent that inhibits dissociation of FKBP12 binding protein from RyR1 receptor, which comprises: (a) contacting (i) cells expressing RyR1 receptor or (ii) sarcoplasmic reticulum or endoplasmic reticulum from an extract from such cells, with one or more of the plurality of agents in the presence of a dissociating agent known to cause dissociation of FKBP12 binding protein from RyR1 receptor, under conditions permitting dissociation of FKBP12 binding protein from RyR1 receptor in the presence of such dissociating agent; (b) determining whether the extent of dissociation of FKBP12 binding protein from RyR1 receptor is reduced in the presence of one or more of the plurality of agents, relative to the extent of dissociation of FKBP12 binding protein in the absence of such agents; and (c) if the extent of dissociation determined in step (b) is reduced in the presence of more than one of such agents, separately determining whether such agent inhibits the extent of dissociation of FKBP12 binding protein from RyR1 receptor, so as to thereby determine whether such agent in such plurality of agents inhibits dissociation of FKBP12 binding protein from RyR1 receptor.

The invention further provides a process for preparing a composition which comprises preparing an agent, determining whether the agent inhibits dissociation of FKBP12 binding protein from type 1 ryanodine (RyR1) receptor by the instant process, recovering the agent free of RyR1 receptor, and admixing a carrier and the agent.

The invention further provides a method for treating a subject having defective skeletal muscle function which comprises administering to the subject an amount of an agent effective to decrease dissociation of FKBP12 binding protein from type 1 ryanodine (RyR1) receptor of the subject's skeletal muscle, thereby alleviating the subject's defective skeletal muscle function.

This invention further provides a method for treating a subject having defective skeletal muscle function which comprises administering to the subject an amount of an agent effective to mimic binding of FKBP12 binding protein to type 1 ryanodine (RyR1) receptor/calcium release channel of the subject's skeletal muscle so as to reduce the probability of the channel's opening, thereby alleviating the subject's defective skeletal muscle function.

This invention further provides a method for treating a subject having defective skeletal muscle function which comprises administering to the subject a therapeutically effective amount of an agent determined to inhibit dissociation of FKBP12 binding protein from type 1 ryanodine (RyR1) receptor by any of the processes disclosed herein, or a structural and functional analog or homolog of such agent.

Finally, this invention provides the use of an agent determined to inhibit dissociation of FKBP12 binding protein from type 1 ryanodine (RyR1) receptor by any of the processes disclosed herein for treating an abnormality, wherein the abnormality is alleviated by inhibiting dissociation of FKBP12 binding protein from type 1 ryanodine (RyR1) receptor.

Recordings were at 0 mV and the closed state of the channels is indicated ("C"); channel openings are upwards. All-points amplitude histograms are shown. Open probability ($P_o$), mean closed ($T_c$) and open ($T_o$) dwell times are shown above each channel tracing.

Figure 3A:
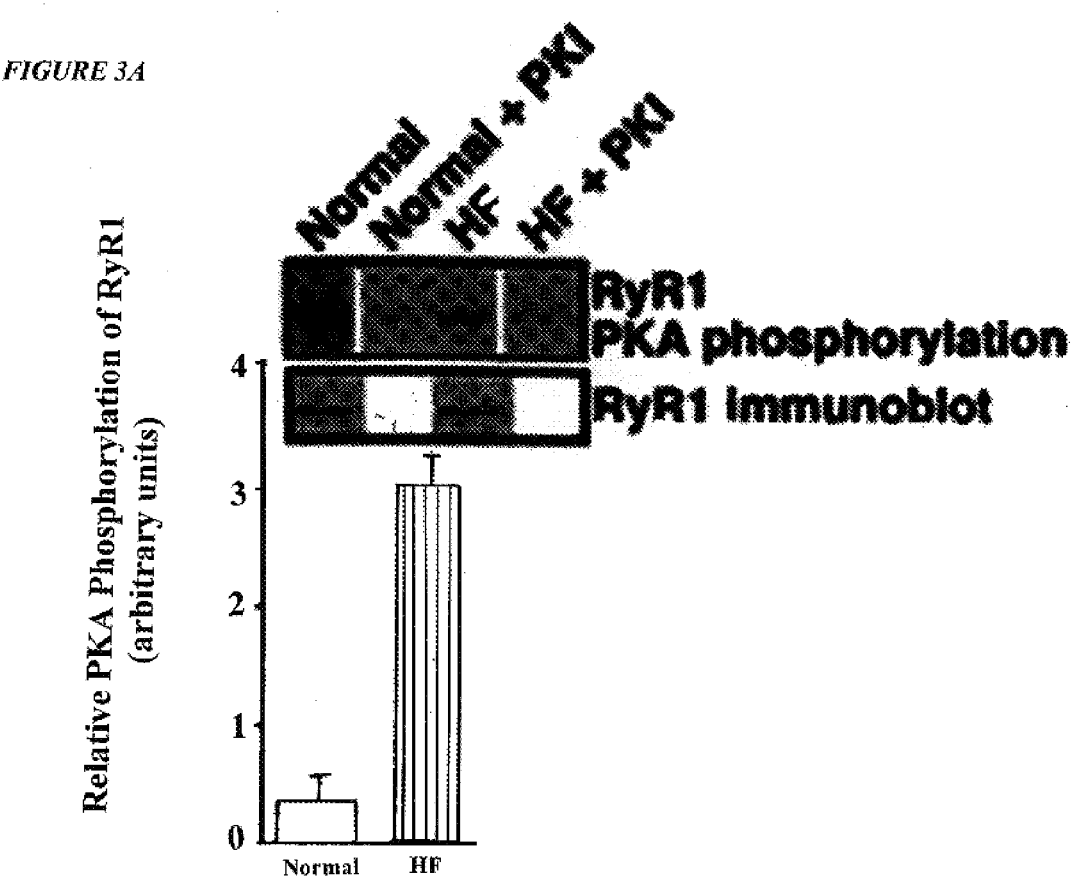
Figure 3B:
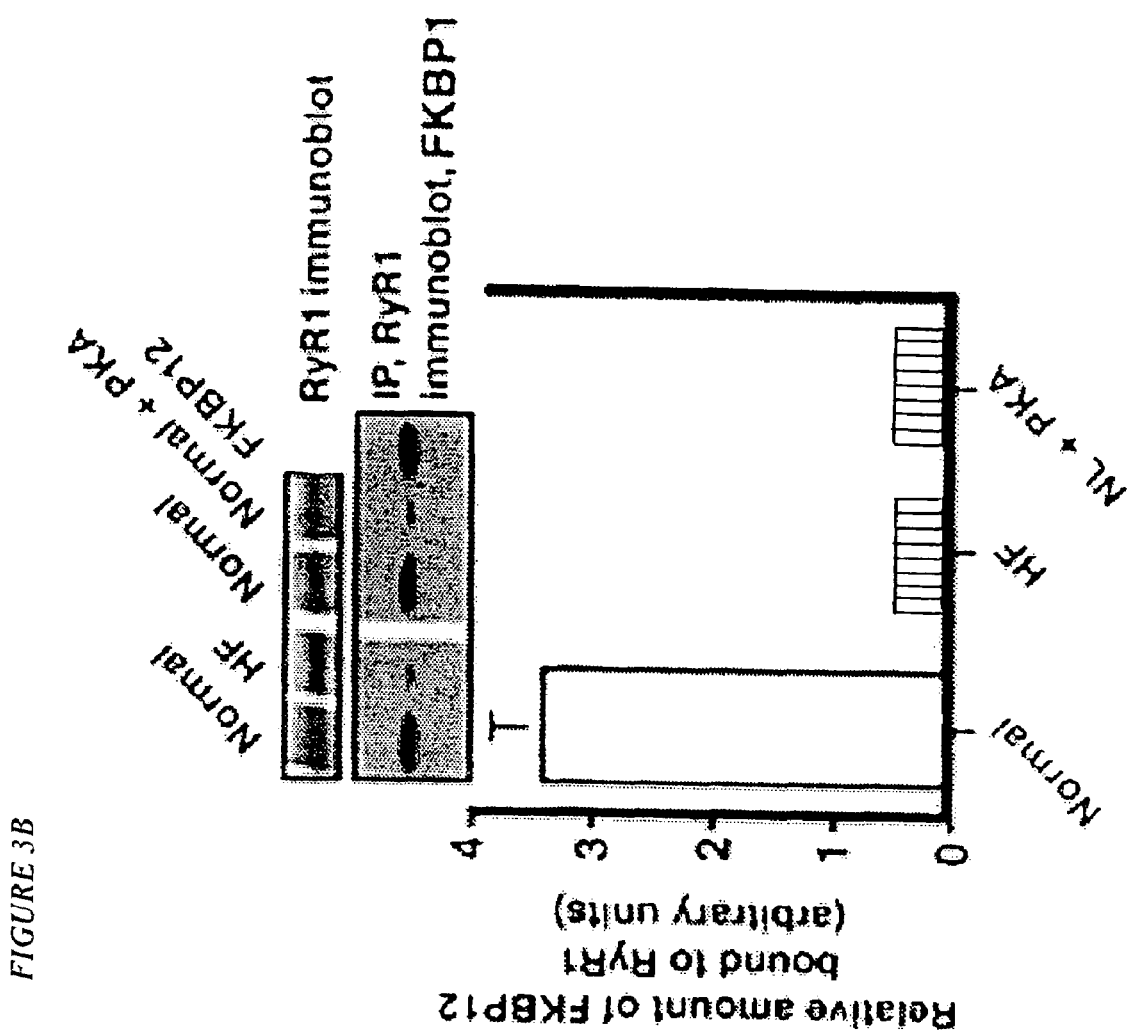

FIGS. 3A-3C. RyR1 PKA hyperphosphorylation in HF skeletal muscle. (A) PKA phosphorylation of RyR1 was measured in skeletal muscle homogenates from control normal dogs and from dogs with pacing-induced HF. Equivalent amounts of RyR1 protein were used in each kinasing reaction as shown by immunoblotting. The relative PKA phosphorylation of RyR1 from skeletal muscle homogenates from normal (n=2) and HF (n=5) animals was determined by dividing the specific phosphorylation signal by the amount of RyR1 protein (determined by immunoblotting and densitometry). Results are expressed as the inverse of the PKA-dependent $[\gamma\text{-}^{32}P]$-ATP signal the standard deviation of the mean. (B) The amount of FKBP12 bound to RyR1 was assessed by co-immunoprecipitation followed by immunoblotting. (C) Representative immunoblots are shown for components of the RyR1 macromolecular complex: RyR1, PKA, PP1, and FKBP12 using samples from normal (n=2) and HF animals (n=5). Protein levels were quantified using densitometry of immunoblots. Results are expressed as the relative amount of each of the components of the RyR1 macromolecular complex corrected for the amount of RyR1 in each immunoprecipitation. Error bars are SD of the mean.

Figure 4A:
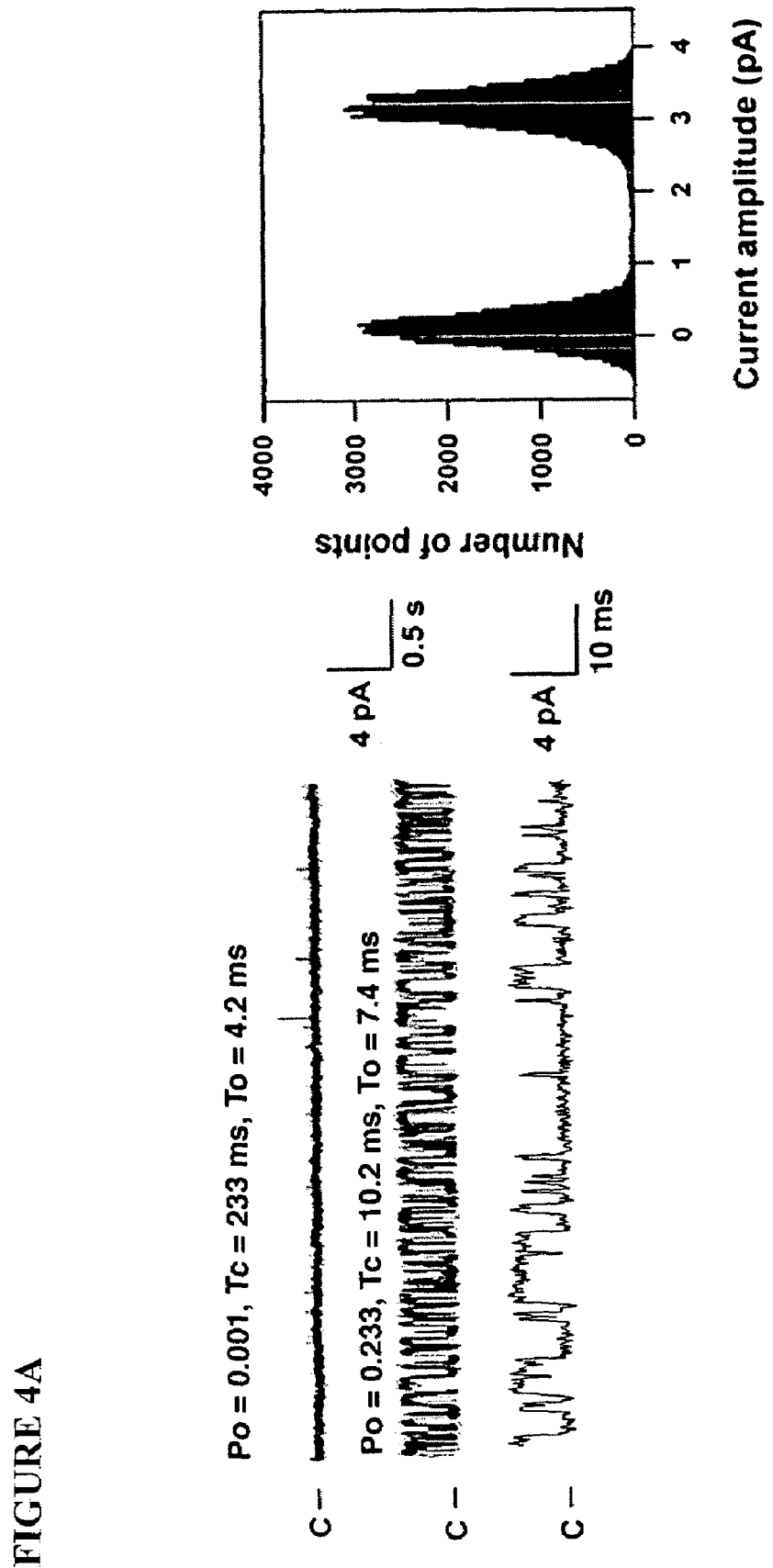
Figure 4B:
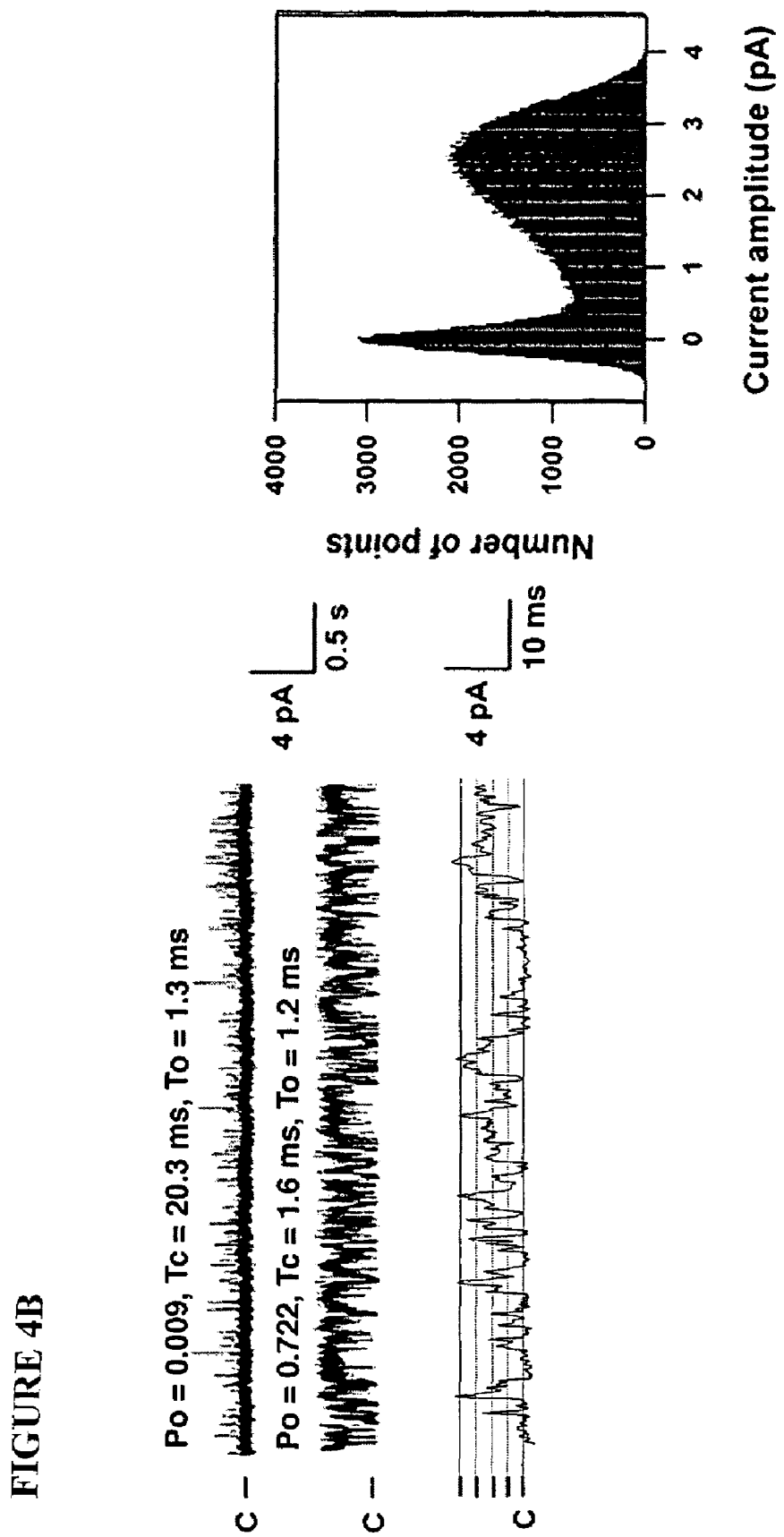

FIGS. 4A and 4B. Defective single channel properties of RyR1 isolated from skeletal muscle during HF. (A) Single channel traces from an RyR1 channel from normal canine skeletal muscle and corresponding current amplitude histogram. (B) Single channel traces from a RyR1 channel from HF canine skeletal muscle and corresponding current amplitude histogram. In A and B, upper tracings were recorded at 100 nM $[Ca^{2+}]_{cis}$, and bottom tracings were recorded after activation of the RyR1 channels with 1 mM ATP to increase open probability ($P_o$). Open ($T_o$) and closed ($T_c$) dwell times and $P_o$ are shown for each condition above the representative tracings. In A and B, the bottom tracing is an expanded time scale. Lines indicating the current levels (0, 1, 2, 3, 4 pA) for the subconductance states of the PKA-hyperphosphorylated channel are shown in the bottom tracing in B. All-points amplitude histograms for each channel are shown. Recordings were at 0 mV and the closed state of the channels are indicated ("C"); channel openings are upward deflections.

Figure 5A:
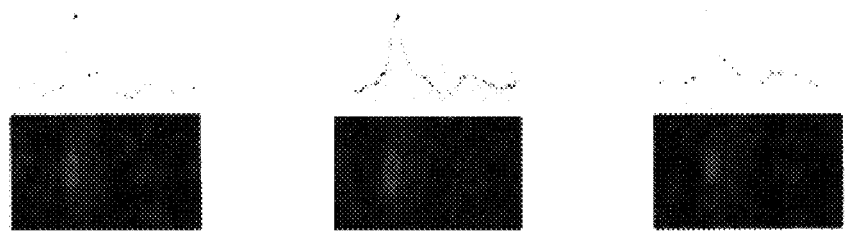
Figure 5A:
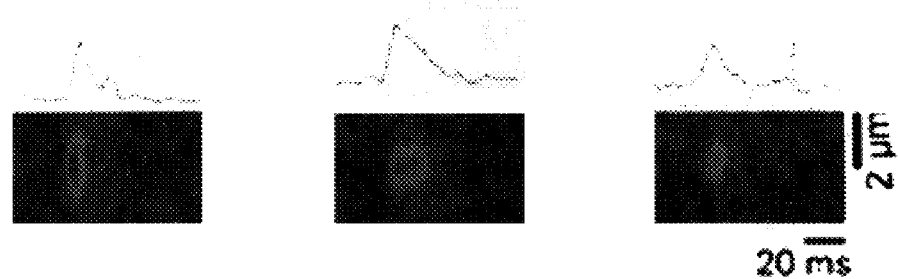
Figures 1, 5B:
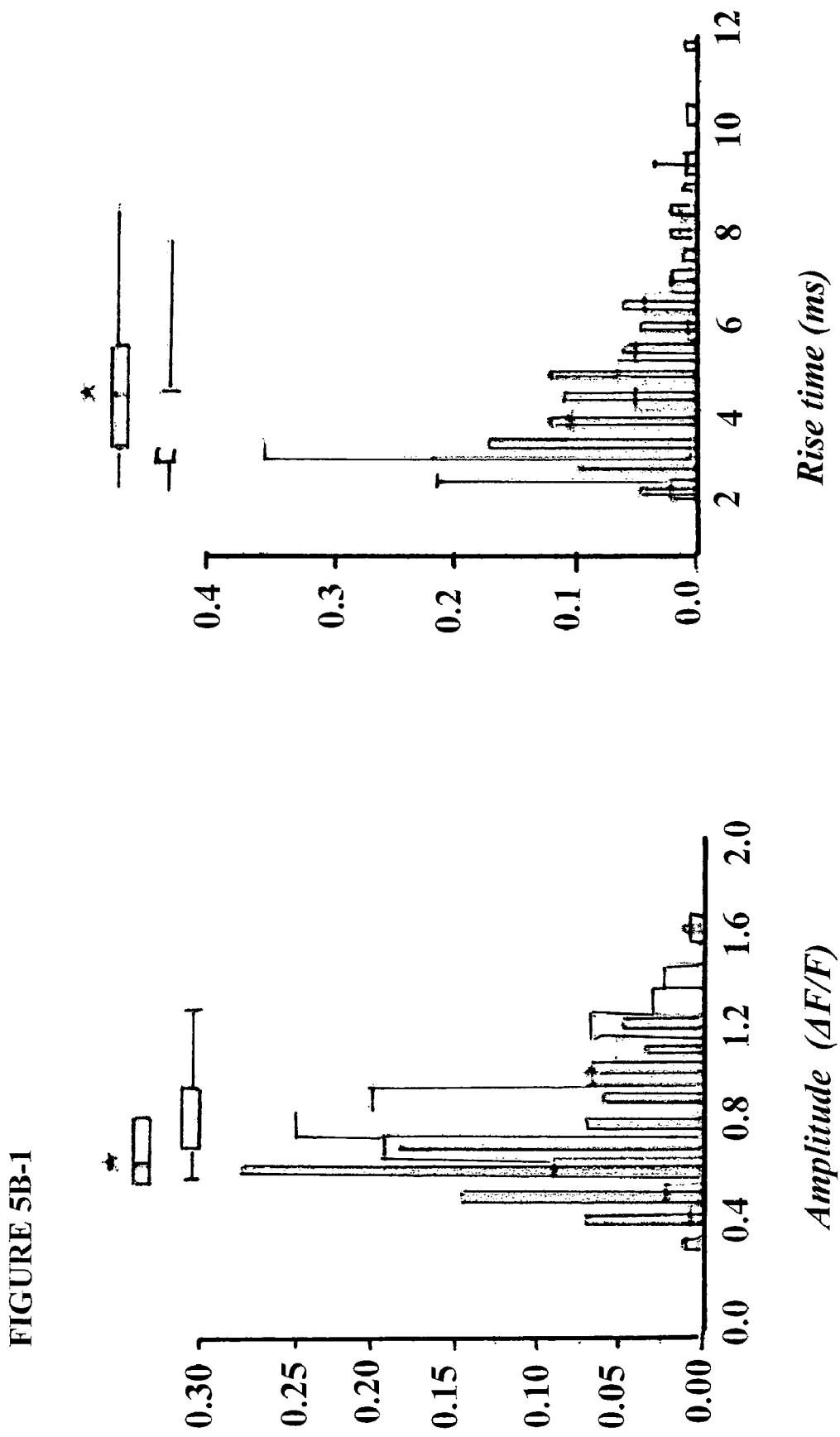

FIGS. 5A and 5B. Defects in local $Ca^{2+}$ signaling in HF skeletal muscle. (A) ΔF/F line scan images of representative examples of $Ca^{2+}$ sparks collected in muscles from sham and post-myocardial infarction (PMI) HF rats. On the top of each image is represented the corresponding $Ca^{2+}$ sparks time-course. (B) Relative distributions of the spatio-temporal properties of the population of $Ca^{2+}$ sparks recorded. On the top of each histogram a box chart indicates the 25, 50 and 75 percentiles; the horizontal lines indicate the range from 1 to 99% of the distribution. Sham: open symbols (n=137, 3 animals), PMI: gray symbols (n=82, 2 animals). (*$P<0.05$). FDHM, full-duration at 1/2 peak amplitude. FWHM, full-width at 1/2 peak amplitude.

FIGS. 6A-6G. RyR1 PKA phosphorylation and muscle fatigue.

(A) Autoradiogram showing the PKA back-phosphorylation of RyR1 from skeletal muscle of sham-operated (control) and HF rats. Bar graph shows the relative PKA phosphorylation of RyR1 (expressed as inverse of back-phosphorylation as described (Marx et al., 2000)). (B) Immunoblots and bar graphs showing relative amounts of RyR1, mAKAP, PDE4D3, PP1 and FKBP12 immunoprecipitated with anti-RyR1 antibody from control and HF skeletal muscle. (C) Immunoblots showing equal amounts of total cellular FKBP12 in control and HF canine and rat skeletal muscles. (D) Immunoblots showing RyR1, mAKAP and PDE4D3 detected in 100 μg human skeletal muscle SR; negative controls are with antibodies pre-absorbed with the corresponding antigenic peptides. (E) HF skeletal muscle fatigues earlier than control. The contralateral soleus muscle from each rat (n=5 control, n=8 HF) was mounted in a tissue bath to assess contractile function (see Materials and Methods for muscle function protocols). Representative fatigue time tracing is shown for control and HF skeletal muscles. Bar graphs show mean (±SD) time to fatigue, *$P<0.05$. (F) HF skeletal muscle achieves tetani more slowly than control. Representative tetani tracing is shown for control and HF skeletal muscles. Tetani were induced by high frequency stimulation as described under Materials and Methods. Bar graphs show tetani 1/2 contraction time, **$P<0.01$. (G) Correlation between time to fatigue and RyR1 PKA phosphorylation (r=0.88) in rat skeletal muscle from sham and HF animals. Muscle function and RyR1 PKA phosphorylation were assessed using contralateral soleus muscles from each animal.

FIGS. 7A-7J. Model of effects of PKA hyperphosphorylation of RyR1 in heart failure skeletal muscle. (A) Depolarization of the skeletal muscle plasma membrane (transverse tubule) activates the voltage-gated $Ca^{2+}$ channel (DHPR) which in turn activates RyR1 via interaction between the cytoplasmic domain of the DHPR and the cytoplasmic domain of RyR1. RyR1 activation opens the channel and releases $Ca^{2+}$ from the SR store into the myoplasm resulting in muscle contraction. Muscle relaxation is determined by reuptake of $Ca^{2+}$ from the cytoplasm back into the SR via the $Ca^{2+}$-ATPase, SERCA. In this model RyR1 is a macromolecular complex that includes four RyR1 and four FKBP12 (shown), as well as PKA and PP1 that are bound to RyR1 via targeting proteins (TP) (only one of the four of each are shown) (Marx et al., 2001). (B) Normal RyR1 exhibit a bell-shaped response to increasing $[Ca^{2+}]_{cyt}$ such that channels are activated at low μM $[Ca^{2+}]_{cyt}$ and inhibited at mM $[Ca^{2+}]_{cyt}$ (C) RyR1 are present in clusters on the SR membrane and open and close as groups of channels via a mechanism referred to as coupled gating which requires FKBP12 (small gray circles) being bound to the channel (Marx et al., 1998). (D) $Ca^{2+}$ sparks represent elemental SR $Ca^{2+}$ release events due to the activation of a group of RyR1 channels (Gonzalez et al., 2000). (E) Tetani (skeletal muscle contraction) is produced when multiple action potentials are summated and a prolonged elevation of myoplasmic $Ca^{2+}$ activates a continuous contraction. (F) Activation of β-adrenergic receptors leads to elevation of cAMP levels which in turn activate PKA which phosphorylates RyR1. PKA hyperphosphorylation of RyR1 in heart failure results in dissociation of most of the FKBP12 from each channel. (G) FKBP12 (small gray circles) dissociation from RyR1 causes loss of coupled gating among channels (Marx et al., 1998). This results in stochastic gating, which means that only a fraction of channels will open at the same time in a group of RyR1 channels because only 50% of the RyR1 channels are anatomically associated with DHPR (meaning that 50% of the RyR1 cannot be activated via interaction with a DHPR) (Franzini-Armstrong and Kish, 1995). (H) $Ca^{2+}$ sparks from heart failure skeletal muscle exhibit delayed upstroke, reduced amplitude and prolonged decay, all of which are consistent with the loss of coupled gating among groups of RyR1 channels. Solid line is a $Ca^{2+}$ signal in heart failure skeletal muscle, dashed line represents $Ca^{2+}$ signal in normal skeletal muscle. (I) Tetani develop in skeletal muscle as a result of repeated high frequency action potentials that cause a summation of $Ca^{2+}$ release events resulting in maintained elevation of myoplasmic $Ca^{2+}$. (J) Slowing of the rise time of $Ca^{2+}$ release and reduced amplitude are consistent with the delay in development of tetani observed in heart failure skeletal muscle. Solid line is tetani development in heart failure skeletal muscle, and dashed line represents normal tetani.

DETAILED DESCRIPTION OF THE INVENTION

Definitions

The following definitions are presented as an aid in understanding this invention.

As used herein, "RyR1 receptor" means a type 1 ryanodine receptor, which is a calcium ($Ca^{2+}$) release channel found on the sarcoplasmic reticulum (SR) of skeletal muscle. "RyR2 receptor" means a type 2 ryanodine receptor, which is a calcium ($Ca^{2+}$) release channel found on the sarcoplasmic reticulum (SR) of the heart.

"FKBP12" means a FK-506 binding protein having a molecular weight of about 12,000 daltons, which binds to and regulates the function of the RyR1 receptor channel. "FKBP12.6" means a FK-506 binding protein having a molecular weight of about 12,000 daltons, which binds to and regulates the function of the RyR2 receptor channel.

"PKA phosphorylation" means a reaction in which a phosphate group is substituted for a hydroxyl group by the enzyme protein kinase A (PKA).

"Back-phosphorylation" of RyR1 or RyR2 receptor means the in vitro phosphorylation of receptor by protein kinase A.

EMBODIMENTS OF THE INVENTION

This application discloses that RyR1 channels in skeletal muscle from canine and rat models of HF were PKA-hyperphosphorylated, depleted of FKBP12 and exhibited increased activity, suggesting that the channels are "leaky." PKA hyperphosphorylation of RyR1 correlated with impaired SR $Ca^2$ release and early fatigue in HF skeletal muscle. These findings identify a novel mechanism that regulates RyR1 function via PKA phosphorylation in response to SNS stimulation. PKA hyperphosphorylation of RyR1 may contribute to impaired skeletal muscle function in HF, suggesting that a generalized EC coupling myopathy may play a role in heart failure.

Specifically, the present invention provides a process for determining whether a first agent inhibits dissociation of a FKBP12 binding protein from the type 1 ryanodine (RyR1) receptor, which comprises (a) separately contacting (i) cells expressing the RyR1 receptor or (ii) sarcoplasmic reticulum or endoplasmic reticulum from an extract from such cells, with (1) both the first agent and a second agent known to cause dissociation of the FKBP12 binding protein from the RyR1 receptor and with (2) only such second agent, under conditions suitable for dissociation of the FKBP12 binding protein from the RyR1 receptor in the presence of such second agent, and (b) measuring the extent of dissociation of the FKBP12 binding protein from the RyR1 receptor in the presence of only the second agent and in the presence of both the first and second agents, a smaller extent of dissociation of the FKBP12 binding protein from the RyR1 receptor in the presence of both the first agent and the second agent than in the presence of only the second agent indicating that the first agent inhibits the extent of dissociation of the FKBP12 binding protein from the RyR1 receptor, so as to thereby determine whether the first agent inhibits dissociation of the FKBP12 binding protein from the type 1 ryanodine (RyR1) receptor. In one embodiment, the first agent is not previously known to inhibit dissociation of the FKBP12 binding protein from the RyR1 receptor.

This invention also provides a process of screening a plurality of agents not known to inhibit dissociation of FKBP12 binding protein from RyR1 receptor to identify an agent that inhibits dissociation of FKBP12 binding protein from RyR1 receptor, which comprises: (a) contacting (i) cells expressing RyR1 receptor or (ii) sarcoplasmic reticulum or endoplasmic reticulum from an extract from such cells, with one or more of the plurality of agents in the presence of a dissociating agent known to cause dissociation of FKBP12 binding protein from RyR1 receptor, under conditions permitting dissociation of FKBP12 binding protein from RyR1 receptor in the presence of such dissociating agent; (b) determining whether the extent of dissociation of FKBP12 binding protein from RyR1 receptor is reduced in the presence of one or more of the plurality of agents, relative to the extent of dissociation of FKBP12 binding protein in the absence of such agents; and (c) if the extent of dissociation determined in step (b) is reduced in the presence of more than one of such agents, separately determining whether such agent inhibits the extent of dissociation of FKBP12 binding protein from RyR1 receptor, so as to thereby determine whether such agent in such plurality of agents inhibits dissociation of FKBP12 binding protein from RyR1 receptor.

In one embodiment of any of the processes described herein, determining the extent of dissociation of FKBP12 binding protein from RyR1 receptor comprises measuring protein kinase A phosphorylation of RyR1 receptor. In one embodiment, for example, measuring protein kinase A phosphorylation of RyR1 receptor comprises detecting binding of an antibody that binds to the phosphorylated form, but not the nonphosphorylated form, of RyR1 receptor. In another embodiment, determining the extent of dissociation of FKBP12 binding protein from RyR1 receptor comprises measuring the fluorescence of a calcium-sensitive fluorescent dye. In a further embodiment, the RyR1 receptor is a human RyR1 receptor.

In one embodiment of the instant methods, the cells are contacted with the agent(s) and the RyR1 receptor is expressed from nucleic acid endogenous to such cells. In another embodiment, the cells are contacted with the agent(s) and the RyR1 receptor is expressed from nucleic acid transfected into such cells. In a further embodiment, the cells are bacterial, yeast, insect, amphibian, plant or mammalian cells. Mammalian cells include, for example, HEK293 cells, Chinese hamster ovary (CHO) cells, COS-7 cells, LM(tk⁻) cells, mouse embryonic fibroblast NIH-3T3 cells, mouse Y1 cells, 293 human embryonic kidney cells and HeLa cells. Insect cells include, for example, Sf9 cells, Sf21 cells and *Trichoplusia ni* 5B-4 cells. Amphibian cells include, for example, *Xenopus* oocyte cells and *Xenopus* melanophore cells.

In another embodiment, the cells are skeletal muscle cells from a subject with a failing heart. The subject can be, for example, an animal in which heart failure has been induced by rapid cardiac pacing, or a human.

This invention also provides a process for preparing a composition which comprises preparing an agent, determining whether the agent inhibits dissociation of FKBP12 binding protein from type 1 ryanodine (RyR1) receptor by any of the processes described herein, recovering the agent free of RyR1 receptor, and admixing a carrier and the agent.

This invention further provides a method for treating a subject having defective skeletal muscle function which comprises administering to the subject an amount of an agent effective to decrease dissociation of FKBP12 binding protein from type 1 ryanodine (RyR1) receptor of the subject's skeletal muscle, thereby alleviating the subject's defective skeletal muscle function. In one embodiment, the agent is JTV519, a 1,4-benzothiazepine derivative (Yano et al., 2003).

This agent is envisioned for use in the other instant methods and compositions described below. In another embodiment, the agent decreases protein kinase A (PKA) phosphorylation of type 1 ryanodine (RyR1) receptor of the subject's skeletal muscle. In still another embodiment, the agent is a beta adrenergic blocker. In a further embodiment, the agent is not a beta adrenergic blocker.

This invention further provides a method for treating a subject with defective skeletal muscle function which comprises administering to the subject an amount of a beta adrenergic blocker effective to alleviate the subject's defective skeletal muscle function.

In one embodiment, the beta adrenergic blocker is carvedilol (Coreg®, SmithKline Beecham) or metoprolol (Toprol-XL®, AstraZeneca). In different embodiments., the dose of carvedilol is from 6.25 mg orally per day up to 50 mg orally twice per day. In different embodiments, the dose of metoprolol is from 12.5 to 200 mg orally per day.

In one embodiment of any of the methods described above, the subject's defective skeletal muscle function occurs during heart failure. In another embodiment, the agent also alleviates the subject's heart failure. In a further embodiment, the agent is not a beta adrenergic blocker. The agent can be, for example, Dantrolene, or a derivative, homolog, analog, metabolite, or prodrug of Dantrolene.

In one embodiment of any of the methods described above, the subject's defective skeletal muscle function occurs during chronic obstructive pulmonary disease, hypertension, asthma, or hyperthyroidism.

This invention further provides a method for treating a subject having defective skeletal muscle function which comprises administering to the subject an amount of an agent effective to mimic binding of FKBP12 binding protein to type 1 ryanodine (RyR1) receptor/calcium release channel of the subject's skeletal muscle so as to reduce the probability of the channel's opening, thereby alleviating the subject's defective skeletal muscle function. In one embodiment, the subject's defective skeletal muscle function occurs during heart failure. In another embodiment, the agent also alleviates the subject's heart failure. In a further embodiment, the subject's defective skeletal muscle function occurs during chronic obstructive pulmonary disease, hypertension, asthma, or hyperthyroidism.

This invention further provides a method for treating a subject having defective skeletal muscle function which comprises administering to the subject a therapeutically effective amount of an agent determined to inhibit dissociation of FKBP12 binding protein from type 1 ryanodine (RyR1) receptor by any of the processes disclosed herein, or a structural and functional analog or homolog of such agent.

In one embodiment of any of the methods described above, the subject's defective skeletal muscle function occurs during heart failure. In another embodiment, the agent also alleviates the subject's heart failure. In a further embodiment, the subject's defective skeletal muscle function occurs during chronic obstructive pulmonary disease, hypertension, asthma, or hyperthyroidism. In still a further embodiment, the agent is not a beta adrenergic blocker.

This invention further provides the use of an agent determined to inhibit dissociation of FKBP12 binding protein from type 1 ryanodine (RyR1) receptor by any of the processes disclosed herein for treating an abnormality, wherein the abnormality is alleviated by inhibiting dissociation of FKBP12 binding protein from type 1 ryanodine (RyR1) receptor. In one embodiment, the compound is not a beta adrenergic blocker. In another embodiment, the preparation of the pharmaceutical composition comprises admixing a pharmaceutically effective amount of the agent with a pharmaceutically acceptable carrier.

This invention further provides a chemical compound identified by any of the methods described herein.

This invention still further provides a method for making a composition which specifically binds to a RyR1 receptor which comprises identifying a chemical compound using any one of the methods described herein, synthesizing the chemical compound or a novel structural and functional analog or homolog thereof, and admixing a pharmaceutically effective amount of the chemical compound with a pharmaceutically acceptable carrier.

This invention also provides a pharmaceutical composition comprising (a) an amount of a chemical compound identified using any one of the methods described herein and (b) a pharmaceutically acceptable carrier capable of passing through the cell membrane.

This invention further provides assays for RyR1 receptor channel function which comprise measuring protein kinase A (PKA) phosphorylation of the RyR1 receptor, the degree of association of the FKBP12 binding protein with the RyR1 receptor, the subconductance state of the RyR1 receptor channel, the $Ca^{2+}$ sensitivity for activation of the RyR1 receptor channel, or the open probability ($P_o$) of the RyR1 receptor channel.

In the subject invention, a "pharmaceutically effective amount" is any amount of a compound which, when administered to a subject suffering from a disease against which the compound is effective, causes reduction, remission, or regression of the disease.

In one embodiment, the therapeutically effective amount of the compound is between about 0.03 and about 1000 mg per day. In another embodiment, the therapeutically effective amount is between about 0.30 and about 300 mg per day. In one embodiment, the therapeutically effective amount is between about 1.0 and about 100 mg per day.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions. In one embodiment, the carrier is not water.

Finally, this invention provides for homologs, analogs, isomers, prodrugs and metabolites of any of the compounds or agents described herein. A "structural and functional analog" of a chemical compound has a structure similar to that of the compound but differing from it in respect to a certain component or components. A "structural and functional homolog" of a chemical compound is one of a series of compounds each of which is formed from the one before it by the addition of a constant element. The term "analog" is broader than and encompasses the term "homolog." "Isomers" are chemical compounds that have the same molecular formula but different molecular structures or different arrangement of atoms is space. The isomers may be structural isomers, positional isomers, stereoisomers, optical isomers, or cis-trans isomers. In general, "prodrugs" will be functional derivatives of compounds which are readily convertible in vivo into the required compound. Conventional procedures for the selection and preparation of suitable prodrug derivatives are described, for example, in Design of Prodrugs, ed. H. Bundgaard, Elsevier, 1985. "Metabolites" include active species produced upon introduction of compounds into the biological milieu.

Approaches to designing and synthesizing receptor selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind the receptor to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for "lead compounds" that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

Experimental Details

The present application is based on the finding that the composition and function of the RyR1 calcium release channel on the SR that is required for skeletal muscle EC coupling are altered due to PKA hyperphosphorylation in animal models of heart failure. During heart failure, PKA hyperphosphorylation of RyR1 causes depletion of the regulatory subunit, the FK506 binding protein (FKBP12), in the RyR1 channel macromolecular complex resulting in channels with altered gating. PKA hyperphosphorylation of RyR1 correlates with altered $Ca^{2+}$ signaling and early fatigue in heart failure skeletal muscle. The defects in RyR1 structure and function are similar to those previously reported for the cardiac muscle RyR2, suggesting that heart failure is a generalized EC coupling myopathy involving both cardiac and skeletal muscles. The present findings indicate that indeed skeletal muscle, like cardiac muscle, undergoes changes due to the chronic hyperadrenergic state of heart failure that represent a maladaptive response and result in further impairment of muscle function.

Materials and Methods

Expressing and Purifying Recombinant RyR1

Recombinant WT and mutant RyR1 were expressed, isolated and characterized as previously described (Brillantes et al., 1994; Gaburjakova et al., 2001). Briefly, RyR1 cDNA were cloned into the mammalian expression vector pCMV5 using the NheI and XbaI sites. HEK293 cells were grown in Minimal Essential Medium (MEM) with 25 mM HEPES (Gibco), supplemented with 10% (v/v) fetal bovine serum (Gibco), penicillin (100 U/ml), streptomycin (100 mg/ml), and L-glutamine (2 mM). One T175 flask (50% confluent) of HEK293 cells was transfected with 20 µg of RyR1 cDNA using the $Ca^{2+}$ phosphate precipitation method (Gaburjakova et al., 2001). Forty-eight hours post-transfection cells were washed twice, scraped into phosphate-buffered saline, and pelleted by centrifugation at 2500×g for 5 min at 4° C. Microsomes were prepared, aliquoted, and stored at −80° C. as described (Gaburjakova et al., 2001).

Immunoblots, Immunoprecipitations and Phosphorylation

Sarcoplasmic reticulum (SR) membranes were prepared from hind limb canine skeletal muscle tissue. Briefly, ~10 g of tissue was minced and homogenized in 50 ml of 10 mM Tris-maleate buffer, pH 6.8 containing NaF (5 mM) and protease inhibitors (1.0 mM benzamidine, 5.0 µg/ml pepstatin, 5.0 µg/ml leupeptin, 1.0 µg/ml aprotin, 1.0 mM pefabloc). Homogenates were centrifuged for 20 min at 4,000×g, and the supernatants were recentrifuged at 10,000×g for 20 min. The resulting supernatant was centrifuged at 40,000×g for 30 min and the pellet resuspended in 0.2 ml of 10 mM Tris-maleate (pH 6.8) containing 0.3 M sucrose and 0.9% NaCl. Protein concentration was measured by the method of Bradford with bovine serum albumin as a standard, samples were aliquoted, flash frozen in liquid nitrogen and stored at −80° C. until use. Skeletal muscle lysates were prepared from 1.0 g of canine tissue or whole rat soleus muscles homogenized in 1.0 ml of buffer containing 50 mM Tris-HCl (pH 7.4), 200 mM NaCl, 20 mM NaF, 1.0 mM $Na_3VO_4$, 1.0 mM DTT, and protease inhibitors. Samples were centrifuged at 3000×g for 10 min. After determining the protein concentration supernatants were aliquoted and stored at −80° C. until use. For immunoprecipitations skeletal SR samples were suspended in 0.5 ml of IP buffer [50 mM Tris-HCl (pH 7.4), 0.9% NaCl, 0.5 mM NaF, 0.5 mM $Na_3VO_4$, 0.25% Triton X-100, and protease inhibitors] and incubated with anti-RyR antibody overnight at 4° C. Immunoblots were performed using the following primary antibodies: anti-PKA catalytic subunit (1:1000), anti-PP1 (1:1000), (Transduction Labs), anti-FKBP (1:1000) (Jayaraman et al., 1992), anti-RyR-5029 (1:3000) (Jayaraman et al., 1992), anti-PDE4D3 (1:1000) [affinity purified polyclonal antibody raised in rabbits immunized with a mixture of two PDE4D3 peptides, residues 1-14 of human PDE4D3 with a carboxy terminal cysteine added for conjugation to kehole limpet hemocyanin (KLH), and the corresponding rat sequence that has a T instead of an N at residue 6, MMHVNN/TFPFRRHSW(C)], anti-mAKAP (1:750) [affinity purified polyclonal antibody raised in rabbits immunized with a peptide corresponding to mAKAP sequence with an amino-terminal cysteine added for conjugation to KLH, (C)ETRFNNRQDSDALKSSDD]. Protein A-Sepharose beads were added, incubated at 4° C. for 1 hr, and washed 3× with IP buffer. After washing, membranes were incubated with peroxidase-conjugated goat anti-rabbit or goat anti-mouse IgG antiserum (1:3000, Boehringer-Mannheim) for 60 minutes at room temperature, washed 3× with Tris-buffered saline (TBS), 0.1% Tween 20, and developed using enhanced chemiluminescence (ECL, Amersham).

For phosphorylations, beads were washed with 1× phosphorylation buffer [8 mM $MgCl_2$, 10 mM EGTA, 50 mM Tris/piperazine-N,N'-bis(2-ethanesulfonic acid), pH 6.8], resuspended in 10 µl of 1.5× phosphorylation buffer containing either vehicle alone, PKA catalytic subunit (5 units, Sigma), PKA plus PKA inhibitor ($PKI_{5-24}$, 500 nM, Calbiochem), or cAMP (10 µM). Phosphorylation of immunoprecipitated RyR1 was initiated with Mg-ATP (33 µM), [$\gamma$-$^{32}$P]-ATP, and terminated after incubation for 5 min at RT with 5µl stop solution (4% SDS and 0.25 M DTT). For dephosphorylation experiments, the cAMP reaction was terminated by addition of PKI, followed by addition of protamine (1 mg/ml)++/− okadaic acid (5 µM). Samples were heated to 95° C., size fractionated on 6% SDS-PAGE, and RyR2 radioactivity was quantified using a Molecular Dynamics Phosphorimager and ImageQuant software (Amersham Pharmacia Biotech). Non-specific phosphorylation (not inhibited by PKI) was subtracted and the $^{32}$P/RyR1 ratio was calculated by dividing $^{32}$P_phosphorylation by the amount of high affinity [$^3$H]-ryanodine binding (one high affinity ryanodine binding site per RyR1). All experiments were performed in triplicate and the investigator was blinded to the source of samples.

FKBP12 Binding

Microsomes (200 µg) were resuspended in 0.1 ml imidazole buffer (5 mM imidazole, pH 7.4, and 0.3 M sucrose), containing protease inhibitors, and incubated with Mg-ATP (100 μM) and either PKA (10 units) or cAMP (10 μM) at 30° C. for 30 min. Samples were centrifuged at 95,000×g for 10 min, and supernatants collected. Pellets were washed 2× in 0.2 ml imidazole buffer and centrifuged at 95,000×g for 10 min. The final pellet was resuspended in 0.1 ml imidazole buffer. In some experiments, pellets were phosphorylated with cAMP, then dephosphorylated with alkaline phosphatase (1:100 enzyme:protein) or by activating endogenous phosphatases with protamine (1 mg/ml). Recombinant FKBP12 was added to these samples for 4 h at 4° C. to allow binding to RyR1. Pellet and supernatant were size-fractionated by SDS-PAGE and immunoblotted for FKBP12.

Measurement of Muscle Function

Soleus muscles were attached to a force transducer in a water bath (Harvard Apparatus) and perfused with Krebs-Henseleit containing 2 mM $Ca^{2+}$ bubbled with 5% $CO_2$/95% $O_2$. The muscle was rested for 60 min, then stimulated with single pulses at 10 sec intervals. The twitch force, twitch contraction time, and half-relaxation time were measured. Stimulation was at 1 Hz at 1-30 V. The tetani force, half-contraction time, and half-relaxation time were also determined by using a stimulating frequency and titanic duration of 50 Hz and 600 ms (Lunde et al., 2001). Fatigue was produced by inducing a tetanus every 2 sec and measuring the time for force to fall to 40% of the maximum.

Single Channel Recordings

SR vesicles from control or HF skeletal muscle, or vesicles from HEK293 cells transfected with recombinant WT or mutant RyR1 were incorporated into planar lipid bilayers and single channel recordings of RyR1 were performed as described (Brillantes et al., 1994; Gaburjakova et al., 2001). Microsomes containing WT RyR1 were phosphorylated with PKA as described above. Vesicles were added to the cis chamber and induced to fuse with planar lipid bilayers composed of 3:1 phosphatidyl ethanolamine/ phosphatidyl serine (Avanti Polar Lipids). The bilayer cup was made of polystyrene with a 0.15 mm aperture. Fusion was promoted by KCl added to the cis chamber. After incorporation of a single $Ca^{2+}$-release channel, the KCl gradient was eliminated by perfusion of the cis chamber with cis solution.

Solutions used for channel analysis were as follows: trans solution, 250 mM Hepes, 53 mM $Ca(OH)_2$, 50 mM KCl, pH=7.35; and cis solution, 250 mM HEPES, 125 mM Tris, 50 mM KCl, 1 mM EGTA, 0.5 mM $CaCl_2$, pH=7.35. Free $[Ca^{2+}]$ in the cis compartment was calculated using the Chelator software (Schoenmakers et al., 1992). The trans chamber was connected to the head-stage of an Axon 200 amplifier (Axon Instruments) using a Ag/AgCl electrode and agar/KCl bridge. The cis chamber was held at ground with a similar electrode. The single-channel currents were filtered at 1 kHz with an 8-pole Bessel filter (Warner Instruments) and digitized at 4 kHz. Data were collected on a Pentium computer, using AxoScopel and a Digidata 1200 interface (Axon Instruments). pClamp 6 (Axon Instruments) was used for analyzing single channel data. Open probability and the lifetime of open events and gating frequency were identified by 50% threshold analysis using at least 2 min of continuous record. At the conclusion of each experiment, ryanodine (5 μM) was applied to the cis chamber to confirm channels were ryanodine receptors. Mean open and closed dwell time analysis was performed using Fetchan software (Axon Instruments), and open time distribution was fitted with a two-exponential least-square regression analysis as described (Marx et al., 2001). All data are expressed as mean±SE. The unpaired Student's t-test was used for statistical comparison of mean values between experiments. A value of $P<0.05$ was considered significant.

Canine Heart Failure Model

Seven dogs weighing between 28 and 30 kg were used for this study. Rapid left ventricular pacing was used to induce heart failure as previously described (Wang et al., 1997). The animals were assigned to one of two groups: 1) Normal without heart instrumentation (n=2), and 2) heart failure (n=5). In group 2 after baseline measurements had been obtained, rapid LV pacing was initiated at 210 bpm for 3 weeks, followed by an additional week of pacing at 240 bpm with an external pacemaker (EV4543, Pace Medical, Inc). This rapid cardiac pacing regimen has been used previously to induce well characterized severe HF (Wang et al., 1997). The hemodynamic measurements were performed at least 40 min after the pacemaker was turned off. Baseline LV change in pressure over time ($dP/dt_{max}$, mmHg/s) was 3420±105 and fell to 1722.2±322 (p<0.01) in animals subjected to rapid LV pacing, consistent with the development of HF.

Rat Infarct Model

Twelve Sprague-Dawley rats (300-400 g) and two Wistar rats underwent left coronary ligation via left thoracotomy. All animals were intubated and ventilated (Harvard Apparatus, Holliston, Mass.) for the duration of the procedure. An additional six Sprague-Dawley rats and three Wistar rats underwent sham operations without coronary ligation (control group). After one week, echocardiography was performed on all 18 rats. Six months following coronary ligation, echocardiography was repeated and hemodynamic data was collected. To this end, a Millar catheter (Millar Instruments, Inc., Houston, Tex.) was inserted into the right carotid artery and advanced to the left ventricle. Using a Millar pressure transducer catheter (Millar Instruments, Houston, Tex.) and a MacLab (AD Instruments, Grand Junction, Colo.), left ventricle end-diastolic pressure, left ventricle systolic pressure, mean aortic pressure, heart rate, and left ventricular dP/dt were determined. Animals were then euthanized and the soleus muscles harvested.

$Ca^{2+}$-Sparks Measurement

Bundles of fibers (4-7 fibers) were manually dissected from extensor digitorus longum (EDL) muscle in a relaxing solution (in mM: K-glutamate 140, HEPES 10, $MgCl_2$ 10, EGTA 0.1, pH=7.0). Bundles were mounted as previously described (Lacampagne et al., 1998) and permeabilized in the relaxing solution containing 0.01% saponin for 30-40 s. The solution was changed to an internal medium (in mM: K-glutamate 140, $Na_2ATP$ 5, glucose 10, HEPES 10, $MgCl_2$ 4.4, EGTA 1.1, $CaCl_2$ 0.3, Fluo-3 0.05 (pentapotassium salt, Tef-labs, USA), pH=7.0) used for image recording.

Fluorescence images were acquired with a Zeiss LSM 510 NLO confocal system (63× oil immersion, NA=1.4, Zeiss, France) operated in line-scan mode (x vs. t, 1.9 ms/line). Fluo-3 was excited with an Argon/Kryton laser at 488 nm and the emitted fluorescence was recorded at ~525 nm. Potential spark areas were empirically identified using an auto-detection algorithm (Cheng et al., 1999). The mean F value for the image was calculated by summing and averaging the temporal F at each spatial location while ignoring potential spark areas. This F value was then used to create a ΔF/F image pixel-by-pixel. Selection and analysis of $Ca^{2+}$ sparks was performed essentially as described by Klein et al. (1997).

Determinations of spatio-temporal properties of individual $Ca^{2+}$ sparks were made on spatial (x) and temporal (t) profiles of sparks centered at the peak amplitude of the $Ca^{2+}$ spark. The ΔF/F amplitude as well as temporal parameters, rise-time (10 to 90% of peak ΔF/F, RT), and duration (full-duration at half-maximum peak amplitude, FDHM) were derived from the temporal profile. The width of the $Ca^{2+}$ spark (full-width at half-maximum peak amplitude, FWHM) was determined from the spatial profile. Statistical comparison of population parameters between the two groups was conducted using a non-parametric Kruskal-Wallis test.

Methods of Transfecting Cells

Methods of transfecting cells with nucleic acid encoding a ryanodine receptor to obtain cells in which the ryanodine receptor is expressed are known in the art (see, for example, Brillantes et al., 1994). In non-muscle cells, the RyR1 receptor is expressed on the endoplasmic reticulum. The cells may be additionally transfected with nucleic acid encoding a beta adrenergic receptor to obtain cells in which both the RyR1 receptor and beta adrenergic receptor are expressed. Such transfected cells may also be used to test compounds and screen compound libraries to obtain compounds which bind receptors as well as compounds which activate or inhibit activation of functional responses in such cells, and therefore are likely to do so in vivo.

A broad variety of host cells can be used to study heterologously expressed proteins. These cells include but are not limited to mammalian cell lines such as, for example, COS-7, Chinese hamster ovary (CHO), LM(tk⁻), HEK293; insect cell lines such as, for example, Sf9, Sf21; amphibian cells such as *Xenopus* oocytes; assorted yeast strains; assorted bacterial cell strains; and others. Culture conditions for each of these cell types are specific and are known to those familiar with the art.

DNA encoding proteins to be studied can be transiently expressed in a variety of mammalian, insect, amphibian, yeast, bacterial and other cells lines by several transfection methods including but not limited to: calcium phosphate-mediated, DEAE-dextran-mediated; liposomal-mediated, viral-mediated, electroporation-mediated, and microinjection delivery. Each of these methods may require optimization of assorted experimental parameters depending on the DNA, cell line, and the type of assay to be subsequently employed.

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin.

Binding Assays

Methods of conducting binding assays are well known in the art. Labeled compounds are placed in contact with intact cells, or a cell extract containing sarcoplasmic reticulum or endoplasmic reticulum, expressing the RyR1 receptor. Methods of preparing a cell extract containing sarcoplasmic reticulum or endoplasmic reticulum are known in the art (e.g., Kaftan et al., 1996). If the compound is labeled with a radioactive isotope such as $^3H$, $^{14}C$, $^{125I}$, $^{35}S$, $^{32}P$, $^{33}P$, the bound compound may be detected by using liquid scintillation counting, scintillation proximity, or any other method of detection for radioactive isotopes. If the compound was labeled with a fluorescent compound, the bound labeled compound may be measured by methods such as, but not restricted to, fluorescence intensity, time resolved fluorescence, fluorescence polarization, fluorescence transfer, or fluorescence correlation spectroscopy. In this manner, compounds that bind to the receptor may be identified as they inhibit the binding of the labeled compound to the receptor.

Assays for Compounds to Treat Defective Skeletal Muscle Function and Heart Disease PKA phosphorylation of RyR1 increases the activity of the RyR1 channel resulting in the release of more calcium into the cytoplasm of the cell for a given activator of the channel. Compounds that block PKA activation of RyR1 would be expected to reduce the activation of the RyR1 channel resulting in less release of calcium into the cell. Compounds that bind to the RyR1 channel at the FKBP12.6 binding site but do not come off the channel when the channel is phosphorylated by PKA would also be expected to decrease the activity of the channel in response to PKA activation or other triggers that activate the RyR1 channel. Such compounds would also result in less calcium release into the cell.

One assay for compounds that may be effective in treating defective skeletal muscle function involves measuring the release of calcium into cells via the RyR1 channel using calcium-sensitive fluorescent dyes (e.g. Fluo-3, Fura-2). The assay involves loading cells with the fluorescent dye and stimulating the cells with a RyR1 activator and determining whether or not a compound added to the cells reduces the calcium-dependent fluorescent signal (Brillantes et al., 1994; Gillo et al, 1993; Jayaraman et al., 1996). One RyR1 activator is caffeine which can be added to the cell. When calcium is released into the cytoplasm of the cell it is bound by the calcium-sensitive dye which then emits a fluorescent signal. Calcium-dependent fluorescent signals are monitored with a photomultiplier tube and analyzed with appropriate software as described by Brillantes et al., 1994; Gillo et al, 1993; and Jayaraman et al., 1996. This assay can be easily automated to screen large numbers of compounds using multiwell dishes. The assay involves expressing recombinant RyR1 channels in a heterologous expression system such as bacterial, yeast, insect, Sf9, HEK293, CHO, COS-7, LM(tk⁻), mouse embryonic fibroblast NIH-3T3, or HeLa cells (Brillantes et al., 1994). In non-muscle cells, the RyR1 receptor is expressed on the endoplasmic reticulum. When the RyR1 channel is activated, calcium is released from the endoplasmic reticulum into the cytoplasm of the cell. RyR1 receptors could be co-expressed with beta adrenergic receptors. This would permit the assessment of compounds on RyR1 receptor activation in response to addition of beta adrenergic receptor agonists.

Another assay involves measuring the level of PKA phosphorylation of RyR1 which can be used to determine the efficacy of compounds designed to block the PKA phosphorylation of the RyR1 channel. This assay can be used in connection with animal models in which heart failure is induced by rapid cardiac pacing. The assay is based on the use of antibodies that are specific for the RyR1 channel protein (anti-RyR1 antibody). For this assay the RyR1 channel protein is immunoprecipitated with the anti-RyR1 antibody and then back-phosphorylated with PKA and [γ-$^{32}$P]-adenosine triphosphate (ATP). The amount of radioactive $^{32}$P label that is transferred to the RyR1 receptor protein can be measured using a phosphorimager. In another version of the assay, the antibody is specific for the phosphorylated form of the RyR1 receptor, in which case back-phosphorylation is not necessary.

Other assays for RyR1 receptor channel function involve measuring the degree of association of the FKBP12.6 binding protein with the RyR2 receptor, the subconductance state of the RyR1 receptor channel, the $Ca^{2+}$ sensitivity for activation of the RyR1 receptor channel, or the open probability ($P_o$) of the RyR1 receptor channel.

FK506 and rapamycin both dissociate FKBP12 from RyR1. One assay involves using FK506-Sepharose or rapamycin-Sepharose columns to screen libraries of compounds looking for ones that bind to the column. Binding can be assessed by washing the columns with binding buffer followed by elution with high salt buffer. Compounds that bind to the columns can be tested for their ability to bind to the skeletal muscle ryanodine receptor (in skeletal muscle membrane preparations) and displace FKBP12 bound to the channel. This competition assay involves incubating the channel with the compound and then centrifugation followed by immunoblotting the pellet versus supernatant. Compounds that bind to the channel and compete off FKBP12 would result in detection of FKBP12 in the supernatant. This could be assayed using 96-well plates with a dot blot apparatus and immunoblotting with anti-FKBP12 antibody.

Compounds that are identified using these assays could be tested for their ability to inhibit isoproterenol-induced intracellular calcium release in cells loaded with calcium sensitive fluorescent dyes (e.g., fluo-3 or fura-2).

Compounds that stabilize binding of FKBP12 to RyR1 could be identified using high throughput ELISA that assays for FKBP12 released into the supernatant in, e.g., 96-well dishes using anti-FKBP12 antibody following PKA phosphorylation of RyR1 with cAMP and ATP. Compounds that prevent release of FKBP12 into the supernatant would be candidates for lead compounds for novel therapeutics that could then be tested in animal models of HF.

RESULTS

Figure 1A:
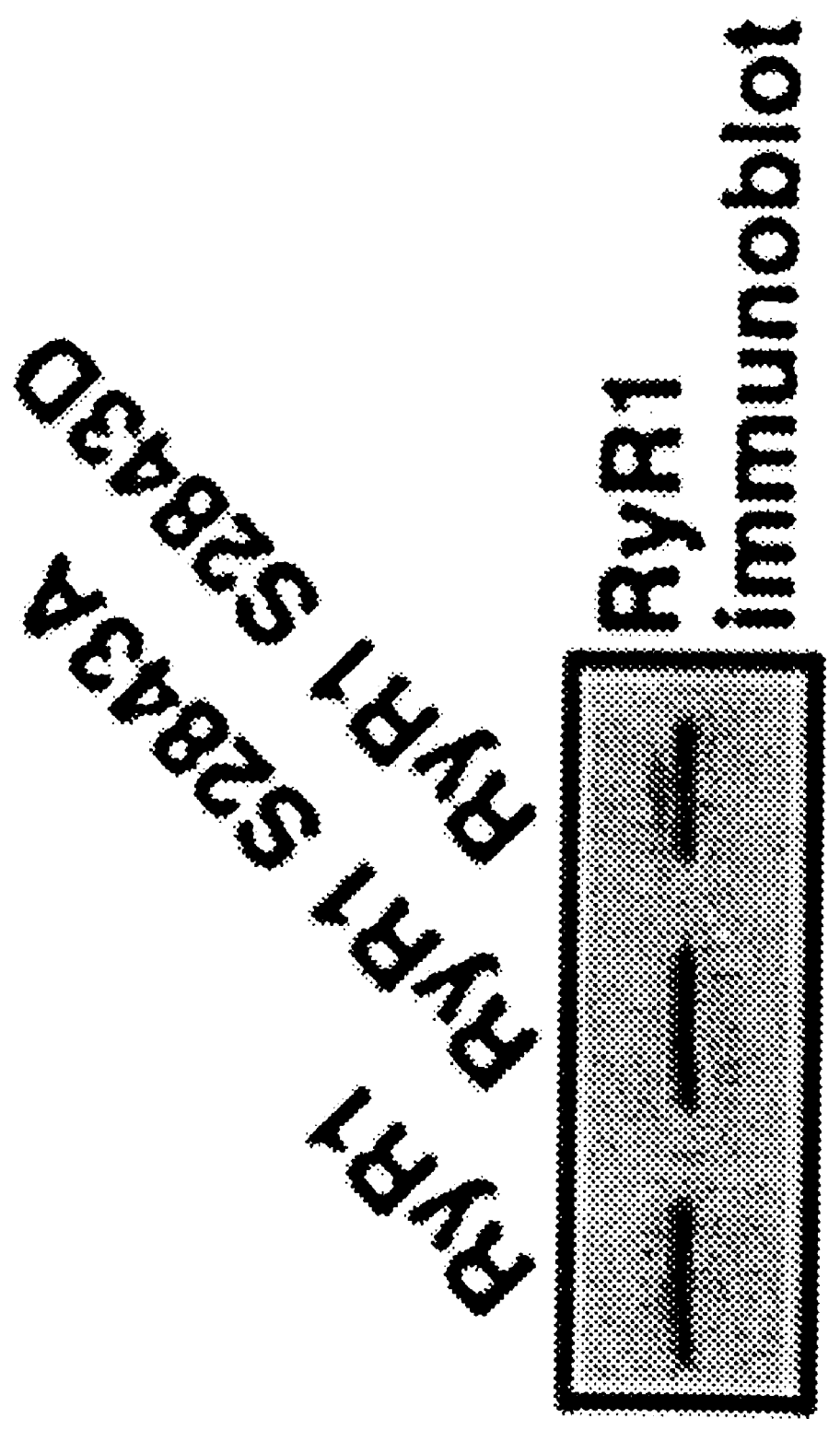
Figure 1B:
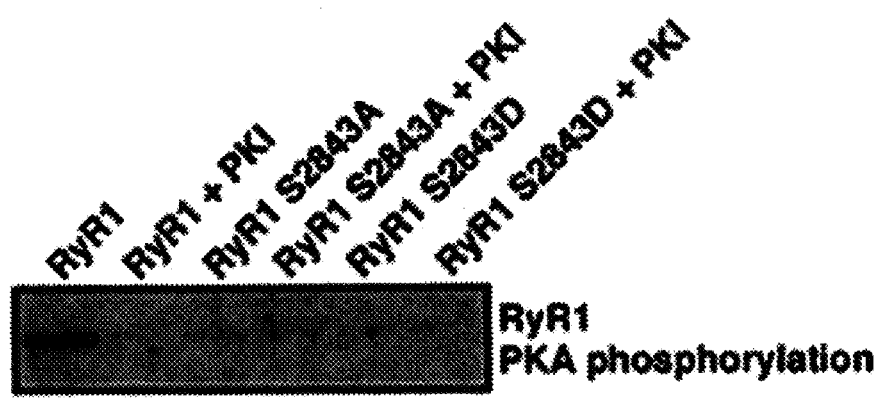
FIGS. 1A-1E. FKBP12 binding to RyR1 is regulated by PKA phosphorylation of RyR1-$Ser^{2843}$. (A) Immunoblot showing that equivalent amounts of WT and mutant (RyR1-S2843A and RyR1-S2843D) RyR1 were expressed in HEK293 cells. (B) Autoradiograph showing PKA phosphorylation of RyR1 using $[\gamma\text{-}^{32}P]$-ATP, the PKA inhibitor, $PKI_{5-24}$, was used to showed specificity of the kinasing reaction. Alanine substitution was used to identify $Ser^{2843}$ as the unique PKA phosphorylation site on RyR1. (C) Immunoblot showing binding of FKBP12 to WT and mutant RyR1 was assessed by centrifugation (FKBP12 co-sediments with RyR1) and FKBP12 immunoblotting. FKBP12 does not bind to RyR1-S2843D which mimics constitutively PKA-phosphorylated RyR1. (D) Autoradiograph showing that activation of PKA bound to RyR1 with cAMP causes phosphorylation of the channel which is inhibited by the PKA inhibitor, $PKI_{5-24}$. Activation of PP1 bound to the channel with protamine causes dephosphorylation of the channel which is blocked by okadaic acid (OA). (E) FKBP12 immunoblot showing that cAMP-induced PKA phosphorylation of RyR1 dissociates FKBP12 from the channel complex; FKBP12 cannot bind to the PKA phosphorylated channel but dephosphorylation of the channel with alkaline phosphatase (or by activating bound phosphatases with protamine) allows subsequent rebinding of FKBP12 to the channel as assessed by co-centrifugation.
Figure 1C:
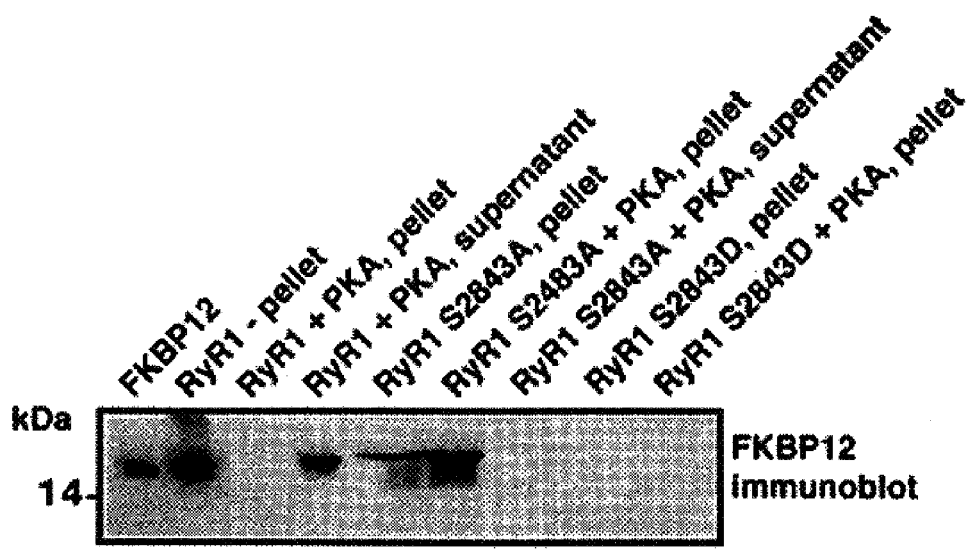

PKA Phosphorylation of $Ser^{2843}$ in RyR1 Regulates FKBP12 Binding and Activates the Channel To understand how RyR1 channels are regulated by PKA phosphorylation, the site of PKA phosphorylation on the channel was first determined using site-directed mutagenesis, and then the effects of PKA phosphorylation of this site on the composition of the RyR1 macromolecular signaling complex were examined (Marx et al., 2001). Alanine (RyR1-S2843A) and aspartic acid (RyR1-S2843D) substitutions were used to identify Ser as the unique PKA phosphorylation site on RyR1 (FIGS. 1A and B). RyR1-S2843A and RyR1-S2843D were expressed in HEK293 cells with the same efficiency as the wild type (WT) RyR1 (FIG. 1A). FKBP12 binding to RyR1 was assessed by co-precipitation (FIG. 1C) as described (Gaburjakova et al., 2001). FKBP12 was detected by immunoblot in the pellet only when bound to RyR1, otherwise, FKBP12 was detected in the supernatant. PKA phosphorylation of RyR1 at $Ser^{2843}$ (homologous to the PKA phosphorylation site on RyR2, $Ser^{2809}$ (Marx et al., 2000)) resulted in the dissociation of FKBP12 from WT RyR1, but not from mutant RyR1-S2843A, which could not be PKA phosphorylated (FIG. 1C). FKBP12 bound to the mutant RyR1-S2483A but not to the mutant RyR1-S2483D, which mimics the constitutively PKA phosphorylated RyR1. These data establish that PKA phosphorylation of RyR1 at $Ser^{2843}$ regulates binding of FKBP12 to the RyR1 channel.

Figure 1D:
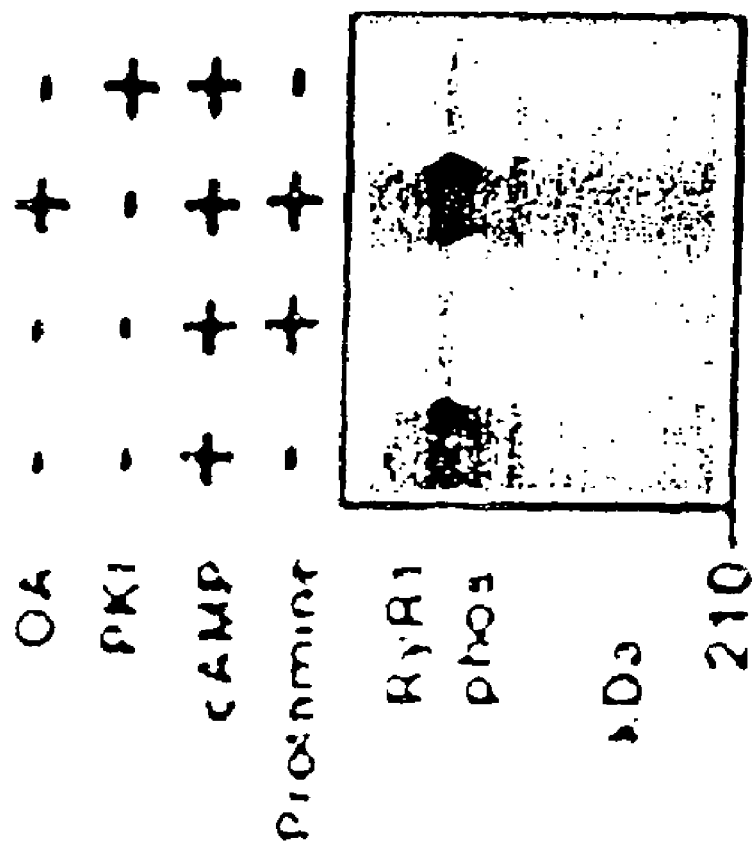

PKA and PP1 were previously shown to be targeted to RyR1 via targeting proteins that bind to highly conserved leucine/isoleucine zipper motifs on the channel (Marx et al., 2001). PKA bound to RyR1 was activated with cAMP (10 µM) causing PKA phosphorylation of RyR1 (FIG. 1D). PP1 bound to RyR1 was activated with protamine (1 mg/ml) causing dephosphorylation of RyR1 (FIG. 1D). Thus, PKA and PP1 in the RyR1 macromolecular complex can regulate phosphorylation/dephosphorylation of the channel without addition of exogenous kinase or phosphatase.

Figure 1E:
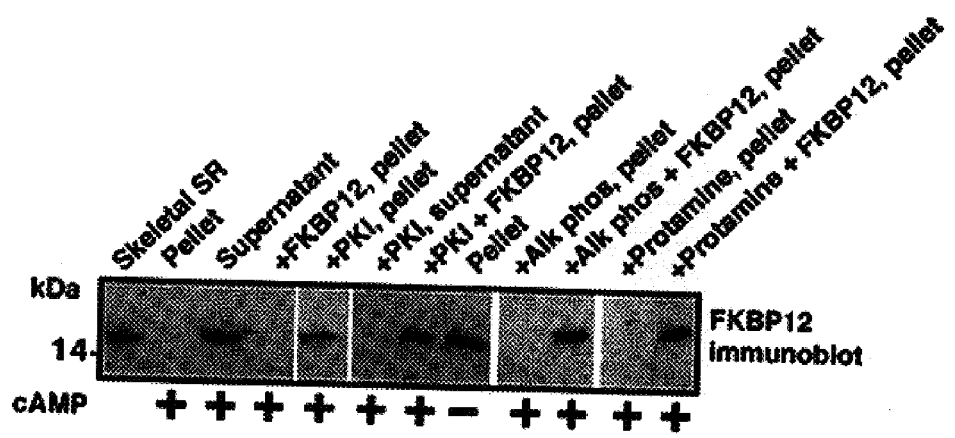

The effects of activation of PKA in the RyR1 macromolecular complex on FKBP12 binding to RyR1 were assessed by co-precipitation (FIG. 1E) as described (Gaburjakova et al., 2001). cAMP-induced PKA phosphorylation of RyR1 caused FKBP12 dissociation from RyR1 (FIG. 1E). Excess FKBP12 could not bind to the PKA phosphorylated RyR1. Inhibiting cAMP-induced activation of bound PKA with $PKI_{5-24}$ (500 nM) blocked phosphorylation-induced dissociation of FKBP12 from RyR1 (FIG. 1E). After PKA-phosphorylated RyR1 was dephosphorylated with alkaline phosphatase (1 unit/mg of SR protein) or by activating bound phosphatase (PP1) with protamine (1 mg/ml), FKBP12 could rebind to the channel (FIG. 1E). Thus, PKA phosphorylation dissociates FKBP12 from RyR1 and FKBP12 cannot rebind to PK-phosphorylated RyR1.

Figures 2A, 2B:
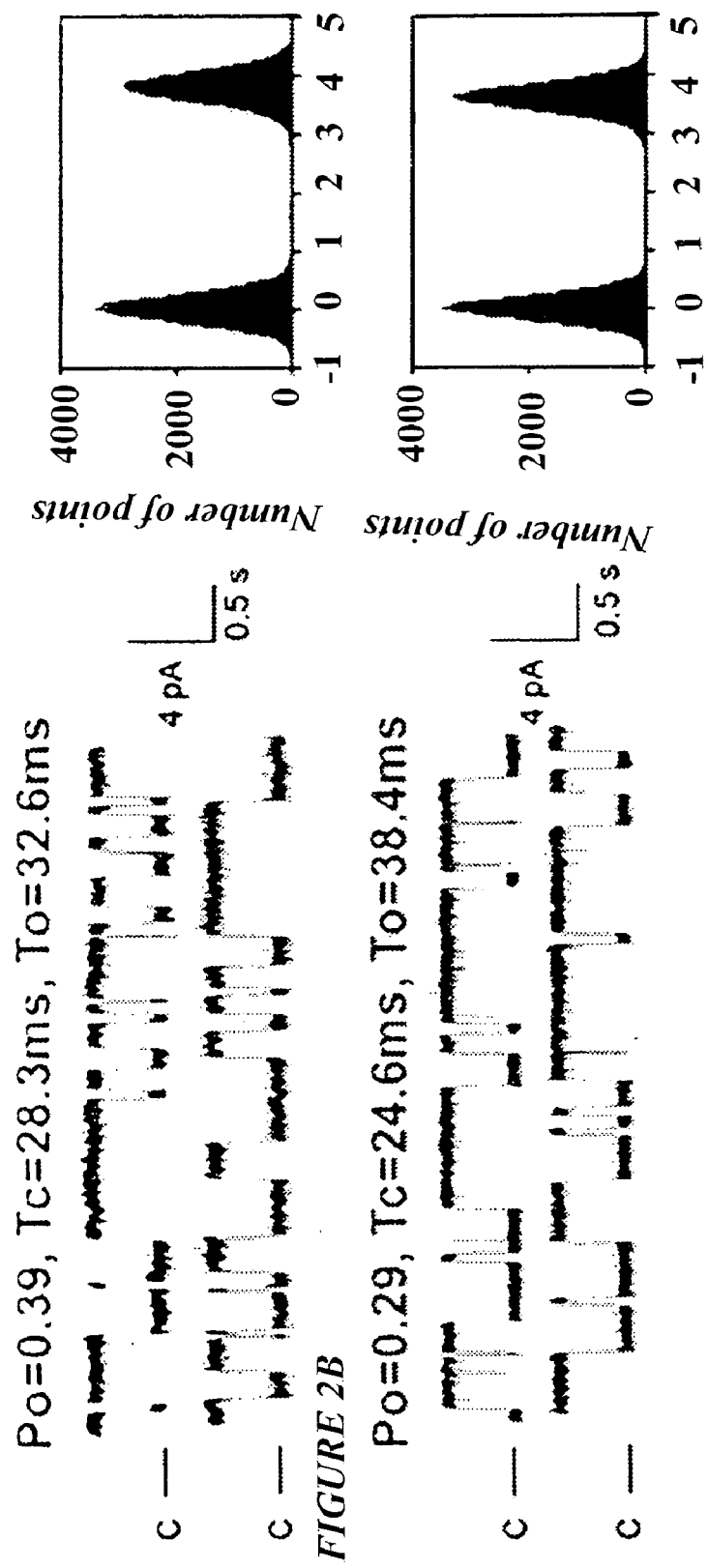
FIGS. 2A-2E. PKA phosphorylation of $Ser^{2843}$ activates RyR1 channels. (A) Representative single channel tracings of WT RyR1; (B) RyR1-S2843A; (C) PKA-phosphorylated WT RyR1; (D) RyR1-S2843D; and (E) RyR1-V2461I (this mutant RyR1 was previously shown to bind FKBP12.6 but not FKBP12 (Gaburjakova et al., 2001)). RyR1 single channel recordings in planar lipid bilayers show activity of the channels at 150 nM $[Ca^{2+}]_{cis}$ in the presence of 1 mM ATP to activate the channels.

To determine the functional effects of PKA phosphorylation of RyR1, RyR1 recombinant channels were expressed in HEK293 cells and reconstituted in planar lipid bilayers to examine their single channel properties (FIG. 2A). Wild type (WT) RyR1 channels (FIG. 2A) were compared to: 1) mutant channels that cannot be PKA-phosphorylated (RyR1-S2843A, FIG. 2B); 2) PKA-phosphorylated WT RyR1 (FIG. 2C); 3) mutant RyR1 that mimic constitutively PKA-phosphorylated RyR1 (RyR1-S2843D, FIG. 2D); and 4) mutant RyR1 that cannot bind FKBP12 (RyR1-S2461I, FIG. 2E). WT RyR1 exhibited the same single channel properties as native RyR1 (FIG. 2A, Table I) as previously reported (Brillantes et al., 1994; Gaburjakova et al., 2001). Mutant RyR1-S2843A also exhibited the same single channel properties as native RyR1 (FIG. 2B).

TABLE I

| | | PKA phosphorylation activates RyR1 | | | | |
|---|---|---|---|---|---|---|
| | | Non-phosphorylated | | | PKA-phosphorylated | |
| | Open probability | Open time (ms) | Closed time (ms) | Open probability | Open time (ms) | Closed time (ms) |
| RyR1 (n = 21) | 0.34 ± 0.1* | 22.1 ± 2.4* | 36.7 ± 3.4* | 0.72 ± 0.1* | 1.6 ± 0.6* | 1.4 ± 0.5* |
| RyR1-S2843A (n = 11) | 0.29 ± 0.1 | 25.1 ± 2.1 | 34.4 ± 2.4 | 0.29 ± 0.1 | 25.1 ± 2.1 | 34.4 ± 2.4 |

TABLE I-continued

PKA phosphorylation activates RyR1

| | Non-phosphorylated | | | PKA-phosphorylated | | |
|---|---|---|---|---|---|---|
| | Open probability | Open time (ms) | Closed time (ms) | Open probability | Open time (ms) | Closed time (ms) |
| RyRl-S2843D (n = 14) | 0.81 ± 0.3** | 1.1 ± 0.3** | 1.9 ± 0.8** | 0.81 ± 0.3 | 1.1 ± 0.3 | 1.9 ± 0.8 |

Figure 2C:
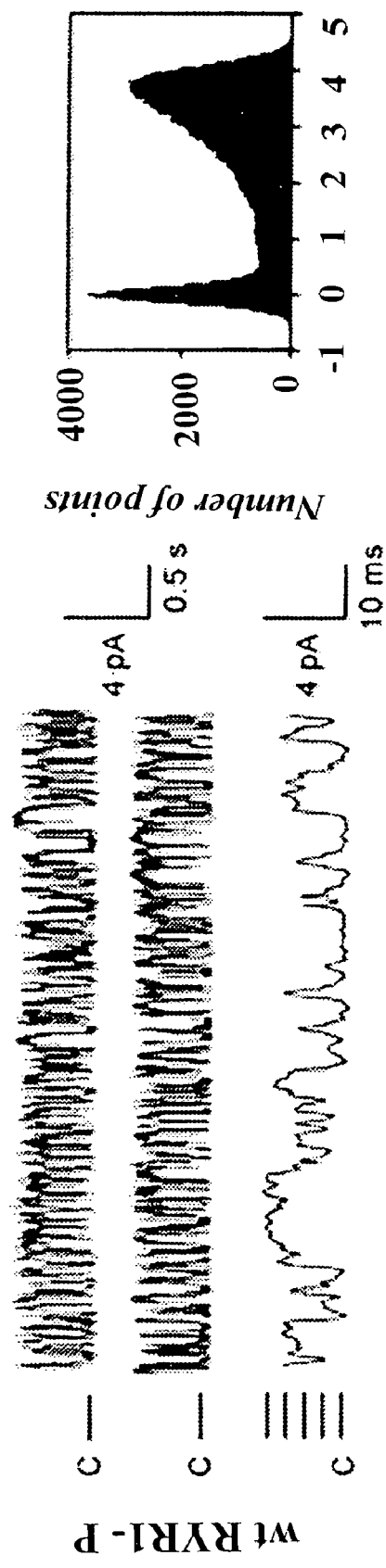
Figure 2D:
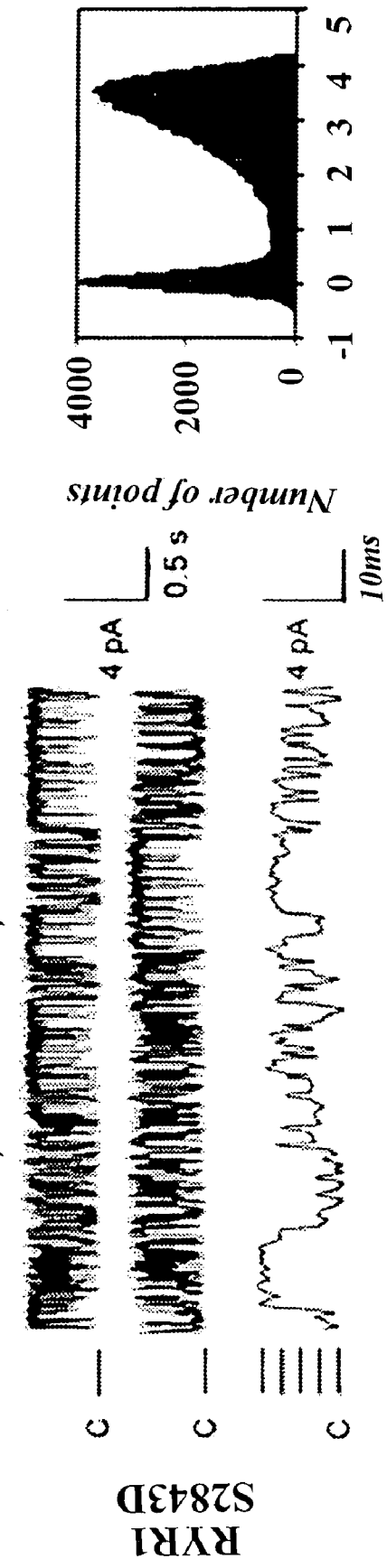
Figure 2E:
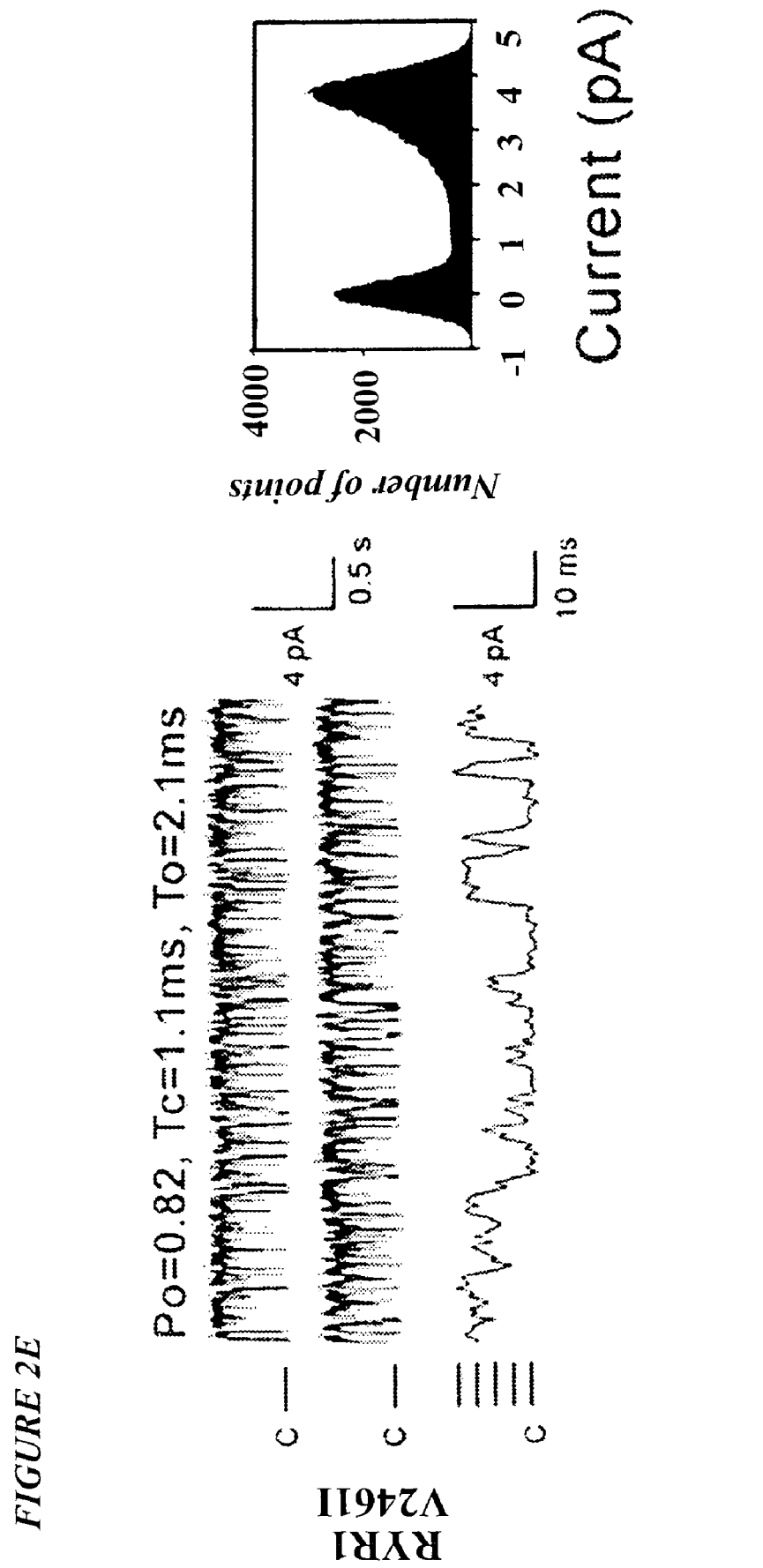

*P < 0.001 for non-phosphorylated vs. PKA-phosphorylated
**P < 0.001 for RyRl-S2843D vs. PKA-phosphorylated WT PKA phosphorylation of RyR1 activated WT RyR1 (increased $P_o$ and decreased open and closed dwell times, FIG. 2C and Table I). PKA phosphorylation of WT RyR1 was confirmed by back-phosphorylation (FIG. 1B). RyR1-S2843A channels could not be activated by PKA (Table I), indicating that activation of WT RyR1 by PKA was due to PKA phosphorylation of RyR1, since the only difference between the WT and mutant RyR1-S843A channels is that the latter cannot be phosphorylated by PKA due to a $Ser^{2843}$Ala substitution. RyR1-S2843D exhibited the same single channel properties as PKA-phosphorylated WT RyR1 (FIG. 2D and Table I), providing additional evidence that the effects of PKA phosphorylation on RyR1 are due to phosphorylation of $Ser^{2843}$. Thus, PKA phosphorylation of RyR1 potently activates the channel at 150 nM cis (cytoplasmic) $[Ca^{2+}]_{cis}$. Since PKA phosphorylation of RyR1 causes dissociation of FKBP12 from the channel (FIG. 1C), it was necessary to determine whether the activation of RyR1 by PKA phosphorylation is due to dissociation of FKBP12 from the channel. To address this question, the single channel properties of RyR1-V2461I, which cannot bind FKBP12 due to a mutation in the FKBP12 binding site (Gaburjakova et al., 2001), were compared to those of PKA-phosphorylated RyR1. RyR1-V2461I exhibited the same changes in single channel properties as PKA-phosphorylated WT RyR1 and the RyR1-S2843D mutant channel, increased $P_o$ and decreased open and closed dwell times compared to non-phosphorylated WT channels (FIG. 2E and Table I).

FKBP12.6 is homologous to FKBP12 and is able to bind to RyR1-V2461I, whereas FKBP12 cannot (Gaburjakova et al., 2001). It was previously shown that the altered single channel properties of the RyR1-V2461I channels, increased $P_o$ and decreased open and closed dwell times, can be restored to normal by FKBP12.6 binding to the channel (Gaburjakova et al., 2001). Thus, the increased $P_o$ and decreased open and closed dwell times exhibited by the RyR1-V2461I mutant channels are specifically due to lack of binding of FKBP12, rather than some undefined effect of the mutation on channel structure or function. Taken together, these data indicate that the activation of RyR1 by PKA phosphorylation at $Ser^{2843}$ is specifically due to dissociation of FKBP12 from the channel.

RyR1 PKA Hyperphosphorylation and Defective Function in HF Skeletal Muscle

To determine whether RyR1 channels from skeletal muscle from animal models of HF (a chronic hyperadrenergic condition) were PKA-hyperphosphorylated and exhibited altered single channel properties, PKA phosphorylation of RyR1 from hind-limb skeletal muscle from a canine model of pacing-induced HF was assessed using immunoprecipitation of RyR1 followed by back-phosphorylation (FIG. 3A) as described previously (Marx et al., 2000). In this canine model of HF, decreased left ventricular (LV) function was documented by hemodynamic assessment showing LV $dP/dt_{max}$ was 3420±105 in controls and 1722.2±322 in HF (mmHg/s, n=4 normal, n=5 HF, P<0.01). RyR1 from HF skeletal muscle were PKA-hyperphosphorylated compared to RyR1 from normal skeletal muscle (FIG. 3A). The stoichiometry of PKA phosphorylation of RyR1 was: normal 0.4+0.2, HF 3.6+0.8 moles phosphate transferred per mole of RyR1 channel (n=4 normal, n=5 HF, P<0.01). Thus, on average 3/4-4/4 PKA phosphorylation sites on each RyR1 channel were phosphorylated in HF skeletal muscle, whereas <1/4 sites per channel was PKA-phosphorylated in RyR1 from normal control skeletal muscle.

It was previously shown that PKA hyperphosphorylation of cardiac RyR2 causes depletion of FKBP12.6 from the channel macromolecular complex resulting in channels with altered gating properties in failing hearts (Marx et al., 2000). In the present application, the levels of FKBP12 in the skeletal muscle RyR1 macromolecular complex were determined for normal and CHF animals using co-immunoprecipitations as previously described (Marx et al., 2000). There was a significant reduction (~3-fold) in the amount of FKBP12 in the RyR1 complex from HF skeletal muscle compared to controls (n=2 control, n=5 HF, P<0.01, FIG. 3B), comparable to the degree of depletion of FKBP12 from the RyR1 complex observed when RyR1 channels from normal skeletal muscle were subjected to in vitro PKA phosphorylation (FIG. 3B). The total amount of cellular FKBP12 (FIG. 6C), as well as the levels of the catalytic subunit of PKA, and the phosphatase PP1 in the RyR1 macromolecular complex were not changed (FIG. 3C). Thus, PKA hyperphosphorylation of RyR1 is associated with depletion of FKBP12 from the channel macromolecular complex in HF skeletal muscle, analogous to the PKA hyperphosphorylation-induced depletion of FKBP12.6 from RyR2 in failing hearts (Marx et al., 2000).

To determine the functional consequences of PKA hyperphosphorylation and depletion of FKBP12 from the RyR1 macromolecular complex in skeletal muscle, the single channel properties of RyR1 isolated from normal and HF skeletal muscle were compared. HF RyR1 channels had increased open probability ($P_o$) at cis (cytosolic) $[Ca^{2+}]$ of 100 nM (e.g., FIGS. 4A and B, and Table II). Normal RyR1 channels are not active at 100 nM $[Ca^{2+}]_{cis}$ (Lai et al., 1989; Layer and Lamb, 1998; Meissner, 1994). HF RyR1 channels exhibited subconductance states or partial openings (Brillantes et al., 1994) that are rarely observed in RyR1 channels from normal skeletal muscle (e.g., FIG. 4B and Table II). Coupled gating between RyR1 channels, a mechanism by which clusters of channels open and close simultaneously (Marx et al., 1998), was markedly reduced in HF skeletal muscle channels compared RyR1 channels from controls (Table II). The mean open and closed dwell times were significantly reduced in HF RyR1 compared to control (e.g., FIGS. 4A and B, and Table II). Increased $P_o$ at submicromolar $[Ca^{2+}]_{cis}$, decreased open and closed dwell times, subconductance openings, and reduced coupled gating are features of recombinant RyR1 expressed without FKBP12 (Brillantes et al., 1994; Marx, 1998) and of native RyR1 after removal of FKBP12 (Ahern et al., 1997; Marx et al., 1998). Moreover, similar defects in RyR1 single channel properties were observed in RyR1 isolated from skeletal muscle from FKBP12 null mice, although these animals die in utero or shortly after birth due to a developmental defect and skeletal muscle function could not be assessed (Shou et al., 1998).

TABLE II

Properties of RyRl channels from normal and heart failure skeletal muscle

| | Channels active at resting $[Ca^{2+}]$ | Channels with substates | Channels exhibiting coupled gating+ | Open time (ms) | Closed time (ms) |
|---|---|---|---|---|---|
| Normal skeletal muscle | 0/53 (0%) | 1/53 (2%) | 6/53 (11%) | 6.8 ± 1.3 | 9.7 ± 1.2 |
| Heart failure skeletal muscle | 16/42 (38%)* | 33/42 (78%)** | 0/42 (0%)** | 1.4 ± 0.3** | 1.2 ± 0.2** |

*P < 0.01 for HF vs. normal skeletal muscle
**P < 0.001 for HF vs. normal skeletal muscle
+It was previously shown that in normal skeletal muscle ~10% of RyRl channels remain physically coupled to one another during isolation and insertion into the bilayer so the level of coupled gating observed in the present study for RyRl from control skeletal muscle is comparable to that in normal non-HF RyRl (Marx et al., 1993).

Altered SR $Ca^{2+}$ Release in HF Skeletal Muscle

To determine whether alterations in the single channel properties of PKA-hyperphosphorylated and FKBP12-depleted RyR1 are associated with altered SR $Ca^{2+}$ release that could contribute to the impaired function in HF skeletal muscle, $Ca^{2+}$ sparks were recorded. $Ca^{2+}$ sparks, representing SR $Ca^{2+}$ release from clusters of individual RyR1, were examined in myotubes from sham-operated control and HF rat skeletal muscles (FIG. 5A). The amplitude of SR $Ca^{2+}$ release (sparks) was significantly reduced in skeletal myotubes from HF muscles with PKA-hyperphosphorylated RyR1. Compared to control the fluorescence measurement of $[Ca^{2+}]$ was reduced from $\Delta F/F=0.92\pm0.02$ (sham-operated control) to 0.76±0.03 in HF (n=6, P<0.01, FIG. 5B). HF skeletal muscle $Ca^{2+}$ sparks also exhibited slower rise-time (control, 3.98±0.14 vs. HF, 4.66±0.21 ms, P<0.05) and prolonged half duration (control, 12.91±0.50 vs. HF, 15.46+ 0.69 ms, P<0.05) (FIG. 5B). Finally, the spatial spread of $Ca^{2+}$ sparks was larger in the HF skeletal muscles (1.65+ 0.03 vs. 1.95±0.09, P<0.05, FIG. 5B). These data show that PKA-hyperphosphorylated RyR1 are associated with SR $Ca^{2+}$ release events that are slower, have lower peak amplitude and last longer than controls.

RyR1 PKA Phosphorylation Correlates with Defective Muscle Function in Heart Failure Skeletal Muscle To assess the physiological consequences of the alterations in skeletal muscle that occur in heart failure, and specifically to determine whether PKA hyperphosphorylation of RyR1 and depletion of FKBP12 from the RyR1 complex are associated with impaired skeletal muscle function, a rodent post-myocardial infarction HF model was used. In this model HF develops over 6 months following myocardial infarction after ligation of the left anterior descending coronary artery. HF was documented with echocardiography showing that fractional shortening was reduced to 41.4±4.7% in HF (n=10) vs. 51.6±5.3% in sham-operated control (n=6, P<0.01); fractional area of contraction was reduced in HF, 39.1±5.1% vs. 68.7±2.4% in control (P<0.01 HF vs. sham-operated control). Hemodynamic measurements also confirmed HF (LVEDP=9.16±5.19 mm Hg for sham operated control (n=6) vs. 18.28±8.56 mm Hg for HF (n=10), P<0.05; dP/dt=5483±1704 mm Hg/s for control vs. 2922±784 mm Hg/s for HF, P<0.01).

Figure 6A:
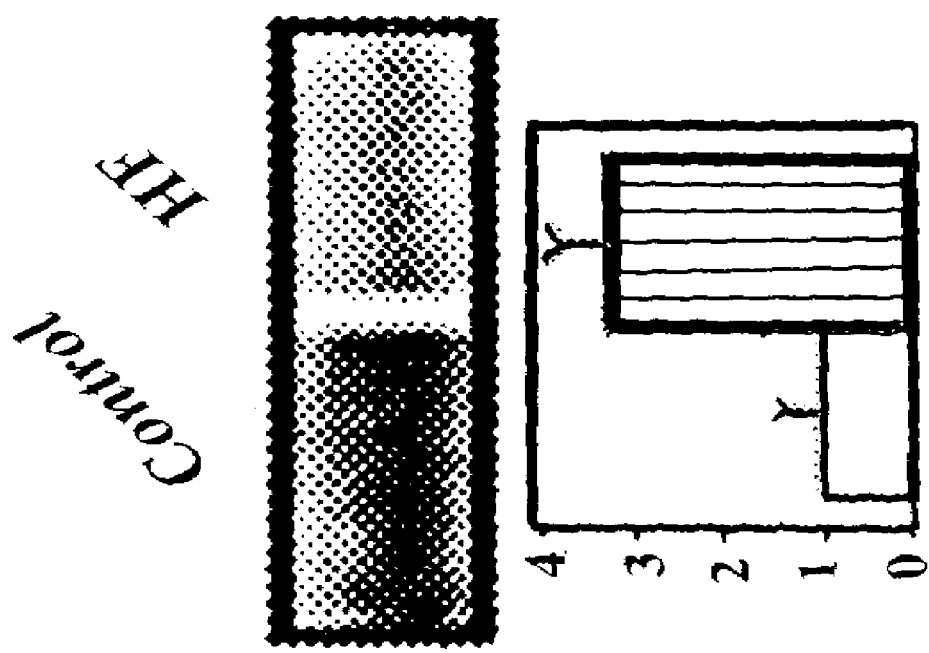
Figure 6B:
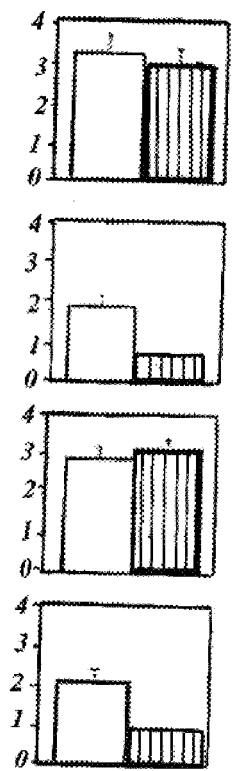
Figure 6C:
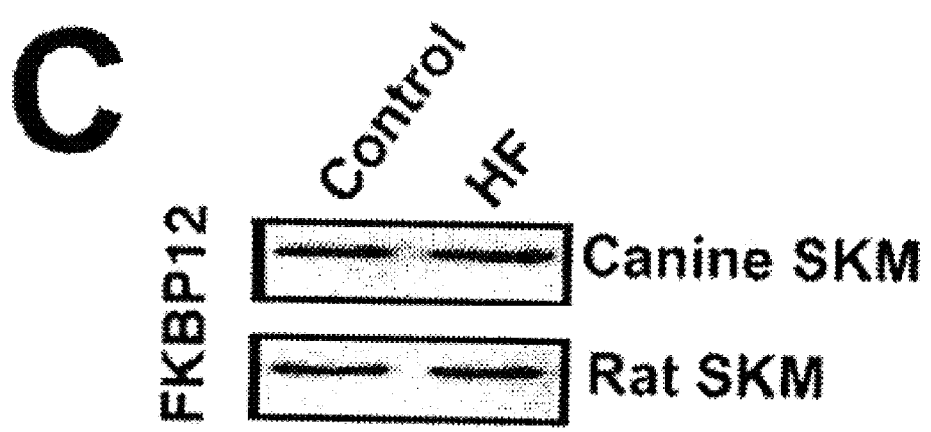
Figure 6D:
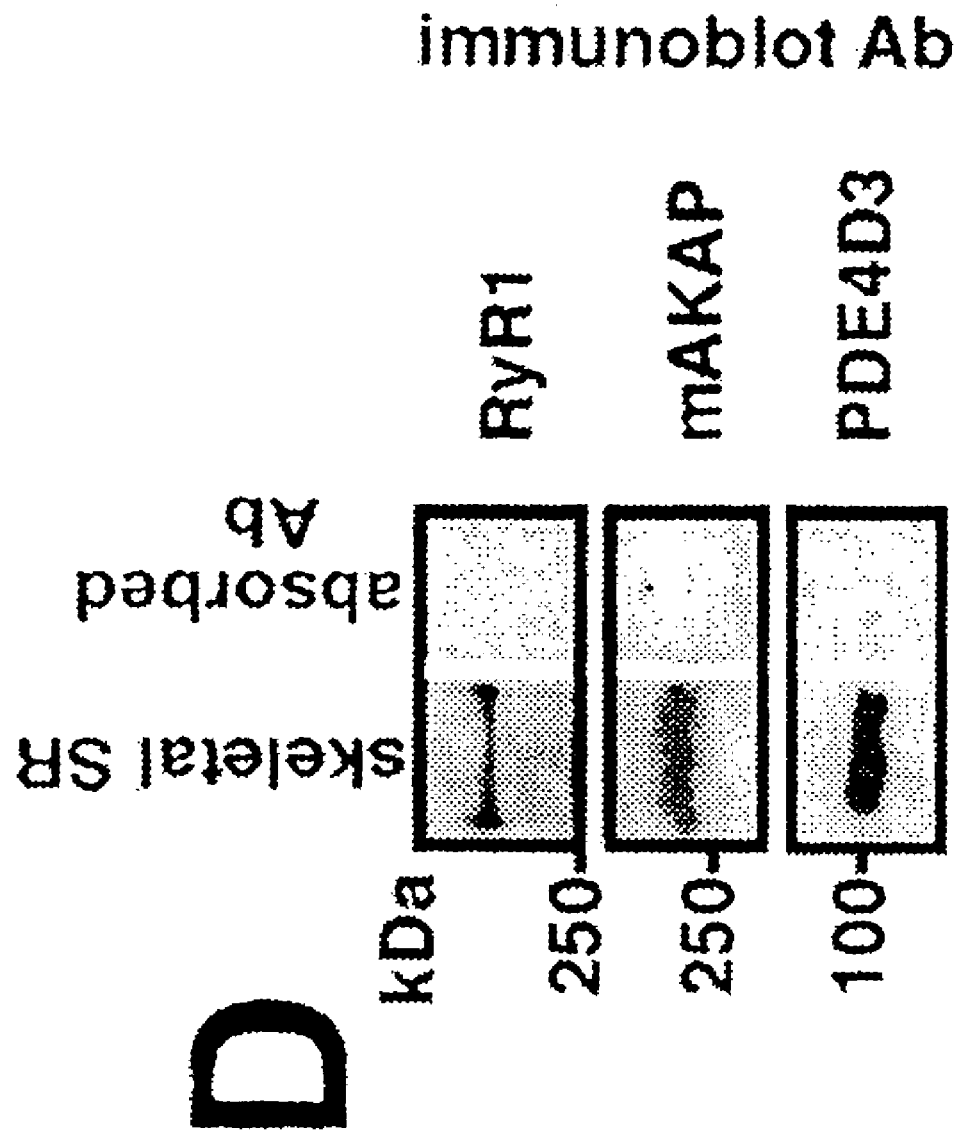

RyR1 channels were PKA-hyperphosphorylated in rat HF skeletal muscle (n=10) compared to sham-operated controls (FIG. 6A, n=6, P<0.01), and the amount of FKBP12 bound to RyR1 was depleted by 58% in the HF skeletal muscle (FIG. 6B, P<0.01), although the total cellular levels of FKBP12 were not decreased in HF skeletal muscle (FIG. 6C). Moreover, in contrast to the cardiac muscle RyR2 macromolecular complex in which PP1 and PP2A levels were decreased in HF providing a potential explanation for the PKA hyperphosphorylation of the RyR2 channel (Marx et al., 2000), the amount of PP1 in the RyR1 complex was not decreased in HF skeletal muscle (FIG. 6B). Recent studies have reported that the phosphodiesterase, PDE4D3, and the targeting protein muscle A-kinase anchoring protein (mAKAP) form a signaling complex along with PKA (Dodge et al., 2001). It had previously been shown that PKA is part of the RyR1 macromolecular complex (Marx et al., 2001), and PKA and mAKAP are components of the RyR2 complex (Marx et al., 2000). To determine whether mAKAP and PDE4D3 were present in the RyR1 macromolecular complex, immunoprecipitation with anti-RyR-5029 followed by immunoblotting with antibodies that detect mAKAP and PDE4D3 (FIG. 6D) was used. It was found that both mAKAP and PDE4D3 co-immunoprecipitate with RyR1 and therefore are likely part of the RyR1 macromolecular complex (FIG. 6B). Moreover, compared to controls (n=4), the amount of PDE4D3 in the RyR1 complex was significantly reduced in HF skeletal muscle (n=4, P<0.05, FIG. 6B). The decreased PDE4D3 levels in the RyR1 channel complex could contribute to a local increase in cAMP and increased PKA activity that may explain PKA hyperphosphorylation of RyR1 in HF skeletal muscle (FIGS. 3A and 6A).

Figure 6E:
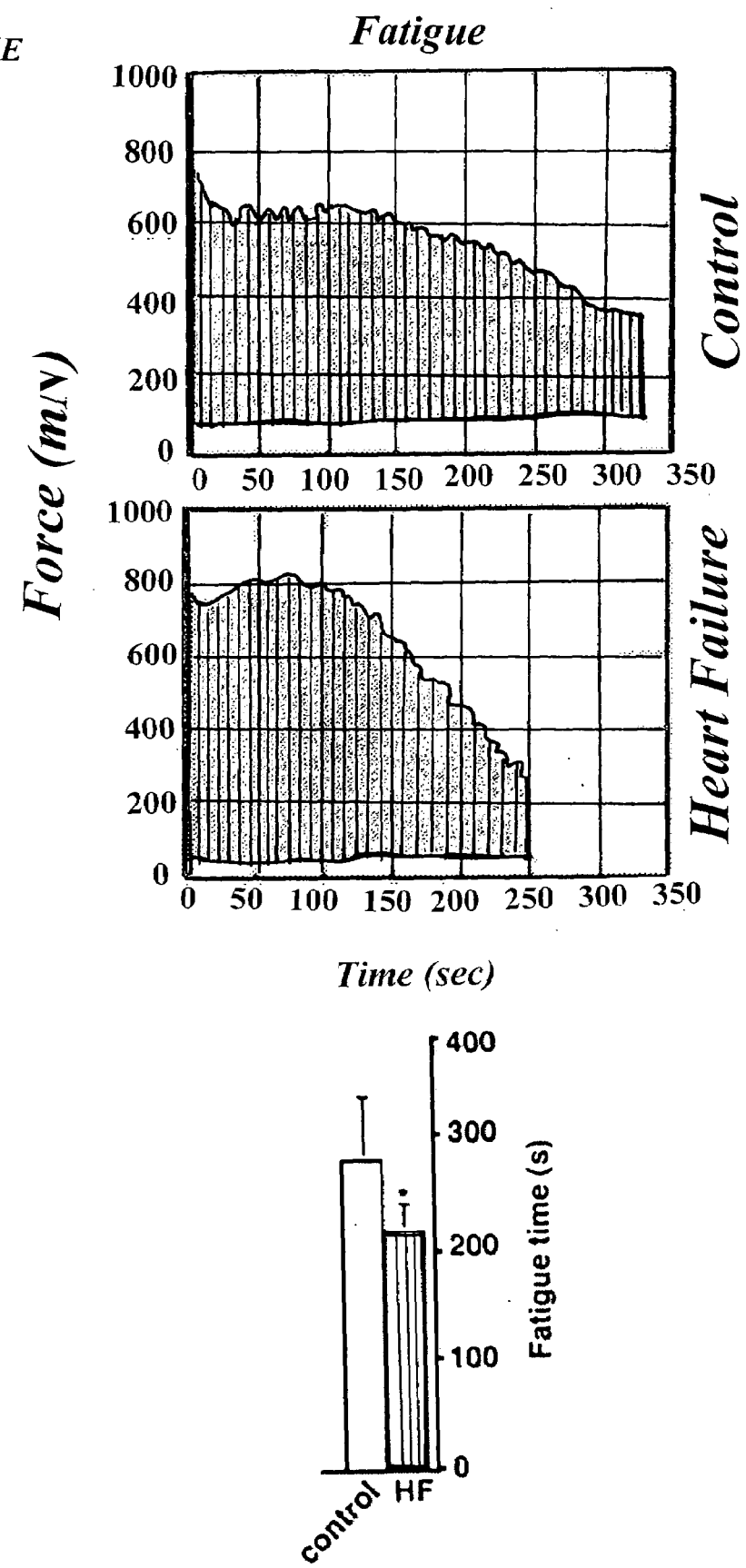

Soleus muscle function was examined using a tension transducer. HF soleus muscles fatigued earlier and reached tetani more slowly than muscle from sham controls (FIGS. 6E and F). The fatigue time was 280±59 sec for control soleus muscle compared to 216±26 sec for HF soleus muscle (n=5 sham operated control, n=8 HF, P<0.05, FIG. 6E). The tetanus half contraction time was 164.6±70.1 ms for control soleus muscle compared to 297.5±74.1 ms for HF soleus muscle (n=5 sham control, n=8 HF, P<0.01, FIG. 6F). The demonstration of defective contractile function including delayed tetani and accelerated fatigue in HF skeletal muscle agrees with the findings of others in both skeletal muscle (Lunde et al., 2001; Lunde et al., 2002; Perreault et al., 1993) and diaphragmatic muscle (MacFarlane et al., 2000). Moreover, the degree of RyR1 PKA hyperphosphorylation correlated significantly with early skeletal muscle fatigue (r=0.88, FIG. 6G). Thus, PKA hyperphosphorylation of RyR1 and depletion of FKBP12 from the RyR1 macromolecular complex are associated with altered skeletal muscle function.

DISCUSSION

Ryanodine receptors (RyR5) are involved in signaling in many types of cells but the physiologic mechanisms that modulate the function of these intracellular $Ca^{2+}$ release channels are not well understood. One of the best understood systems that involve RyR5 is EC coupling in striated muscles where RyR5 are required for SR $Ca^{2+}$ release that activates muscle contraction. However, even in skeletal and cardiac muscles the mechanisms by which systemic signals such as sympathetic nervous system (SNS) modulate RyR function remain to be elucidated.

The "fight or flight" response is a classic stress pathway that involves activation of the SNS leading to β-adrenergic stimulation of muscle. During SNS stimulation catecholamines bind to β-adrenergic receptors, activate adenylyl cyclase via G-proteins and increase the intracellular levels of the second messenger cAMP that activates PKA. The present study shows that PKA phosphorylation activates RyR1 channels by phosphorylating them on $Ser^{2843}$. This PKA phosphorylation site, identified using site-directed mutagenesis (FIGS. 1A and B), agrees with previous studies in which the same site was identified by phosphopeptide mapping (Suko et al., 1993). Identification of the PKA phosphorylation site on RyR1 $Ser^{2343}$ allowed the generation of mutant RyR1 required to probe the mechanism by which PKA phosphorylation activates RyR1 channels.

This approach revealed that PKA phosphorylation activates RyR1 by phosphorylating $Ser^{2843}$ which causes dissociation of FKBP12 from the channel (FIG. 1). The dissociation of FKBP12 relieves an inhibition of channel opening that is due to the stabilization of RyR1 channels in the closed state when FKBP12 is bound.

Figures 2, 5B:
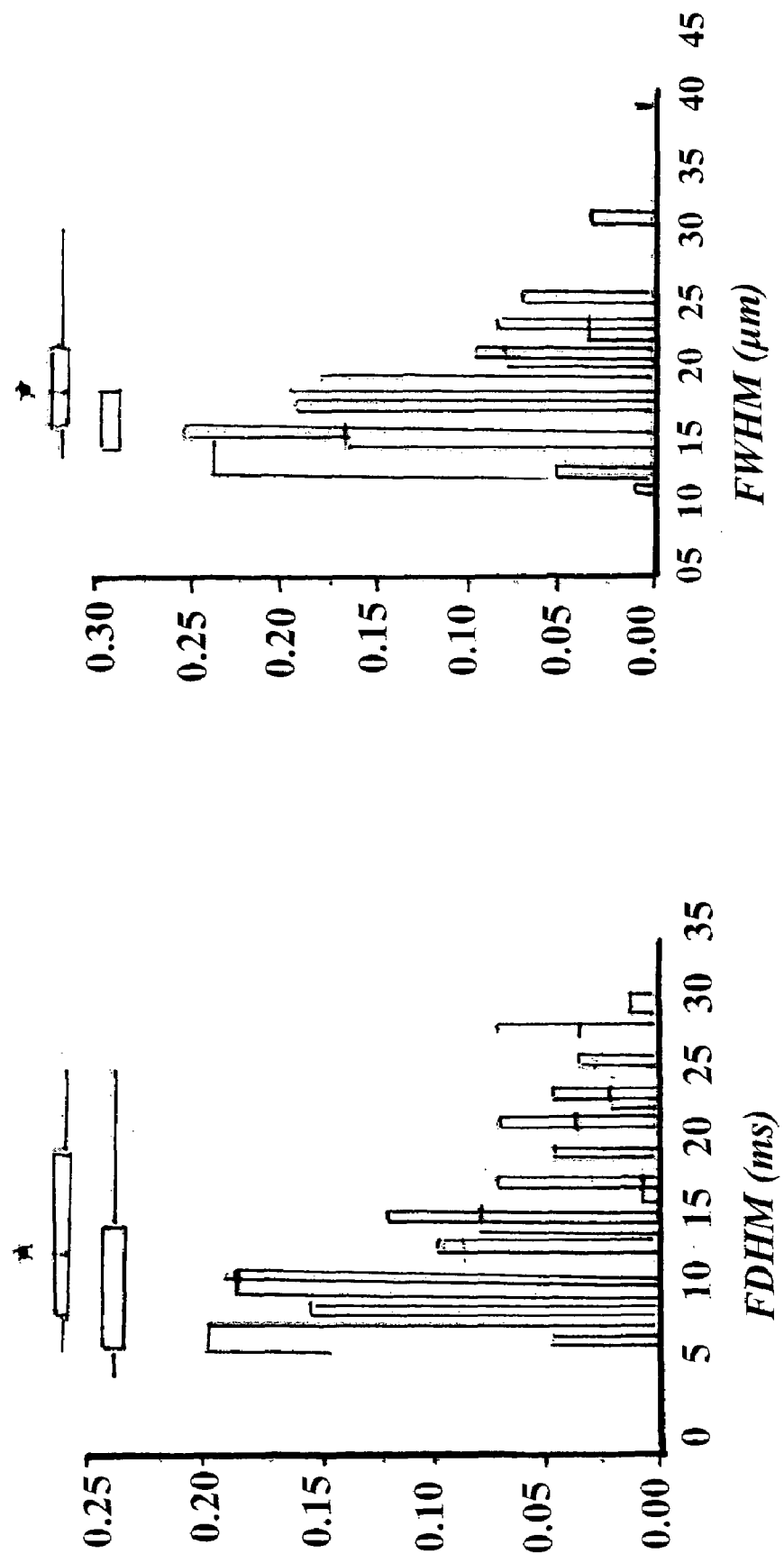

Data from the present study provide novel insights regarding the mechanism by which FKBP12 modulates RyR1 function in the context of skeletal muscle EC coupling. The original studies on the role of FKBP12 in the RyR1 channel complex suggested that this 12 kDa protein was involved in stabilizing RyR1 channels, possibly via binding to the channel and stabilizing it in a favorable conformation that is required for normal physiologic function during EC coupling (Brillantes et al., 1994; Jayaraman et al., 1992). The results of experiments described herein (FIGS. 1 and 2, and Table I) now show that PKA phosphorylation of RyR1 activates the channel by dissociating FKBP12 from the channel complex. This finding suggests that one physiological role of FKBP12 is to stabilize the closed state of the channel, essentially acting as a natural channel inhibitor. By releasing FKBP12 from the channel complex, PKA phosphorylation relieves this inhibition and activates the channel. Thus, PKA phosphorylation of RyR1 provides a physiological mechanism for increasing RyR1 activity in the context of EC coupling. Though the data indicate that FKBP12 stabilizes both the open and closed states of the RyR1, since RyR1 channels are opened via an interaction with the VGCC in skeletal muscle (Ahern et al., 2001; Rios and Brum, 1987; Rios et al., 1992; Schneider and Chandler, 1973; Tanabe et al., 1990), the more important role for FKBP12 in the RyR1 macromolecular complex in skeletal muscle likely is to stabilize the closed state of the channel (i.e., FKBP12 may help keep RyR1 channels closed when muscle is relaxed and prevent SR $Ca^{2+}$ leak in skeletal muscle).

To determine the physiological consequence of the activation of RyR1 by PKA phosphorylation, which is in agreement with previous reports (Hain et al., 1994; Sonnleitner et al., 1997), the function of normal skeletal muscle was compared to those from animal models of HF. HF is a known hyperadrenergic state (Chidsey et al., 1962) and the finding that RyR1 are PKA-hyperphosphorylated in HF skeletal muscle (FIG. 3) provided a model in which to compare the function of muscles with and without PKA-phosphorylated RyR1 in order to probe the role of this form of regulation of RyR1 in skeletal muscle function.

The increased activity of PKA-phosphorylated RyR1 was associated with alterations in SR $Ca^{2+}$ release in HF skeletal muscle. In skeletal muscle, $Ca^{2+}$ sparks represent elementary $Ca^{2+}$ release events arising from a cluster of RyR1 channels (Gonzalez et al., 2000). $Ca^{2+}$ sparks from adult mammalian skeletal muscle have been technically difficult to record (Shirokova et al., 1998), although they have been shown (Kirsch et al., 2001). In the present study, $Ca^{2+}$ sparks exhibited reduced amplitude, slowed rise-time and prolonged duration in HF skeletal muscle (FIG. 5). Depletion of FKBP12 from RyR1 would be expected to increase the probability of SR $Ca^{2+}$ leak because these channels would be destabilized in the closed state. An SR $Ca^{2+}$ leak could deplete SR $Ca^{2+}$ and contribute to reduced amplitude of SR $Ca^{2+}$ release events observed in HF skeletal muscle. In order to record $Ca^{2+}$ sparks the muscle fibers were saponin-skinned and free $[Ca^{2+}]$ was clamped at 130 nM. These conditions likely explain why the spark frequency was not significantly increased in HF skeletal muscle because the overall spark frequency was very low at resting $[Ca^{2+}]$ of 130 nM. Clamping the free $Ca^{2+}$ at 130 nM could also explain why there was not a significant decrease in SR $Ca^{2+}$ content in HF skeletal muscle, measured using acute application of 4-chloro-m-cresol (caffeine analogue), because SR $Ca^{2+}$ ATPase activity combined with the low spark rate in part due to clamping free $Ca^{2+}$ at a low (resting) level would favor refilling the SR. The reduction in RyR1 coupled gating that would accompany FKBP12 depletion from the RyR1 complex (Marx et al., 1998) could contribute to the prolonged time course of SR $Ca^{2+}$ release events in HF skeletal muscle. Coupled gating between RyR1 channels may be a mechanism that enables groups of channels that are physically contacting one another in the SR membrane to open and close as a single $Ca^{2+}$ release unit (Marx et al., 1998). FKBP12 binding to RyR1 is required for coupled gating (Marx et al., 1998). A reduction in coupled gating due to FKBP12 depletion might delay opening of some RyR1 channels in a cluster because they would not all open together as they would with intact coupled gating. This delayed opening of some channels could contribute to the slowed rate of SR $Ca^{2+}$ release. Similarly, under conditions of reduced coupled gating closure of some RyR1 channels might be delayed and this could contribute to the prolonged decay of the SR $Ca^{2+}$ release transient. A model depicting these effects of PKA hyperphosphorylation of RyR1 in HF skeletal muscle is shown in FIG. 7.

Figure 6F:
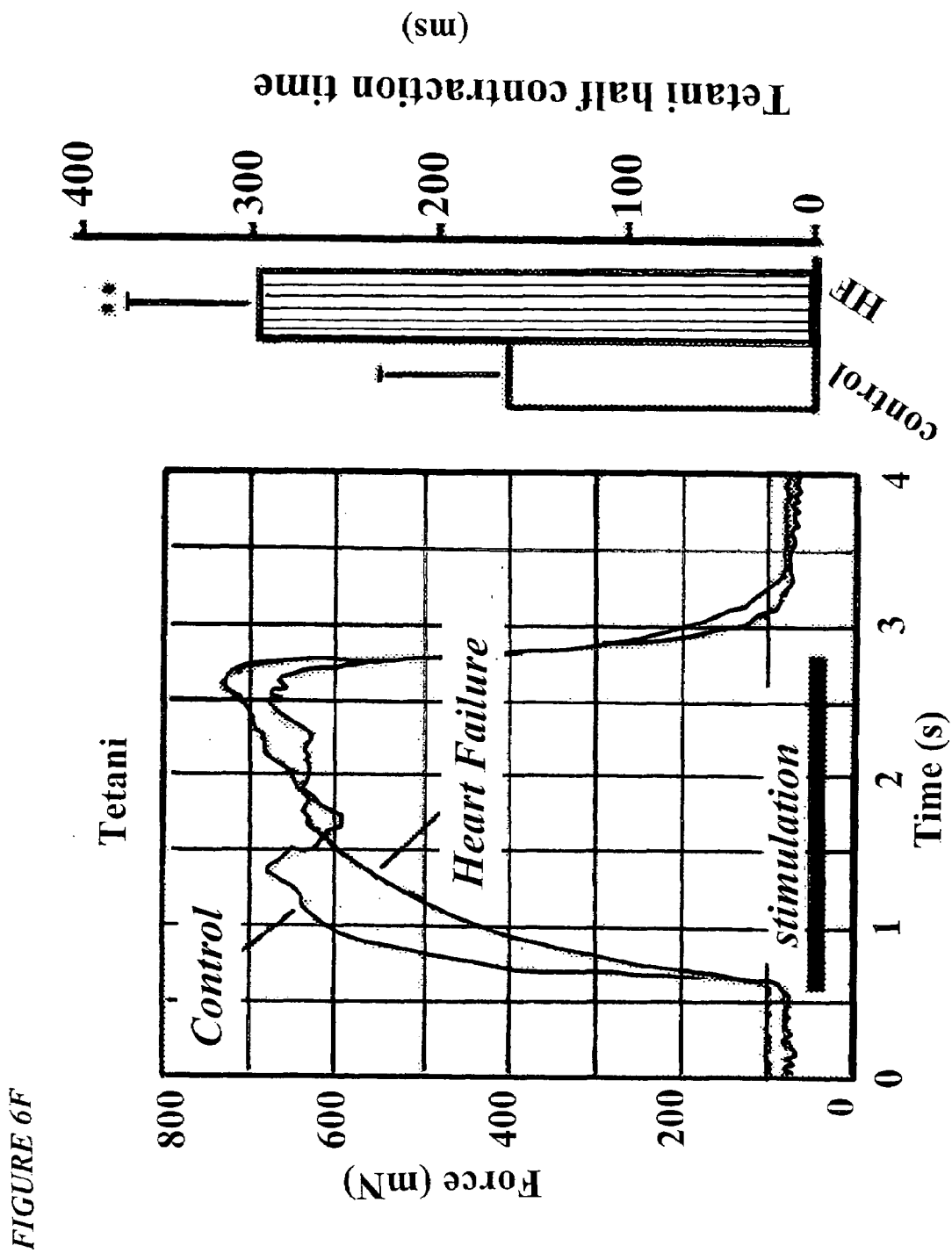
Figure 6G:
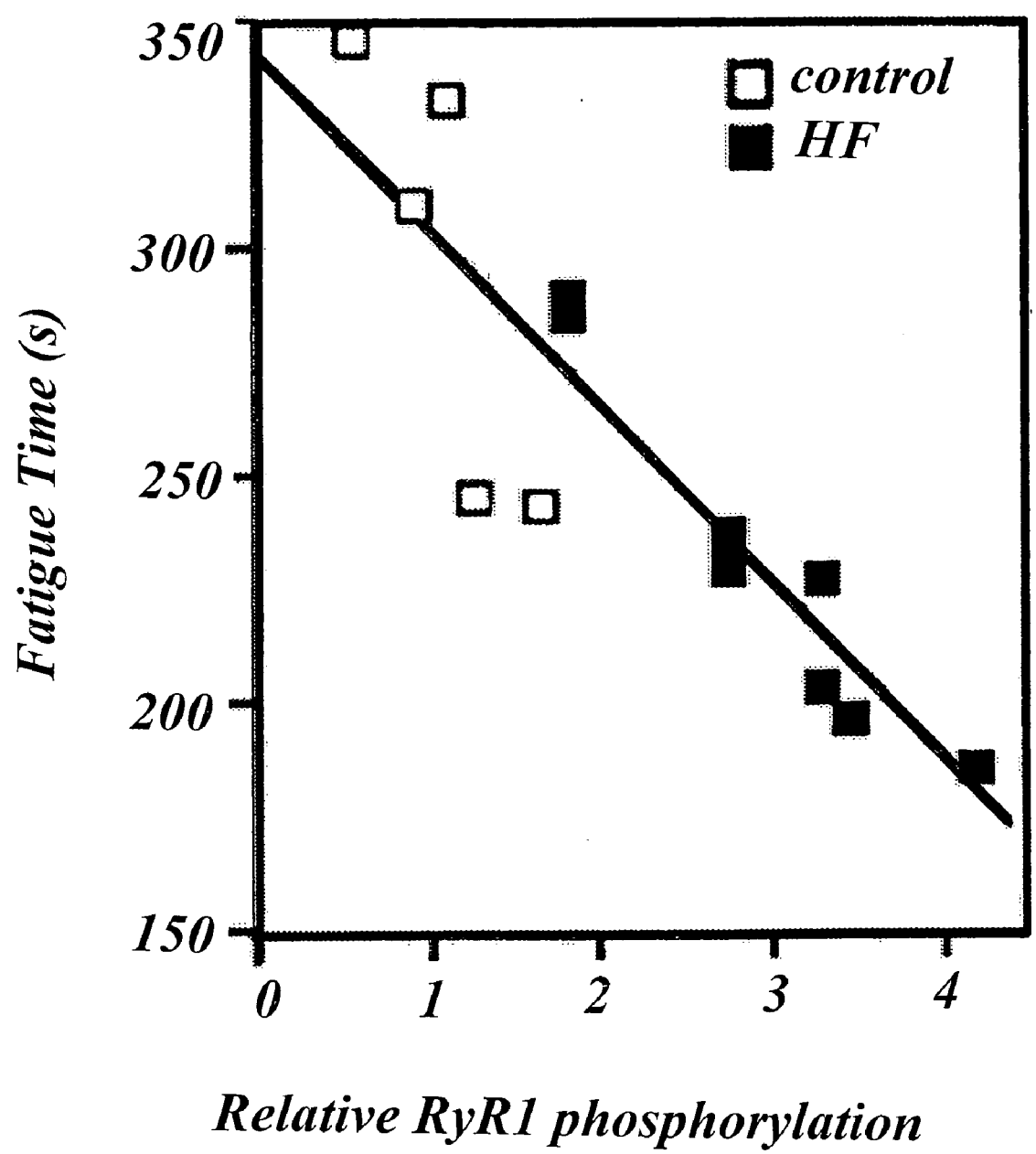
Figure 7A:
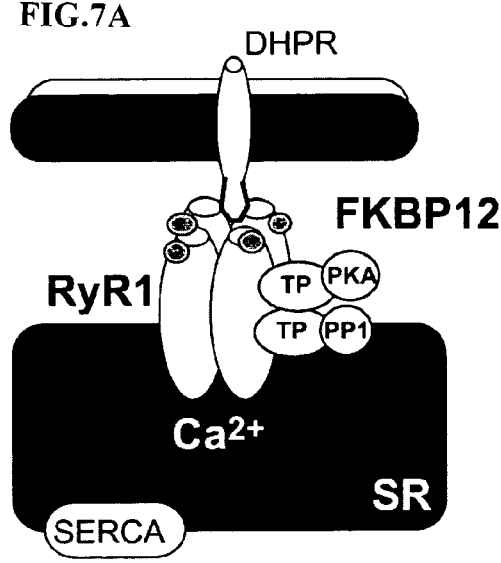
Figure 7F:
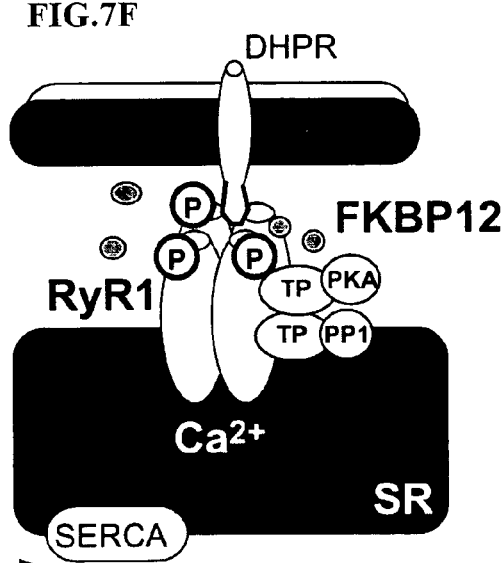
Figure 7B:
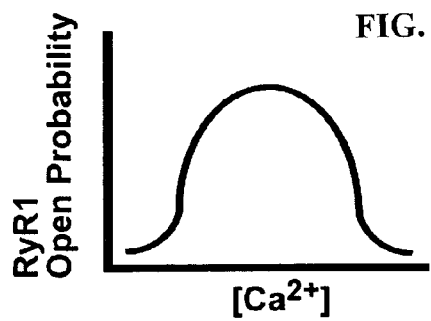
Figure 7G:
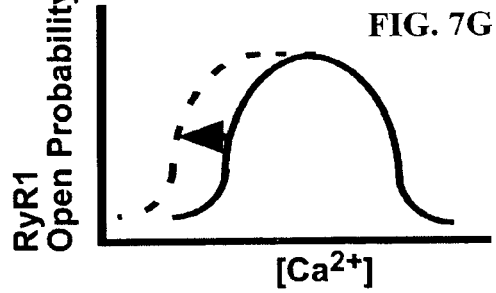
Figure 7C:
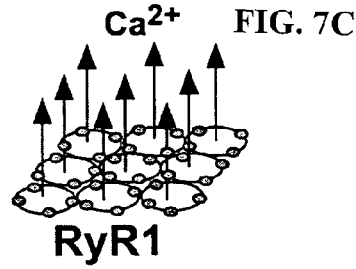
Figure 7H:
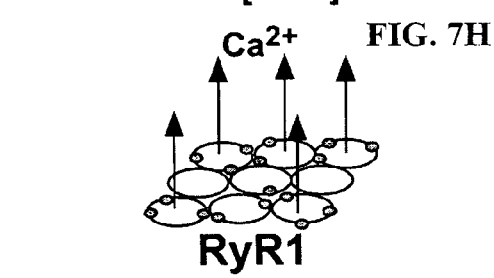
Figure 7D:
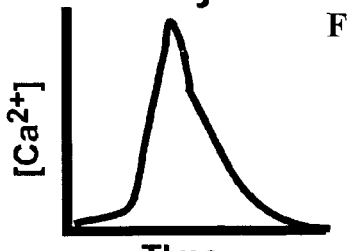
Figure 7I:
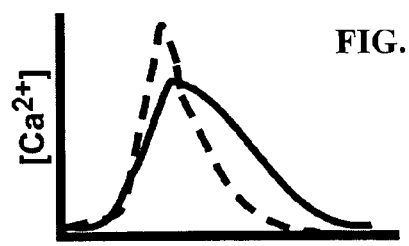
Figure 7E:
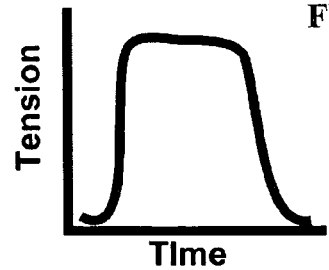
Figure 7J:
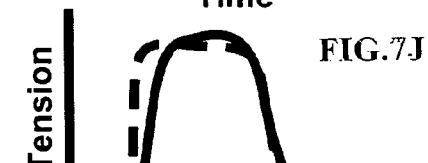

HF skeletal muscles containing PKA hyperphosphorylated RyR1 exhibited prolonged tetani half-contraction times (FIG. 6F). The prolonged tetani half-time (meaning that it takes longer to achieve tetani with the same repetitive stimuli) could reflect impaired EC coupling which may occur due to FKBP12 depletion (Lamb and Stephenson, 1996), although the specific role of FKBP12 in normal skeletal muscle EC coupling remains to be elucidated. The early fatigue in HF skeletal muscle (see FIG. 6E) correlates strongly with increased PKA phosphorylation of RyR1 (FIG. 6G) suggesting a functional association between these two findings. Since there is very little $Ca^{2+}$ entry or extrusion in skeletal myocytes, they must recycle most of the $Ca^{2+}$ required for EC coupling. One cost of compensating for increased SR $Ca^{2+}$ leak due to PKA hyperphosphorylated RyR1 channels that are depleted of FKBP12 in skeletal muscle, may be increased energy consumption (ATP is required to pump $Ca^{2+}$ back into the SR via the $Ca^{2+}$-ATPase; see FIG. 7A) that could contribute to the early fatigue observed in HF skeletal muscle.

The significance of a primary skeletal muscle defect in HF is underscored by the fact that fatigue in patients does not correlate well with cardiac function (Harrington and Coats, 1997). Moreover, the problem with skeletal muscle does not appear to be simply a matter of impaired skeletal muscle blood flow as both administration of angiotensin-converting enzyme inhibitors (Drexler et al., 1989) and cardiac transplantation (Sorensen et al., 1999; Stratton et al., 1994) increase cardiac output and skeletal muscle blood flow but do not improve skeletal muscle function. Many studies have documented alterations in skeletal muscle energy metabolism in HF including increased lactate production and turnover (Katz et al., 1993; Wilson et al., 1993), more rapid breakdown of phosphocreatine, and reduced phosphocreatine re-synthesis (Mancini et al., 1992).

Defects in SR $Ca^{2+}$ release channel function and $Ca^{2+}$ signaling, on the other hand, do provide a mechanism that could underlie the impaired skeletal muscle function in HF. The underlying pathology driving the EC coupling myopathy in both cardiac and skeletal muscles is probably the chronic hyperadrenergic state that leads to defective SR $Ca^{2+}$ release channel (RyR1 and RyR2) function through PKA hyperphosphorylation of both the cardiac and skeletal forms of this channel. Further support for the adverse role of the chronic hyperadrenergic state in HF comes from recent studies showing that β-adrenergic receptor blockers that improve cardiac function in HF reverse the PKA hyperphosphorylation of RyR2 and normalize channel function (Doi et al., 2002; Reiken et al., 2001). While β-blockers do improve cardiac muscle function (e.g., improved ejection fraction), they have been shown to have only modest benefit or none at all in terms of improved exercise tolerance in patients with HF (Gullestad et al., 2001; Kukin et al., 1999). However, as alluded to above, exercise tolerance is not solely determined by skeletal muscle function and likely involves metabolic reserve as well as muscle strength. β-blockers have complex effects on skeletal muscle energy metabolism; for example, propranolol inhibits β-adrenergic-induced activation of both phosphorylase kinase and glycogen synthase (Dietz et al., 1980). Thus, it is possible that beneficial effects of β-blockade in terms of improved skeletal muscle function could be balanced by adverse effects on energy metabolism resulting in only minimal improvement in exercise tolerance.

In view of previous studies (Marx et al., 2000), the data disclosed in this application indicate that HF may be characterized as a generalized EC coupling myopathy that affects both forms of striated muscles, cardiac and skeletal. The underlying pathology that causes this general EC coupling myopathy is likely the chronic hyperadrenergic state that occurs during HF.

REFERENCES

Ahern, C. A., Arikkath, J., Vallejo, P., Gurnett, C. A., Powers, P. A., Campbell, K. P. and Coronado, R. (2001). Intramembrane charge movements and excitation-contraction coupling expressed by two-domain fragments of the $Ca^{2+}$ channel. Proc Natl Acad Sci USA 98, 6935-40.

Ahern, G. P., Junankar, P. R., and Dulhunty, A. F. (1997). Subconductance states in single-channel activity of skeletal muscle ryanodine receptors after removal of FKBP12, Biophys J 72, 146-62.

Antos, C. L., Frey, N., Marx, S. O., Reiken, S., Gaburjakova, M., Richardson, J. A., Marks, A. R., and Olson, E. N. (2001). Dilated cardiomyopathy and sudden death resulting from constitutive activation of protein kinase A, Circ Res 89, 997-1004.

Barbone, A., Holmes, J. W., Heerdt, P. M., The, A. H., Naka, Y., Joshi, N., Daines, M., Marks, A. R., Oz, M. C., and Burkhoff, D. (2001). Comparison of right and left ventricular responses to left ventricular assist device support in patients with severe heart failure: a primary role of mechanical unloading underlying reverse remodeling, Circulation 104, 670-5.

Braunwald, E. B. (1992). Heart Disease, 4th edn (Philadelphia, W. B. Saunders Co).

Brillantes, A. B., Ondrias, K., Scott, A., Kobrinsky, E., Ondriasova, E., Moschella, M. C., Jayaraman, T., Landers, M., Ehrlich, B. E., and Marks, A. R. (1994). Stabilization of calcium release channel (ryanodine receptor) function by FK506-binding protein, Cell 77, 513-23.

Bristow, M. R., Gilbert, E. M., Abraham, W. T., Adams, K. F., Fowler, M. B., Hershberger, R. E., Kubo, S. H., Narahara, K. A., Ingersoll, H., Krueger, S., et al. (1996). Carvedilol produces dose-related improvements in left ventricular function and survival in subjects with chronic heart failure. MOCHA Investigators, Circulation 94, 2807-16.

Bristow, M. R., Ginsburg, R., Minobe, W., Cubicciotti, R. S., Sageman, W. S., Lurie, K., Billingham, M. E., Harrison, D.C., and Stinson, E. B. (1982). Decreased catecholamine sensitivity and beta-adrenergic-receptor density in failing human hearts, N Engl J Med 307, 205-211.

Bundgaard, H. (ed.) (1985) Design of Prodrugs, Elsevier, 1985.

Cameron, A. M., Nucifora, F. C., Jr., Fung, E. T., Livingston, D. J., Aldape, R. A., Ross, C. A., and Snyder, S. H. (1997). FKBP12 binds the inositol 1,4,5-trisphosphate receptor at leucine-proline (1400-1401) and anchors calcineurin to this FK506-like domain, J Biol Chem 272, 27582-8.

Chen, Y. G., Liu, F., and Massague, J. (1997). Mechanism of TGFbeta receptor inhibition by FKBP12, EMBO J 16, 3866-76.

Cheng, H., Song, L. S., Shirokova, N., Gonzalez, A., Lakatta, E. G., Rios, E., and Stern, M. D. (1999). Amplitude distribution of calcium sparks in confocal images: theory and studies with an automatic detection method, Biophys J 76, 606-17.

Chidsey, C. A., Harrison, D. C. and Braunwald, E. (1962). Augmentation of plasma norepinephrine response to exercise in patients with congestive heart failure. New Engl J Med 267, 650.

Dietz, M. R., Chiasson, J. L., Soderling, T. R., and Exton, J. H. (1980). Epinephrine regulation of skeletal muscle glycogen metabolism. Studies utilizing the perfused rat hindlimb preparation, J Biol Chem 255, 2301-7.

Dodge, K. L., Khouangsathiene, S., Kapiloff, M. S., Mouton, R., Hill, E. V., Houslay, M. D., Langeberg, L. K. and Scott, J. D. (2001). mAKAP assembles a protein kinase A/PDE4 phosphodiesterase cAMP signaling module. EMBO J 20, 1921-30.

Doi, M., Yano, M., Kobayashi, S., Kohno, M., Tokuhisa, T., Okuda, S., Suetsugu, M., Hisamatsu, Y., Ohkusa, T., and Matsuzaki, M. (2002). Propranolol prevents the development of heart failure by restoring FKBP12.6-mediated stabilization of ryanodine receptor, Circulation 105, 1374-9.

Drexler, H., Banhardt, U., Meinertz, T., Wollschlager, H., Lehmann, M., and Just, H. (1989). Contrasting peripheral short-term and long-term effects of converting enzyme inhibition in patients with congestive heart failure. A double-blind, placebo-controlled trial, Circulation 79, 491-502.

Franzini-Armstrong, C., and Kish, J. W. (1995). Alternate disposition of tetrads in peripheral couplings of skeletal muscle, Journal of Muscle Research & Cell Motility 16, 319-24.

Gaburjakova, M., Gaburjakova, J., Reiken, S., Huang, F., Marx, S. O., Rosemblit, N., and Marks, A. R. (2001). FKBP12 binding modulates ryanodine receptor channel gating, J Biol Chem 276, 16931-5.

Gillo, B., Ma, Y. S. and Marks, A. R. (1993). Calcium entry during induced differentiation in Murine erythroleukemia cells, Blood 81, 783-792.

Gonzalez, A., Kirsch, W. G., Shirokova, N., Pizarro, G., Brum, G., Pessah, I. N., Stern, M. D., Cheng, H., and Rios, E. (2000). Involvement of multiple intracellular release channels in calcium sparks of skeletal muscle, Proc Natl Acad Sci USA 97, 4380-4385.

Gullestad, L., Manhenke, C., Aarsland, T., Skardal, R., Fagertun, H., Wikstrand, J., and Kjekshus, J. (2001). Effect of metoprolol CR/XL on exercise tolerance in chronic heart failure—a substudy to the MERIT-HF trial, Eur J Heart Fail 3, 463-8.

Hain, J., Nath, S., Mayrleitner, M., Fleischer, S., and Schindler, H. (1994). Phosphorylation modulates the function of the calcium release channel of sarcoplasmic reticulum from skeletal muscle, Biophys J 67, 1823-33.

Harrington, D., and Coats, A. J. (1997). Mechanisms of exercise intolerance in congestive heart failure, Current Opinion in Cardiology 12, 224-32.

Jayaraman, T., Brillantes, A.-M. B., Timerman, A. P., Erdjument-Bromage, H., Fleischer, S., Tempst, P., and Marks, A. R. (1992). FK506 Binding Protein Associated with the Calcium Release Channel (Ryanodine Receptor), J Biol Chem 267, 9474-7.

Jayaraman, T., Ondrias, K., Ondriasova, E. and Marks, A. R. (1996). Regulation of the inositol 1,4,5-trisphosphate receptor by tyrosine phosphorylation, Science 272, 1492-4.

Kaftan, E., Marks, A. R., and Ehrlich, B. E. (1996). Effects of rapamycin on ryanodine receptor/$Ca^{2+}$-release channels from cardiac muscle, Circ Res 78, 990-7.

Katz, S. D., Bleiberg, B., Wexler, J., Bhargava, K., Steinberg, J. J., and LeJemtel, T. H. (1993). Lactate turnover at rest and during submaximal exercise in patients with heart failure, J Appl Physiol 75, 1974-9.

Kirsch, W. G., Uttenweiler, D., and Fink, R. H. (2001). Spark- and ember-like elementary $Ca^{2+}$ release events in skinned fibres of adult mammalian skeletal muscle, J Physiol 537, 379-89.

Klein, M. G., Lacampagne, A., and Schneider, M. F. (1997). Voltage dependence of the pattern and frequency of discrete $Ca^{2+}$ release events after brief repriming in frog skeletal muscle, Proc Natl Acad Sci USA 94, 11061-6.

Kukin, M. L., Kalman, J., Charney, R. H., Levy, D. K., Buchholz-Varley, C., Ocampo, O. N., and Eng, C. (1999). Prospective, randomized comparison of effect of long-term treatment with metoprolol or carvedilol on symptoms, exercise, ejection fraction, and oxidative stress in heart failure, Circulation 99, 2645-51.

Lacampagne, A., Klein, M. G., and Schneider, M. F. (1998). Modulation of the frequency of spontaneous sarcoplasmic reticulum $Ca^{2+}$ release events ($Ca^{2+}$ sparks) by myoplasmic [Mg2+] in frog skeletal muscle, J Gen Physiol 111, 207-24.

Lai, F. A., Misra, M., Xu, L., Smith, H. A., and Meissner, G. (1989). The ryanodine receptor-$Ca^{2+}$ release channel complex of skeletal muscle sarcoplasmic reticulum. Evidence for a cooperatively coupled, negatively charged homotetramer, J Biol Chem 264, 16776-85.

Lamb, G. D., and Stephenson, D. G. (1996). Effects of FK506 and rapamycin on excitation-contraction coupling in skeletal muscle fibres of the rat. J Phys 494, 569-76.

Layer, D. R., and Lamb, G. D. (1998). Inactivation of Ca2+ release channels (ryanodine receptors RyR1 and RyR2) with rapid steps in [$Ca^{2+}$] and voltage, Biophys J 74, 2352-64.

Lunde, P. K., Dahlstedt, A. J., Bruton, J. D., Lannergren, J., Thoren, P., Sejersted, O. M., and Westerblad, H. (2001). Contraction and intracellular $Ca^{2+}$ handling in isolated skeletal muscle of rats with congestive heart failure, Circ Res 88, 1299-305.

Lunde, P. K., Verburg, E., Eriksen, M., and Sejersted, O. M. (2002). Contractile properties of in situ perfused skeletal muscles from rats with congestive heart failure, J Physiol 540, 571-80.

MacFarlane, N. G., Darnley, G. M., and Smith, G. L. (2000). Cellular basis for contractile dysfunction in the diaphragm from a rabbit infarct model of heart failure, Am J Physiol Cell Physiol 278, C739-46.

Mancini, D. M., Walter, G., Reichek, N., Lenkinski, R., McCully, K. K., Mullen, J. L., and Wilson, J. R. (1992). Contribution of skeletal muscle atrophy to exercise intolerance and altered muscle metabolism in heart failure, Circulation 85, 1364-73.

Marks, A. R. (1996). Cellular functions of immunophilins, Physiol Rev 76, 631-49.

Marks, A. R., Reiken, S., and Marx, S. O. (2002). Progression of heart failure: is protein kinase a hyperphosphorylation of the ryanodine receptor a contributing factor? Circulation 105, 272-5.

Marx, S. O., Ondrias, K., and Marks, A. R. (1998). Coupled gating between individual skeletal muscle $Ca^{2+}$ release channels (ryanodine receptors), Science 281, 818-21.

Marx, S. O., Reiken, S., Hisamatsu, Y., Gaburjakova, M., Gaburjakova, J., Yang, Y. M., Rosemblit, N., and Marks, A. R. (2001). Phosphorylation-dependent Regulation of Ryanodine Receptors. A novel role for leucine/isoleucine zippers, J Cell Biol 153, 699-708.

Marx, S. O., Reiken, S., Hisamatsu, Y., Jayaraman, T., Burkhoff, D., Rosemblit, N., and Marks, A. R. (2000). PKA Phosphorylation Dissociates FKBP12.6 from the Calcium Release Channel (Ryanodine Receptor): Defective Regulation in Failing Hearts, Cell 101, 365-76.

Meissner, G. (1994). Ryanodine receptor/Ca2+ release channels and their regulation by endogenous effectors, Annu Rev Physiol 56, 485-508.

Minotti, J. R., Christoph, I., Oka, R., Weiner, M. W., Wells, L., and Massie, B. M. (1991). Impaired skeletal muscle function in patients with congestive heart failure. Relationship to systemic exercise performance, J Clin Invest 88, 2077-82.

Ono, K., Yano, M., Ohkusa, T., Kohno, M., Hisaoka, T., Tanigawa, T., Kobayashi, S., and Matsuzaki, M. (2000). Altered interaction of FKBP12.6 with ryanodine receptor as a cause of abnormal $Ca^{(2+)}$ release in heart failure, Cardiovasc Res 48, 323-31.

Perreault, C. L., Gonzalez-Serratos, H., Litwin, S. E., Sun, X., Franzini-Armstrong, C., and Morgan, J. P. (1993). Alterations in contractility and intracellular $Ca^{2+}$transients in isolated bundles of skeletal muscle fibers from rats with chronic heart failure, Circ Res 73, 405-12.

Reiken, S., Gaburjakova, M., Gaburjakova, J., He, K. L., Prieto, A., Becker, E., Yi, G. H., Wang, J., Burkhoff, D., and Marks, A. R. (2001). Beta-adrenergic receptor blockers restore cardiac calcium release channel (ryanodine receptor) structure and function in heart failure, Circulation 104, 2843-8.

Rios, E., and Brum, G. (1987). Involvement of dihydropyridine receptors in excitation-contraction coupling in skeletal muscle. Nature 325, 717-20.

Rios, E., Pizarro, G. and Stefani, E. (1992). Charge movement and the nature of signal transduction in skeletal muscle excitation-contraction coupling. Annu Rev Physiol 54, 109-33.

Schneider, M. F., and Chandler, W. K. (1973). Voltage dependent charge movement in skeletal muscle: a possible step in excitation-contraction coupling, Nature 242, 244-6.

Schoenmakers, T. J., Visser, G. J., Flik, G. and Theuvenet, A. P. (1992). CHELATOR: an improved method for computing metal ion concentrations in physiological solutions. Biotechniques 12, 870-4, 876-9.

Semsarian, C., Ahmad, I., Giewat, M., Georgakopoulos, D., Schmitt, J. P., McConnell, B. K., Reiken, S., Mende, U., Marks, A. R., Kass, D. A., et al. (2002). The L-type calcium channel inhibitor diltiazem prevents cardiomyopathy in a mouse model, J Clin Invest 109, 1013-20.

Shirokova, N., Garcia, J. and Rios, E. (1998). Local calcium release in mammalian skeletal muscle. J Physiol 512, 377-84.

Shou, W., Aghdasi, B., Armstrong, D. L., Guo, Q., Bao, S., Charng, M. J., Mathews, L. M., Schneider, M. D., Hamilton, S. L., and Matzuk, M. M. (1998). Cardiac defects and altered ryanodine receptor function in mice lacking FKBP12, Nature 391, 489-92.

Sonnleitner, A., Fleischer, S., and Schindler, H. (1997). Gating of the skeletal calcium release channel by ATP is inhibited by protein phosphatase 1 but not by $Mg^{2+}$, Cell Calcium 21, 283-90.

Sorensen, V. B., Wroblewski, H., Galatius, S., Haunso, S., and Kastrup, J. (1999). Exercise blood flow and microvascualr distensibility in skeletal muscle normalize after heart transplantation, Clin Transplant 13, 410-9.

Stratton, J. R., Kemp, G. J., Daly, R. C., Yacoub, M., and Rajagopalan, B. (1994). Effects of cardiac transplantation on bioenergetic abnormalities of skeletal muscle in congestive heart failure, Circulation 89, 1624-31.

Suko, J., Maurer-Fogy, I., Plank, B., Bertel, O., Wyskovsky, W., Hohenegger, M. and Hellmann, G. (1993). Phosphorylation of serine 2843 in ryanodine receptor-calcium release channel of skeletal muscle by cAMP-, cGMP- and CaM-dependent protein kinase. Bioch Biophys Acta 1175, 193-206.

Sullivan, M. J., and Hawthorne, M. H. (1995). Exercise intolerance in patients with chronic heart failure, Prog Cardiovasc Dis 38, 1-22.

Tanabe, T., Beam, K. G., Adams, B. A., Niidome, T. and Numa, S. (1990). Regions of the skeletal muscle dihydropyridine receptor critical for excitation-contraction coupling. Nature 346, 567-69.

Wang, J., Yi, G. H., Knecht, M., Cai, B. L., Poposkis, S., Packer, M., and Burkhoff, D. (1997). Physical training alters the pathogenesis of pacing-induced heart failure through endothelium-mediated mechanisms in awake dogs, Circulation 96, 2683-92.

Wilson, J. R. (1995). Exercise intolerance in heart failure. Importance of skeletal muscle, Circulation 91, 559-61.

Wilson, J. R., Mancini, D. M., and Dunkman, W. B. (1993). Exertional fatigue due to skeletal muscle dysfunction in patients with heart failure, Circulation 87, 470-5.

Yano, M., Kobayashi, S., Kohno, M., Doi, M., Tokuhisa, T., Okuda, S., Suetsugu, M., Hisaoka, T., Obayashi, M., Ohkusa, T., Kohno, M. and Matsuzaki, M. (2003). FKBP12.6-mediated stabilization of calcium-release channel (ryanodine receptor) as a novel therapeutic strategy against heart failure. Circulation 107, 477-84.

Yano, M., Ono, K., Ohkusa, T., Suetsugu, M., Kohno, M., Hisaoka, T., Kobayashi, S., Hisamatsu, Y., Yamamoto, T., Noguchi, N., et al. (2000). Altered stoichiometry of FKBP12.6 versus ryanodine receptor as a cause of abnormal Ca(2+) leak through ryanodine receptor in heart failure, Circulation 102, 2131-6.

What is claimed is:

1. A process for determining whether a first agent inhibits dissociation of FKBP12 from the type 1 ryanodine (RyR1) receptor, comprising:

(a) separately contacting (i) skeletal muscle cells expressing the RyR1 receptor or (ii) sarcoplasmic reticulum or endoplasmic reticulum from an extract from such cells, with (1) both the first agent and a second agent known to cause dissociation of FKBP12 from the RyR1 receptor and with (2) only such second agent, under conditions suitable for dissociation of FKBP12 binding protein from the RyR1 receptor in the presence of such second agent; and (b) measuring the extent of dissociation of FKBP 12 from the RyR1 receptor in the skeletal muscle cells in the presence of only the second agent and in the presence of both the fist and second agents, a smaller extent of dissociation of FKBP12 from the RyR1 receptor in the presence of both the first agent and the second agent than in the presence of only the second agent indicating that the first agent inhibits the extent of dissociation of FKBP12 from the RyR1 receptor, so as to thereby determine whether the first agent inhibits dissociation of FKBP12 from the type 1 ryanodine (RyR1) receptor.

2. The process of claim 1, wherein the first agent is not previously known to inhibit dissociation of FKBP12 from the RyR1 receptor.

3. A process for screening a plurality of agents not known to inhibit dissociation of FKBP12 from RyR1 receptor to identify an agent that inhibits dissociation of FKBP12 from RyR1 receptor, which comprises:

(a) contacting (i) skeletal muscle cells expressing RyR1 receptor or (ii) sarcoplasmic reticulwn or endoplasmic reticulum from an extract from such cells, with one or more of the plurality of agents in the presence of a dissociating agent known to cause dissociation of FKBP12 from RyR1 receptor, under conditions permitting dissociation of FKBP12 from RyR1 receptor in the presence of such dissociating agent;

(b) determining whether the extent of dissociation of FKBP12 from RyR1 receptor in the skeletal muscle cells is reduced in the presence of one or more of the plurality of agents, relative to the extent of dissociation of FKBP12 in the absence of such agents; and (c) if the extent of dissociation determined in step (b) is reduced in the presence of more than one of such agents, separately determining whether such agent inhibits the extent of dissociation of FKBP12 from RyR1 receptor in skeletal muscle cells, so as to thereby determine whether such agent in such plurality of agents inhibits dissociation of FKBP 12 from RyR1 receptor.

4. The process of claim 1 or 3, wherein determining the extent of dissociation of FKBP12 from RyR1 receptor comprises measuring the fluorescence of a calcium-sensitive fluorescent dye, wherein an increase in fluorescence is indicative of an increase in dissociation of FKBP12 from the RyR1 receptor.

5. The process of claim 1 or 3, wherein the RyR1 receptor is a human RyR1 receptor.

6. The process of claim 1 or 3, wherein cells are contacted with the agent(s) and the RyR1 receptor is expressed from nucleic acid endogenous to such cells.

7. The process of claim 1 or 3, wherein cells are contacted with the agent(s) and the RyR1 receptor is expressed from nucleic acid transfected into such cells.

8. The process of claim 7, wherein the skeletal muscle cells are mammalian cells.

9. The process of claim 1 or 3, wherein the cells are skeletal muscle cells from a subject with a failing heart.

10. The process of claim 9, wherein the subject is (a) a non-human animal in which heart failure has been induced by rapid cardiac pacing or (b) a human.

* * * * *